United States Patent
Liu et al.

(10) Patent No.: US 12,156,918 B2
(45) Date of Patent: Dec. 3, 2024

(54) NEUROENDOCRINE CANCER TARGETED THERAPY

(71) Applicant: THE UAB RESEARCH FOUNDATION, Birmingham, AL (US)

(72) Inventors: Xiaoguang Liu, Vestavia Hills, AL (US); Lufang Zhou, Vestavia Hills, AL (US); Jianfa Ou, Fremont, CA (US); Yingnan Si, Birmingham, AL (US); Renata Jaskula-Sztul, Madison, WI (US); Herbert Chen, Mountain Brook, AL (US); Jason Derek Whitt, Birmingham, AL (US); Jianyi Zhang, Vestavia Hills, AL (US)

(73) Assignee: The UAB Research Foundation, Birmingham, AL (US)

( * ) Notice: Subject to any disclaimer, the term of this patent is extended or adjusted under 35 U.S.C. 154(b) by 862 days.

(21) Appl. No.: 17/283,326

(22) PCT Filed: Oct. 8, 2019

(86) PCT No.: PCT/US2019/055145
§ 371 (c)(1),
(2) Date: Apr. 7, 2021

(87) PCT Pub. No.: WO2020/076791
PCT Pub. Date: Apr. 16, 2020

(65) Prior Publication Data
US 2021/0340264 A1    Nov. 4, 2021

Related U.S. Application Data

(60) Provisional application No. 62/742,567, filed on Oct. 8, 2018.

(51) Int. Cl.
| | | |
|---|---|---|
| *A61K 47/68* | (2017.01) | |
| *A61K 45/06* | (2006.01) | |
| *A61P 35/00* | (2006.01) | |
| *C07K 16/28* | (2006.01) | |

(52) U.S. Cl.
CPC .......... *A61K 47/6849* (2017.08); *A61K 45/06* (2013.01); *A61K 47/68031* (2023.08); *A61P 35/00* (2018.01); *C07K 16/2869* (2013.01)

(58) Field of Classification Search
CPC .................. A61K 47/6849; A61K 47/6801
See application file for complete search history.

(56) References Cited

U.S. PATENT DOCUMENTS

| | | | |
|---|---|---|---|
| 6,815,540 B1 | 11/2004 | Pluckthun et al. | |
| 8,580,714 B2 | 11/2013 | Almagro et al. | |
| 2013/0189285 A1 | 7/2013 | Skerry et al. | |
| 2018/0118827 A1* | 5/2018 | Moore | A61P 35/00 |

FOREIGN PATENT DOCUMENTS

| | | |
|---|---|---|
| CN | 107530435 A | 1/2018 |
| CN | 109422809 A | 3/2019 |

OTHER PUBLICATIONS

European Search Report, European Patent Application No. 19870180.7, mailed Jun. 1, 2022 (6 pages).
Lue, Frank P., et al., "GPCR Somatostatin Receptor Extracellular Loop 2 is a Key Ectodomain for Making Subtype-Selective Antibodies with Agonist-Like Activities in the Pancreatic Neuroendocrine Tumor BON Cell Line," Pancreas, vol. 39, No. 8 (2010), pp. 1155-1166.
Kuan, Chien-Tsun, et al., "Detection of Amino-terminal Extracellular Domain of Somatostatin Receptor 2 by Specific Monoclonal Antibodies and Quantification of Receptor Density in Medulloblastoma," Hybridoma, vol. 28, No. 6 (2009), pp. 389-403.
Garcia-Alvarez, Alejandro, et al., "Drug Development in Neuroendocrine Tumors: What is on the Horizon?", Curr. Treat. Options in Oncol., vol. 22, No. 5 (2021), (19 pages).
International Search Report for PCT/US2019/055145 mailed Jan. 15, 2020.
UniProtKB_A0A2E6H9V4, Uncharacterized protein. Last modified: Jan. 31, 2018 [online]. [Retrieved on Dec. 4, 2019]. Retrieved from the Internet :< URL: https://www.uniprot.org/uniproVAOA2E6H9V4 > Protein; and Sequence (465 a.a.), the region between amino acid residues 5-12.
Kuan et al., Detection of Amino-terminal Extracellular Domain of Somatostatin Receptor 2 by Specific Monoclonal Antibodies and Quantification of Receptor Density in Medulloblastoma, Hybridoma (Larchmt), vol. 28(6), p. 389-403, 2009.
First Office Action, issued by Chinese Patent Office, CN Patent Application No. 201980079726.X, Jul. 19, 2023.

* cited by examiner

*Primary Examiner* — Vanessa L. Ford
*Assistant Examiner* — Sandra Carter
(74) *Attorney, Agent, or Firm* — Thomas | Horstemeyer, LLP

(57) ABSTRACT

A majority of neuroendocrine (NE) cancers overexpress somatostatin receptors (SSTRs). Disclosed herein are anti-SSTR2 monoclonal antibodies, and antibody-drug conjugates (ADCs) for use as NE cancer targeting therapeutics. Also disclosed is an isolated nucleic acid encoding the disclosed antibodies, as well as nucleic acid vectors containing this isolated nucleic acid operably linked to an expression control sequence. Also disclosed are cells transfected with these vectors and the use of these cells to produce the disclosed recombinant antibodies. Also disclosed is a method of treating a neuroendocrine (NE) cancer in a subject, comprising administering to the subject an effective amount of the disclosed antibody conjugated to an anti-cancer agent.

12 Claims, 33 Drawing Sheets
Specification includes a Sequence Listing.

FIG. 2A
FIG. 2B
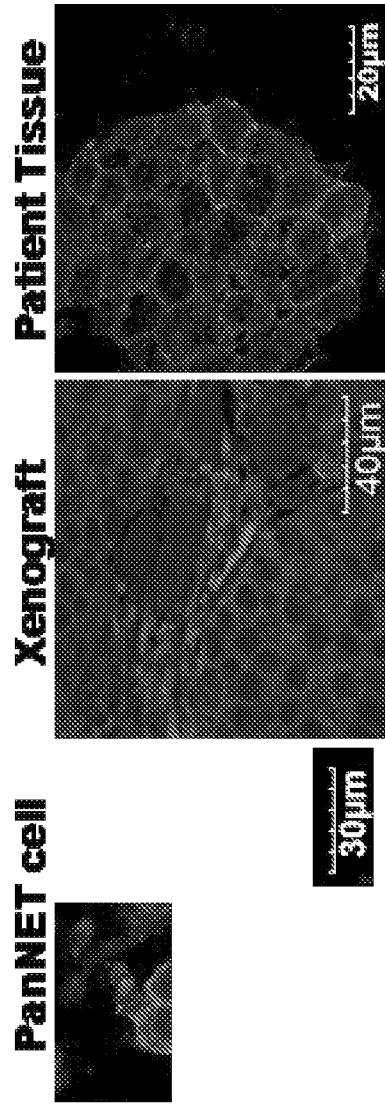
FIG. 2C

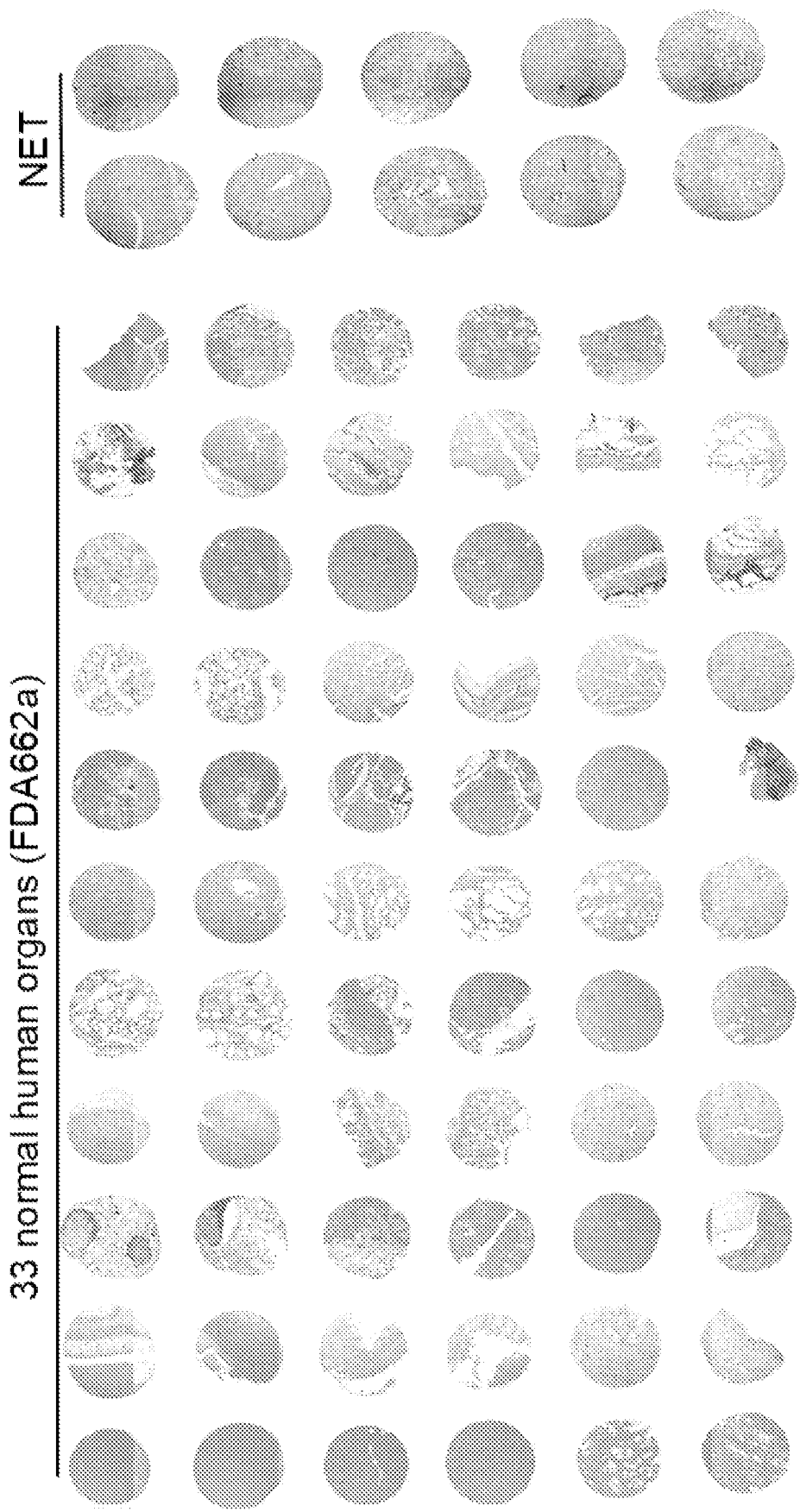
FIG. 8A2
FIG. 8A1

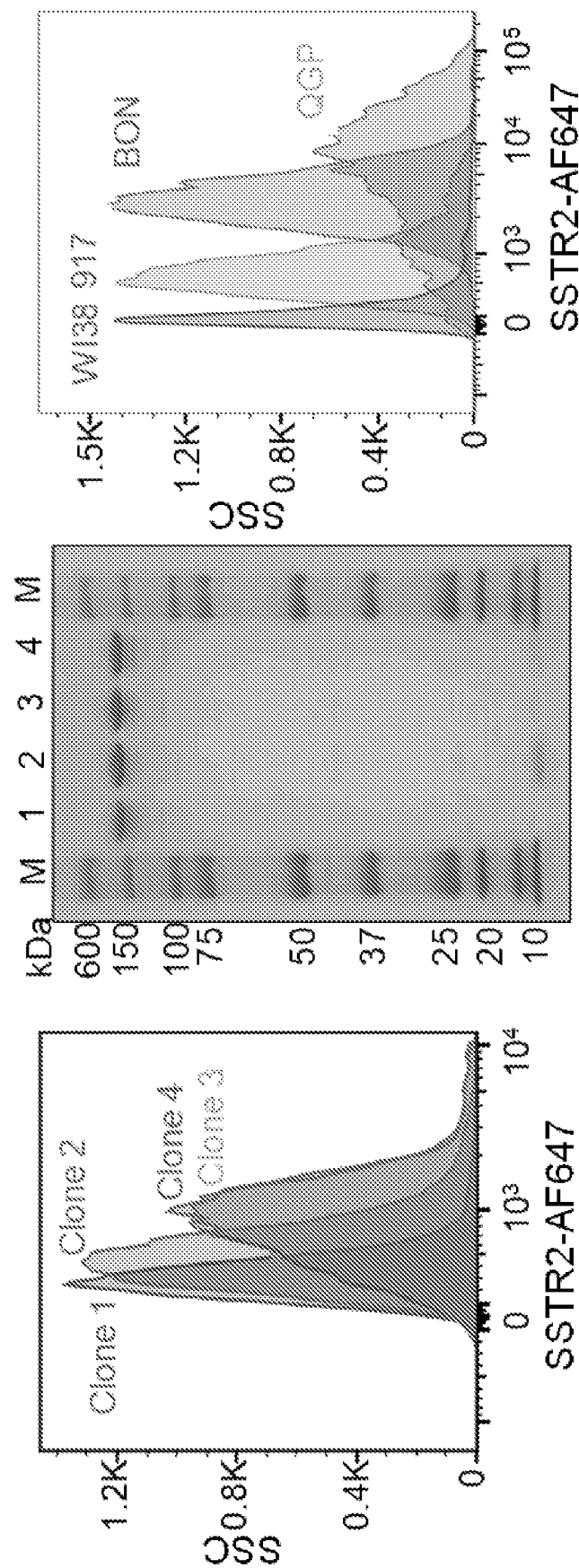

ADC

Saline

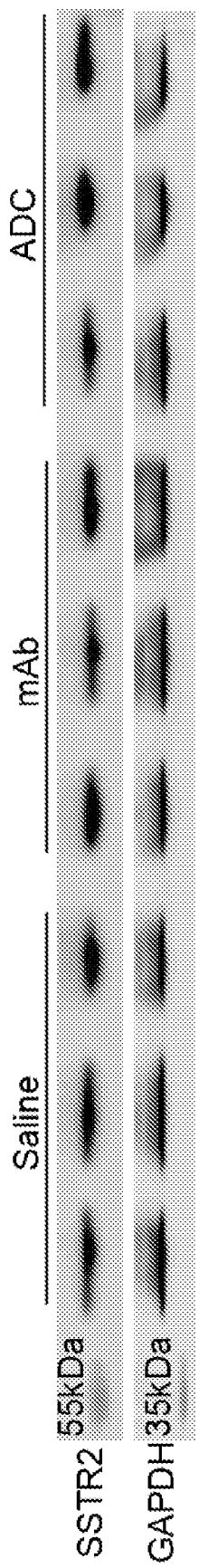
FIG. 14F
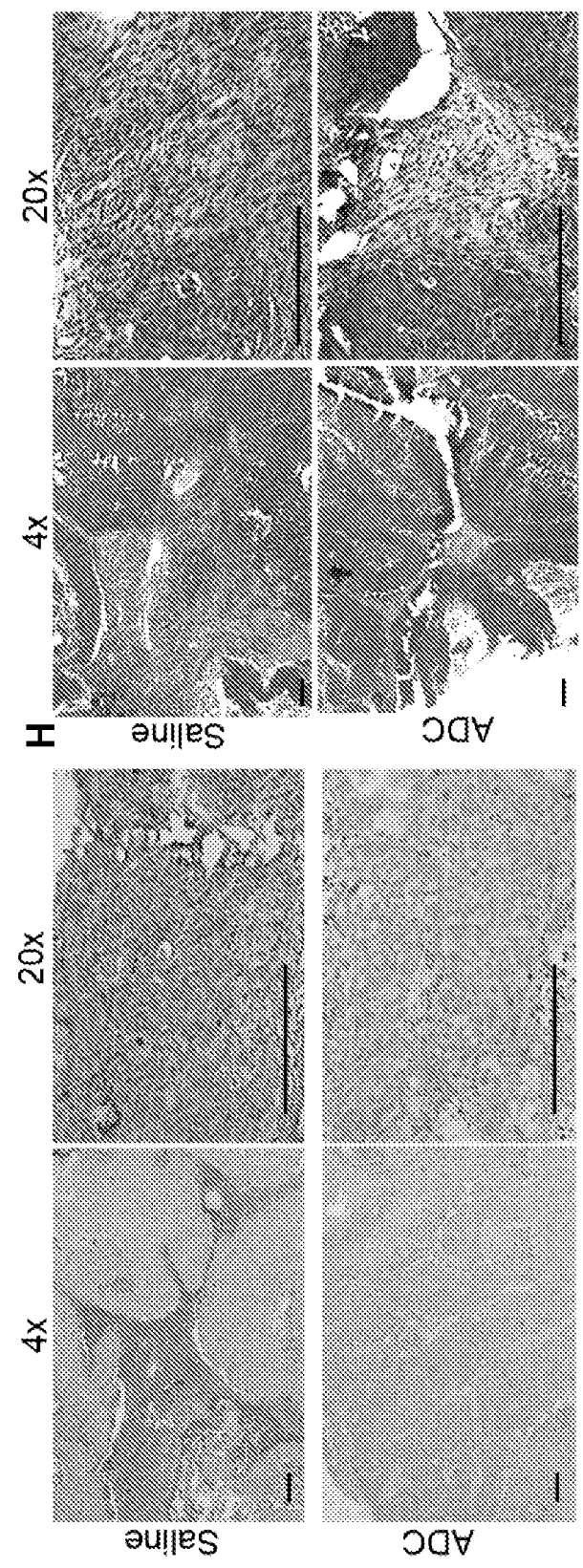
FIG. 14H
FIG. 14G

NEUROENDOCRINE CANCER TARGETED THERAPY

CROSS-REFERENCE TO RELATED APPLICATIONS

This application is a National Stage of International Application No. PCT/US2019/055145, filed Oct. 8, 2019, which claims benefit of U.S. Provisional Application No. 62/742,567, filed Oct. 8, 2018, which is hereby incorporated herein by reference in its entirety.

SEQUENCE LISTING

This application contains a sequence listing filed in electronic form as an ASCII.txt file entitled "222104_2890_Sequence_Listing_ST25" created on Oct. 8, 2019. The content of the sequence listing is incorporated herein in its entirety.

BACKGROUND

Neuroendocrine (NE) cancers such as carcinoids, pancreatic islet cell tumors, and medullary thyroid cancer (MTC) frequently metastasize to the liver (Adler J T, et al. Oncologist. 2008 13(7):779-93; Pinchot S N, et al. Curr Opin Investig Drugs. 2008 9(6):576-82; Chen H, et al. J Am Coll Surg. 1998 187(1):88-92; Chen H, et al. J Gastrointest Surg. 1998 2(2):151-5; Chen H. J Surg Oncol. 2008 97(3):203-4). They are the second most prevalent GI malignancy (Yao J C, et al. J Clin Oncol. 2008 26(18):3063-72). Ninety percent of patients with pancreatic carcinoid tumors and 50% of patients with islet cell tumors develop isolated hepatic metastases (Hiller N, et al. Abdom Imaging. 1998 23(2): 188-90; Brown K T, et al. J Vasc Intery Radiol. 1999 10(4):397-403; Pinchot S N, et al. Oncologist. 2008 13(12): 1255-69; Isozaki T, et al. Intern Med. 1999 38(1):17-21). Patients with untreated, isolated NE liver metastases have a <30% 5-year survival probability. It is reported that in the United States there is an excess of 100,000 patients living with NE cancers, 16,000 new diagnoses each year, and estimated more than 200,000 undiagnosed cases (Chen H, et al. J Am Coll Surg. 1998 187(1):88-92; Norton J A. Best Pract Res Clin Gastroenterol. 2005 19(4):577-8). Thus, it is imperative to develop new therapies to treat NE cancers.

Surgical resection alone is often curative in early-stage disease with localized tumors, but 40-95% of NE cancer patients are metastatic at the time of initial diagnosis (Shiba S, et al. Pancreatology. 2016 16(1):99-105) and the widespread metastases make complete resections impossible. Considering the high degree of hepatic involvement by NE cancers, many patients are not candidates for operative intervention and NE cancer resection is often followed by recurrence within the surgical bed. Other forms of therapy, including chemoembolization, radioembolization, radiofrequency ablation, cryoablation and chemotherapy (i.e. the mTOR inhibitor "everolimus" and multikinase inhibitor "sunitinib"), showed limited efficacy and caused severe systemic toxicities (Brown K T, et al. J Vasc Intery Radiol. 1999 10(4):397-403; Isozaki T, et al. Intern Med. 1999 38(1):17-21; Eriksson B, et al. Neuroendocrinology. 2008 87(1):8-19; Lal A, et al. Curr Opin Oncol. 2006 18(1):9-15; Lehnert T. Transplantation. 1998 66(10):1307-12; Zhang R, et al. Endocrinology. 1999 140(5):2152-8; Boudreaux J P, et al. Ann Surg. 2005 241(6):839-45; Nguyen C, et al. J Nucl Med. 2004 45(10):1660-8; Fiorentini G, et al. J Chemother. 2004 16(3):293-7; Zuetenhorst J M, et al. Endocr Relat Cancer. 2004 11(3):553-61). Therefore, besides surgery, there are no curative treatments for metastatic NE cancers. Furthermore, patients with liver metastases from NE cancers often have debilitating symptoms, such as uncontrollable diarrhea, flushing, skin rashes, and heart failure, due to the excessive hormone secretion that characterizes these tumors (Brown K T, et al. J Vasc Intery Radiol. 1999 10(4):397-403; Miller C A, et al. Surg Oncol Clin N Am. 1998 7(4):863-79). Thus, NE cancer patients frequently have a poor quality of life, emphasizing the critical need for the development of new therapeutic strategies to reduce the progression of NE malignancies.

SUMMARY

A majority of neuroendocrine (NE) cancers overexpress somatostatin receptors (SSTRs), where the SSTR2 subtype is predominately found on the cell surface in 70-100% of NE tumors (NETs). More specifically, the surface expression level of SSTR2 is approximately 20-fold higher in NETs than that in normal cells. Therefore, disclosed herein are anti-SSTR2 monoclonal antibody (mAb, IgG) and antibody-drug conjugate (ADC) for use as NE cancers-targeted therapeutics. In some embodiments, the disclosed mAb down-regulates oncogenic signaling pathways, reduces hormone accumulation and associated carcinoid heart failure, and increases the cytokine production of T cells. More important, the mAb demonstrates high specificity, strong binding, and effective drug delivery capacity to SSTR2-overexpressing NET. In doing so, the disclosed ADC has the integrated clinical benefits of SSTR2-targeted mAb and the highly potent drug delivered by mAb, which can overcome the nonspecific binding and severe systemic toxicities observed in traditional chemo-therapy.

The disclosed anti-SSTR2 monoclonal antibody was produced using two peptides cloned from the $2^{nd}$ and $4^{th}$ extracellular domains of human SSTR2. Also disclosed is an antibody fragment that specifically binds SSTR2. For example, the antibody can be a Fab or a single-chain variable fragment (scFv) of an antibody that specifically binds SSTR2. Also disclosed herein are recombinant, humanized, and/or chimeric antibodies comprising at least the antigen binding regions of the disclosed antibody. In some embodiments, the anti-SSTR2 region (e.g. scFv) can comprise a variable heavy ($V_H$) domain having CDR1, CDR2 and CDR3 sequences and a variable light ($V_L$) domain having CDR1, CDR2 and CDR3 sequences.

In some embodiments, the CDR1 sequence of the $V_H$ domain comprises the amino acid sequence DYHLN (SEQ ID NO:1) DYHMN (SEQ ID NO:26); the CDR2 sequence of the $V_H$ domain comprises the amino acid sequence IRNKRYGYRTEYSASVKG (SEQ ID NO:2) or LIRNK-ANGYRTEYSASVKG (SEQ ID NO:27); the CDR3 sequence of the $V_H$ domain comprises the amino acid sequence DFYDPFAY (SEQ ID NO:3); the CDR1 sequence of the $V_L$ comprises the amino acid sequence RSSQSLVHSNGNTYLH (SEQ ID NO:4); the CDR2 sequence of the $V_L$ domain comprises the amino acid sequence KVSNRFS (SEQ ID NO:5); and the CDR3 sequence of the $V_L$ domain comprises the amino acid sequence SQSTHVPFT (SEQ ID NO:6) or SQSTRVPFT (SEQ ID NO:28).

In some embodiments, the anti-SSTR2 $V_H$ domain comprises the amino acid sequence:

(SEQ ID NO: 7)
EVKLVESGGGLVQPGGSLRLSCATSGFTFTDYHLNWVRQPPGKALEWL

ALIRNKRYGYRTEYSASVKGRFTISRDNSQSILYLQMNTLRAEDSATY

YCARDFYDPFAYWGQGTLVTVSA.

In some embodiments, the anti-SSTR2 $V_H$ domain comprises the amino acid sequence:

(SEQ ID NO: 18)
EVKLVESGGGLVQPGGSLRLSCATSGFTFTDYHMNWVRQPPGKALEWL

ALIRNKANGYRTEYSASVKGRFTISRDNSQNILYLQMNTLRAEDSATY

YCARDFYDPFAYWGQGTLVTVSA.

In some embodiments, the anti-SSTR2 $V_L$ domain comprises the amino acid sequence:

(SEQ ID NO: 8)
DVVMTQTPLSLPVSLGDQASISCRSSQSLVHSNGNTYLHWYLQRPGQS

PKLLIYKVSNRFSGVPDRFSGSGSGTDFTLKISRVEAEDLGVYFCSQS

THVPFTFGSGTKLEIK.

In some embodiments, the anti-SSTR2 $V_L$ domain comprises the amino acid sequence:

(SEQ ID NO: 19)
DVVMTQTPLSLPVSLGDQASISCRSSQSLVHSNGNTYLHWYLQRPGQS

PNLLIYKVSNRFSGVPDRFSGSGSGTDFTLKISRVEAEDLGLYFCSQS

TRVPFTFGSGTKLEIK.

In some embodiments, the VH or VL domain further comprises a signal peptide, such as MKLWLNWI-FLVTLLNGIQC (SEQ ID NO:29) or MKLPVGLL-VLMFWIPASSS (SEQ ID NO:30).

The heavy and light chains are preferably separated by a linker. Suitable linkers for scFv antibodies are known in the art. In some embodiments, the linker comprises the amino acid sequence GGGGSGGGGSGGGGS (SEQ ID NO:9), SSGGGGSGGGGSGGS (SEQ ID NO:10), or GST-SGSGKPGSGEGSTKG (SEQ ID NO:11). The scFv can have the formula $NH_3-V_H$-linker-$V_L$-COOH or $NH_3-V_L$-linker-$V_H$-COOH.

Therefore, in some embodiments, the anti-SSTR2 scFv comprises an amino acid sequence:

(SEQ ID NO: 12)
MKLWLNWIFLVTLLNGIQCEVKLVESGGGLVQPGGSLRLSCATSGFTF

TDYHLNWVRQPPGKALEWLALIRNKRYGYRTEYSASVKGRFTISRDNS

QSILYLQMNTLRAEDSATYYCARDFYDPFAYWGQGTLVTVSAGGGGSG

GGGSGGGGSMKLPVRLLVLMFWIPASSSDVVMTQTPLSLPVSLGDQAS

ISCRSSQSLVHSNGNTYLHWYLQRPGQSPKLLIYKVSNRFSGVPDRFS

GSGSGTDFTLKISRVEAEDLGVYFCSQSTHVPFTFGSGTKLEIK.

Therefore, in some embodiments, the anti-SSTR2 scFv comprises an amino acid sequence:

(SEQ ID NO: 13)
MKLPVRLLVLMFWIPASSSDVVMTQTPLSLPVSLGDQASISCRSSQSL

VHSNGNTYLHWYLQRPGQSPKLLIYKVSNRFSGVPDRFSGSGSGTDFT

LKISRVEAEDLGVYFCSQSTHVPFTFGSGTKLEIKGGGGSGGGGSGGG

GSMKLWLNWIFLVTLLNGIQCEVKLVESGGGLVQPGGSLRLSCATSGF

TFTDYHLNWVRQPPGKALEWLALIRNKRYGYRTEYSASVKGRFTISRD

NSQSILYLQMNTLRAEDSATYYCARDFYDPFAYWGQGTLVTVSA.

Therefore, in some embodiments, the anti-SSTR2 scFv comprises an amino acid sequence:

(SEQ ID NO: 20)
MKLWLNWIFPVTLLNGIQCEVKLVESGGGLVQPGGSLRLSCATSGFTF

TDYHMNWVRQPPGKALEWLALIRNKANGYRTEYSASVKGRFTISRDNS

QNILYLQMNTLRAEDSATYYCARDFYDPFAYWGQGTLVTVSAGGGGSG

GGGSGGGGSMKLPVGLLVLMFWIPASSSDVVMTQTPLSLPVSLGDQAS

ISCRSSQSLVHSNGNTYLHWYLQRPGQSPNLLIYKVSNRFSGVPDRFS

GSGSGTDFTLKISRVEAEDLGLYFCSQSTRVPFTFGSGTKLEIK.

Therefore, in some embodiments, the anti-SSTR2 scFv comprises an amino acid sequence:

(SEQ ID NO: 21)
MKLPVGLLVLMFWIPASSSDVVMTQTPLSLPVSLGDQASISCRSSQSL

VHSNGNTYLHWYLQRPGQSPNLLIYKVSNRFSGVPDRFSGSGSGTDFT

LKISRVEAEDLGLYFCSQSTRVPFTFGSGTKLEIKGGGGSGGGGSGGG

GSMKLWLNWIFPVTLLNGIQCEVKLVESGGGLVQPGGSLRLSCATSGF

TFTDYHMNWVRQPPGKALEWLALIRNKANGYRTEYSASVKGRFTISRD

NSQNILYLQMNTLRAEDSATYYCARDFYDPFAYWGQGTLVTVSA.

Therefore, in some embodiments, the anti-SSTR2 scFv comprises an amino acid sequence:

(SEQ ID NO: 22)
MKLWLNWIFLVTLLNGIQCEVKLVESGGGLVQPGGSLRLSCATSGFTF

TDYHLNWVRQPPGKALEWLALIRNKRYGYRTEYSASVKGRFTISRDNS

QSILYLQMNTLRAEDSATYYCARDFYDPFAYWGQGTLVTVSAGGGGSG

GGGSGGGGSMKLPVGLLVLMFWIPASSSDVVMTQTPLSLPVSLGDQAS

ISCRSSQSLVHSNGNTYLHWYLQRPGQSPNLLIYKVSNRFSGVPDRFS

GSGSGTDFTLKISRVEAEDLGLYFCSQSTRVPFTFGSGTKLEIK.

Therefore, in some embodiments, the anti-SSTR2 scFv comprises an amino acid sequence:

(SEQ ID NO: 23)
MKLPVGLLVLMFWIPASSSDVVMTQTPLSLPVSLGDQASISCRSSQSL

VHSNGNTYLHWYLQRPGQSPNLLIYKVSNRFSGVPDRFSGSGSGTDFT

LKISRVEAEDLGLYFCSQSTRVPFTFGSGTKLEIKGGGGSGGGGSGGG

GSMKLWLNWIFLVTLLNGIQCEVKLVESGGGLVQPGGSLRLSCATSGF

-continued

TFTDYHLNWVRQPPGKALEWLALIRNKRYGYRTEYSASVKGRFTISRD

NSQSILYLQMNTLRAEDSATYYCARDFYDPFAYWGQGTLVTVSA.

Therefore, in some embodiments, the anti-SSTR2 scFv comprises an amino acid sequence:

(SEQ ID NO: 24)
MKLWLNWIFPVTLLNGIQCEVKLVESGGGLVQPGGSLRLSCATSGFTF

TDYHMNWVRQPPGKALEWLALIRNKANGYRTEYSASVKGRFTISRDNS

QNILYLQMNTLRAEDSATYYCARDFYDPFAYWGQGTLVTVSAGGGGSG

GGGSGGGGSMKLPVRLLVLMFWIPASSSDVVMTQTPLSLPVSLGDQAS

ISCRSSQSLVHSNGNTYLHWYLQRPGQSPKLLIYKVSNRFSGVPDRFS

GSGSGTDFTLKISRVEAEDLGVYFCSQSTHVPFTFGSGTKLEIK.

Therefore, in some embodiments, the anti-SSTR2 scFv comprises an amino acid sequence:

(SEQ ID NO: 25)
MKLPVRLLVLMFWIPASSSDVVMTQTPLSLPVSLGDQASISCRSSQSL

VHSNGNTYLHWYLQRPGQSPKLLIYKVSNRFSGVPDRFSGSGSGTDFT

LKISRVEAEDLGVYFCSQSTHVPFTFGSGTKLEIKGGGGSGGGGSGGG

GSMKLWLNWIFPVTLLNGIQCEVKLVESGGGLVQPGGSLRLSCATSGF

TFTDYHMNWVRQPPGKALEWLALIRNKANGYRTEYSASVKGRFTISRD

NSQNILYLQMNTLRAEDSATYYCARDFYDPFAYWGQGTLVTVSA.

Also disclosed is an isolated nucleic acid encoding the disclosed antibodies, as well as nucleic acid vectors containing this isolated nucleic acid operably linked to an expression control sequence. Also disclosed are cells transfected with these vectors and the use of these cells to produce the disclosed recombinant antibodies.

Also disclosed is a composition comprising the disclosed antibody conjugated to an anti-cancer agent. The disclosed antibody can be used to deliver any payload to NE cancers in a subject. The payload can be a therapeutic or diagnostic agent. In some embodiments, the payload is an anti-cancer agent that can cause apoptosis or pyroptosis of the targeted tumor cell. In some embodiments, the anti-cancer agent is a small molecule drug. In some embodiments, the anti-cancer agent is monomethyl auristatin E, gemcitabine, or resveratrol. The anti-cancer agent can be a chemotherapy agent, such as drugs that stop DNA building block synthesis (e.g., methotrexate, fluorouracil, hydroxyurea, lurtotecan, mercaptopurine, pentostatin and pirarubicin), drugs that directly damage DNA (e.g., cisplatin, daunorubicin, doxorubicin, etoposide, teniposide, camptothecin, topotecan, irinotecan, rubitecan, belotecan), drugs that affect mitotic spindle synthesis or breakdown (e.g., vinblastine, vincristine, vinorelbine, vinflunine, vindesine, docetaxel, larotaxel, ortataxel, paclitaxel, tesetaxel, ixabepilone and epithilones), or drugs that disrupt angiogenesis (e.g., anti-VEGF antibody, angiostatin, endostatin, and tumstatin). Alternatively, the anti-cancer agent can be a radiotherapy agent (e.g., 90Y, 125I, 188Re, 111In DTPA, or 131I Sodium iodide).

Examples of anti-cancer drugs or antineoplastics to be attached to the tumor targeting peptides described herein include, but are not limited to, aclarubicin, altretamine, aminopterin, amrubicin, azacitidine, azathioprine, belotecan, busulfan, camptothecin, capecitabine, carboplatin, carmofur, carmustine, chlorambucil, cisplatin, cladribine, clofarabine, cyclophosphamide, cytarabine, daunorubicin, decitabine, doxorubicin, epirubicin, etoposide, floxuridine, fludarabine, 5-fluorouracil, fluorouracil, gemcitabine, idarubicin, ifosfamide, irinotecan, mechlorethamine, melphalan, mercaptopurine, methotrexate, mitoxantrone, nedaplatin, oxaliplatin, paclitaxel, pemetrexed, pentostatin, pirarubicin, pixantrone, procarbazine, pyrimethamine raltitrexed, rubitecan, satraplatin, streptozocin, thioguanine, triplatin tetranitrate, teniposide, topotecan, tegafur, trimethoprim, uramustine, valrubicin, vinblastine, vincristine, vindesine, vinflunine, vinorelbine, and zorubicin.

In come embodiments, the disclosed antibody is linked to a vehicle carrier, which is associated with the anti-cancer agent. In one example, the vehicle carrier encapsulates the anti-cancer agent. Vehicle carriers include, but are not limited to, exosome, micelle, liposome (e.g., cationic liposome), nanoparticle, microsphere, or biodegradable polymer. A tumor targeting peptide can be tethered to a vehicle carrier by a variety of linkages (e.g., a disulfide linkage, an acid labile linkage, a peptide-based linkage, an oxyamino linkage, or a hydrazine linkage). To improve the association between the antibody and the vehicle carrier, the peptide can be modified by a suitable polymer, such as PEG (peglyated). The detectable label or the anti-cancer agent can be encapsulated within the vehicle via, e.g., association with lipophilic molecules, which can aid in the delivery of the detectable label or the anti-cancer agent to the interior of the vehicle.

In some embodiments, a tumor targeting antibody described herein is linked to a liposome (as a vehicle carrier) that encapsulates one or more agents of interest (e.g., an anti-cancer agent). Liposome is a vesicle comprised of one or more concentrically ordered lipid bilayers, which encapsulate an aqueous phase. The aqueous phase typically contains an agent to be delivered to a target site such as a tumor site. Upon reaching the target site, the liposome fuses with the plasma membranes of local cells to release the agent into the cytosol. Alternatively, the liposome is endocytosed or otherwise taken in by the cells as the content of a transport vesicle (e.g., an endosome or phagosome). Once in the transport vesicle, the liposome either degrades or fuses with the membrane of the vesicle and releases its contents. Liposome membranes can be constructed so that they become destabilized when the nearby environment becomes acidic (see, e.g., PNAS 84:7851, 1987; Biochemistry 28:908, 1989). Thus, when liposomes enter a target cell, they become destabilized to release their encapsulated contents. This destabilization process is termed fusogenesis. Dioleoylphosphatidylethanolamine (DOPE) is commonly used to facilitate this process.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

In antibody drug conjugate, the antibody can be conjugated directly to the cytotoxic agent or via a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In some embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

Also disclosed is a pharmaceutical composition comprising the tumor targeting antibody and payload disclosed herein in a pharmaceutically acceptable carrier. Also disclosed is a method for treating a NE cancers in a subject that involves administering to the subject a therapeutically effective amount of a disclosed pharmaceutical composition.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A to 2C show the evaluation of SSTR2 expression. (A) RT-PCR indicated high SSTR2 level in BON cell. (B) Whole cell Western blot showed low SSTR2 in non-cancerous cells (917 and WI38) but high SSTR2 in NET cell line (BON, QGP, and H727); Membrane Western blot confirmed low SSTR2 in non-cancerous cells (917) but high SSTR2 in NET cells (H727). (C) CLSM showed high SSTR2 in live PanNET cells (BON), PanNET xenograft tissue and patient tissue.

FIG. 7A shows H&E staining of the TMA including human pancreatic NET tissues (columns 2-9, n=38) and normal tissues (control, column 1, n=5). FIG. 7B shows an IHC analysis of the TMA showed positive staining for SSTR2. Scale bar equals to 20 μm. The 71% of these cores were positive for SSTR2 and showed strong membrane localization.

FIGS. 8A and 8B shows anti-SSTR2 antibody uniquely binds to NET cells but there was no or very low binding to normal organs or tissues as validated by immunohistochemistry. FIG. 8A1 shows negative or very low surface SSTR2 staining in 33 normal human organs (US Biomax, FDA662a, n=2) representing the cerebrum, cerebellum, peripheral nerve, adrenal gland, thyroid gland, spleen, thymus, bone marrow, lymph node, tonsil, pancreas, liver, esophagus, stomach, small intestine, colon, lung, salivary, pharynx, kidney, bladder, testis, prostate, penis, ovary, uterine tube, breast, endometrium, cervix, cardiac muscle, skeletal muscle, mesothelium, and skin. FIG. 8A2 shows positive SSTR2 staining on the cell surface in pancreatic NET patient tissues (n=12). FIG. 8B shows representative high-resolution IHC imaging of cerebellum, cerebrum, liver, lung, muscle, skin, tonsil, prostate, pancreas, and pancreatic NET. Scale bar equals to 50 μm.

FIGS. 9A to 9F show nti-SSTR2 mAb development and production. FIG. 9A shows rank of top anti-SSTR2 mAb clones based on the titer in ELISA screening (data represent mean±SEM, n=3). FIG. 9B shows evaluation of top 4 clones using flow cytometry. FIG. 9C shows SDS-PAGE confirmed the integrity and purity of mAb (M: marker; 1-4: Clones 1-4). FIG. 9D shows evaluation of SSTR2 binding of Clone #4 in control cell lines (WI38 and 917) and NET cell lines (BON and QGP). FIG. 9E shows VCD and viability as a function of time. FIG. 9F shows mAb production and hybridoma cell growth in fed-batch suspension cultures (data represent mean±SEM, n=3). Viable cell density (VCD): ▲, cell viability: Δ, specific growth rate (μ): □.

FIG. 10A shows live-cell CLSM dynamic imaging showing anti-SSTR2 mAb quickly and effectively bound to BON cell surface within 60 mins, followed by internalization within 70 mins. Two-color CLSM: whole cell labeled with GFP and SSTR2 mAb-MMAE labeled with AF647. FIG. 10B shows flow cytometry showing our anti-SSTR2 mAb bound to BON cells at a high level and did not bind to the SSTR2 negative control and our mAb had much higher binding percentage than commercial mAb. Stained with 1 μg of mAb-AF647/million cells on ice for 30 mins. FIG. 10C shows the AF647-mAb were internalized in three NE cancer cells (green), including BON, TT and MZ. Scale bar equals to 5 μm.

FIG. 11A shows in vivo imaging with IVIS showing the mAb could specifically target s.c. NET xenograft in mouse model. The anti-SSTR2 mAb was labelled with fluorescent dye Cy7 and purified using Protein A column. Total of 50 μg Cy5.5-mAb was intravenously (i.v.) injected through tail vein. IVIS images were taken at 24 hr post Cy5.5-mAb injection. FIG. 11B shows the mAb targets both human NET (BON) xenografted tissue and mouse MTC tissues (n=3-4).

FIG. 12A shows molecule structure of anti-SSTR2 mAb-MMAE using re-bridging linker which maintains the integrity of mAb. FIG. 12B shows MS demonstrating the right structure and proper conjugation of linker-MMAE drug in terms of three product formats. FIG. 12C shows the $IC_{50}$ anti-cancer toxicity of free drug (●), ADC constructed using commercial anti-SSTR2 mAb (R&D Systems, ▲), and ADC constructed using our anti-SSTR2 mAb (■) (data represent mean±SEM, n=3). FIG. 12D shows SDS-PAGE gel showing good integrity of mAb-MMAE. FIG. 12E shows western blotting reveling that both anti-SSTR2 mAb and ADC inhibited the proliferation signaling pathways (AKT, Cyclin D1 and P21) while not change SSTR2 surface expression. FIG. 12F shows the MMAE drug caused microtubule de-polymerization in BON cell line. Scale bar equals to 20 μm.

FIG. 13A shows MTD studies that test the effect of five ADC dosages including 4, 8, 12, 16 and 20 mg/kg-BW show no negative effect on mice weight and behaviors and maximal dosage was not reached (n=2). FIG. 13B shows H&E staining showing ADC treatment did not change brain morphology and had no damage to brain. Scale bar equals to 200 μm.

FIGS. 14A to 14H shows anti-NET efficacy study of ADC in PanNET (BON-Luc) xenografted models. FIG. 14A shows tumor volume changes after Bon-Luc cell injection and treatment (data represent mean±SEM, n=6). Tumor was measured with calipers, and calculated as ellipsoid. Black arrow indicating ADC (8 mg/kg BW) treatment date. FIG. 14B shows tumor fluorescence flux measurement with IVIS image system (data represent mean±SEM, n=6). FIG. 14C shows tumor bearing mice harvested. FIG. 14D shows weight of the tumors excised from harvested mice on Day 29. FIG. 14E shows body weight of the mice during treatment. ▲: treatment group injected with ADC, ●: control group injected with mAb, and ■: control group injected with saline. FIG. 14F shows western blotting of tumors from represented mice (n=3). FIG. 14G shows anti-SSTR2 IHC staining of the saline and ADC treated tumors. FIG. 14H shows H&E staining of Saline or ADC treatment tumor. Scale bar equals to 50 μm. ***$p \leq 0.001$.

DETAILED DESCRIPTION

Figure 1:
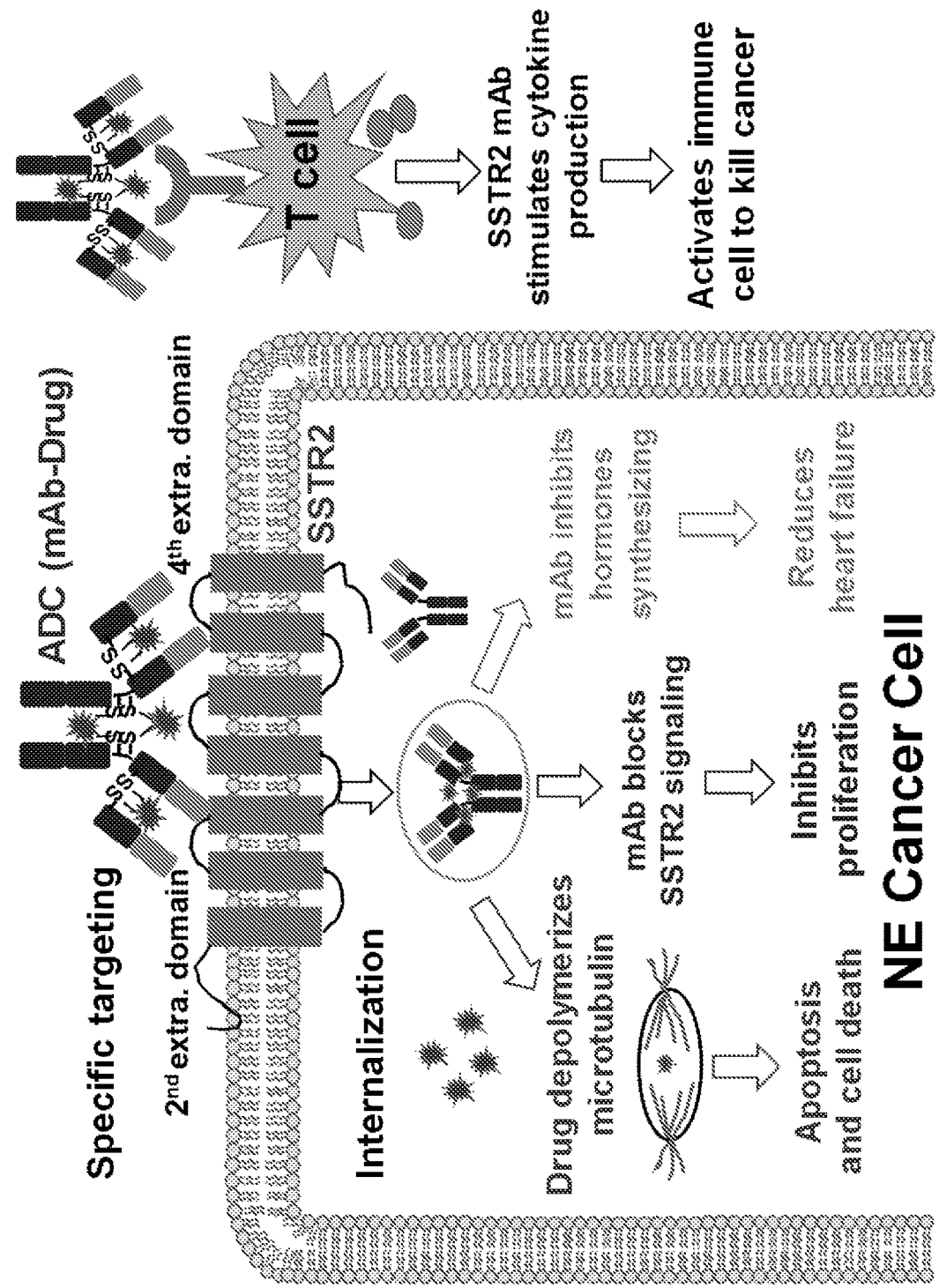
FIG. 1 shows the SSTR2-targeted therapy to treat NET via: 1) depolymerizing microtubulin by the mAb delivered drug, 2) inhibiting hormone production by the internalized mAb, 3) downregulating proliferation signaling pathway through blocking SSTR2 by mAb, or 4) activating T cell's cytokine production.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D, aspartic acid; E, glutamate, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, b $10^{10}$ $M^{-1}$, b $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid subsitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

Disclosed herein are monoclonal antibodies that selectively bind human SSTR2 on cancer cells. Also disclosed herein are recombinant antibodies that can specifically recognize SSTR2-expressing cancers, such as NE cancers.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Also disclosed is a pharmaceutical composition comprising a disclosed antibody in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, PA. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Also disclosed are polynucleotides and polynucleotide vectors encoding the disclosed SSTR2-specific antibodies. Nucleic acid sequences encoding the disclosed antibodies, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding antibodies is typically achieved by operably linking a nucleic acid encoding the antibody to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodimens, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of an antibody or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc, (Birmingham, Ala.).

Also disclosed is a method for treating a SSTR2-expressing cancer in a subject by administering to the subject a therapeutically effective amount of the disclosed pharmaceutical composition. The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a SSTR2-expressing cancer. Thus, the method can further comprise identifying a subject at risk for a SSTR2-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The disclosed antibodies may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodimetns formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed antibodies are administered to a patient in conjunction with (e.g., before, simultaneously or following) any number of relevant treatment modalities, including but not limited to thalidomide, dexamethasone, bortezomib, and lenalidomide. In further embodiments, the disclosed antibodies may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the disclosed antibodies are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any SSTR2-expressing cell in a subject undergoing unregulated growth, invasion, or metastasis. In some embodiments, the SSTR2-expressing cancer is a neuroendocrine (NE) cancer. Neuroendocrine tumors (NETs) are neoplasms that arise from cells of the endocrine (hormonal) and nervous systems. Many are benign, while some are malignant. Traditionally, neuroendocrine tumors have been classified by their anatomic site of origin. NETs can arise in many different areas of the body. They most commonly occur in the intestine, where they are often called carcinoid tumors, but they are also found in the pancreas, lung, and the rest of the body. NETs include certain tumors of the gastrointestinal tract and of the pancreatic islet cells, certain thymus and lung tumors, and medullary carcinoma of the parafollicular cells of the thyroid.

The disclosed antibodies can in some embodiments, be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed antibodies can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with disclosed antibodies for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN , GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C—C chemokine families. Suitable cytokines include cytokine derivatives, cytokine variants, cytokine fragments, and cytokine fusion proteins.

In some embodiments, a therapeutic agent for use in combination with disclosed antibodies for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055) . Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with disclosed antibodies for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with disclosed antibodies for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed antibodies are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed antibodies are administered in combination with surgery.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Overall Design

A majority of NE cancers overexpress somatostatin receptors (SSTRs), where the SSTR2 subtype is predominately found on the cell surface in 70-100% of NE tumors (Pinchot SN, et al. Oncologist. 2008 13(12):1255-6; Zatelli M C, et al. J Clin Endocrinol Metab. 2001 86(5):2161-9; Sun L C, et al. Curr Drug Deliv. 2011 8(1):2-10). More specifically, the surface expression level of SSTR2 is ~20-fold higher in NETs than that in normal cells (Pinchot S N, et al. Oncologist. 2008 13(12):1255-6; Zatelli M C, et al. J Clin Endocrinol Metab. 2001 86(5):2161-9; Sun L C, et al. Curr Drug Deliv. 2011 8(1):2-10). Therefore, anti-SSTR2 monoclonal antibody and antibody-drug conjugate (ADC) are developed as NE cancer targeting therapeutics that regulate tumor progression and deliver a cytotoxic agent directly to SSTR2-expressing NET cells while limiting systemic toxicities (FIG. 1).

Targeted therapies, such as monoclonal antibodies (mAbs) and ADCs, have been developed to effectively treat solid tumors while minimizing side effects on normal cells (24-30), but none of these therapies have been applied to treat NE cancers. ADC as anti-cancer biopharmaceuticals integrates the advantages of mAb, which can specifically bind a tumor associated surface receptor and regulate the receptor associated intracellular signaling pathways, and the potent cytotoxicity of small molecule chemotherapeutics (FIG. 1). A mAb enables the delivered drug to circulate through the bloodstream until it binds to the tumor specific surface antigen. After binding, the ADC is internalized via receptor-mediated endocytosis, a late endosome is formed, lysosomal degradation occurs, the cytotoxic drug is then released into the cytoplasm, and this leads to cancer cell death.

The ADC utilizing the disclosed mAb can achieve specific targeting and highly effective cytotoxicity in NETs while minimizing systemic toxicities. Antibody-drug conjugate (ADC) is developed as NE cancer targeted therapeutics. The highly specific targeting ability of mAbs is essential to improve the clinical efficiency of ADCs. The only commercially available human anti-SSTR2 mAb was developed by using purified whole SSTR2 protein as an immunogen, but this mAb does not show high binding affinity to SSTR2 on NET surface. The disclosed anti-SSTR2 mAb developed using two extracellular peptides as antigens is more efficient in targeting NETs. The high specificity of this anti-SSTR2 mAb assures successful delivery of the drugs and enables selection of a small molecule with high cytotoxic potency (such as MMAE). While MMAE is potent in vitro, it requires tumor targeted delivery to achieve a clinically meaningful therapeutic index in vivo.

An innovative liver metastasis murine model, which was developed to mimic the tumor progression and the microenvironment observed in human NE cancers, or NET s.c. xenografts model enables a full characterization of mAb and ADC and the validation of NE cancer response to ADC and mAb through in vivo system. The sporadic MTC mouse model can be used to investigate the mAb-mediated immune response (Pozo K, et al. Cancer Cell. 2013 24(4):499-511; Pozo K, et al. Oncotarget. 2015; 6(14):12080-93).

The advanced in vitro and in vivo imaging techniques enable direct visualization of the specific targeting and biodistribution of mAb and ADC. The multi-color live-cell imaging technique using confocal laser scanning microscopy (CLSM) enables us to monitor the specific binding as well as the internalization and cleavage of mAb ADC labeled with Alexa Fluor 647 at cellular level. The dynamic nuclear imaging technique using positron emission tomography (PET) facilities us evaluate the in vivo biodistribution and tumor specific targeting in live animal.

Example 2: Generate Antibody-Drug Conjugate (ADC) that Specifically Targets NETs Surface receptor identification and evaluation: Quantification of SSTR2 on transcriptional level detected higher SSTR2 expression in pancreatic NET (PanNET) cells (BON) than in non-cancer cells (WI38 fibroblasts) (FIG. 2A). Additionally, Western blot analysis of PanNET (BON and QGP), pulmonary NET (H727), and non-cancer cells (917 and WI38 fibroblasts) confirmed the high SSTR2 expression in NE cancers, but minimal to no expression in non-cancer cells (FIG. 2B). Using confocal laser scanning microscopy (CLSM) and high-affinity polyclonal antibody, we determined a strong membrane positivity of SSTR2 in BON cells, BON xenograft, and PanNET human tissue (FIG. 2C).

Anti-SSTR2 mAb development: There is no commercially available anti-SSTR2 mAb that targets the surface SSTR2 for therapeutic purpose. To achieve high affinity and specific binding to NET cells we developed and fully evaluated five mouse anti-human SSTR2 mAbs to target the $2^{nd}$ extracellular domain (cQTEPYYDLTSNA, SEQ ID NO:14), $4^{th}$ extracellular domain (cALVHWPFGKAICRVV, SEQ ID NO:15), or both $2^{nd}$ and $4^{th}$ extracellular domains, respectively, using hybridoma technology. We screened over 40 clones using peptide-based enzyme-linked immunosorbent assay (ELISA), flow cytometry and live-cell CLSM.

Recombinant mAb production: Since hybridoma cell lines could be unstable over time and mAb productivity is very low, the RNA isolate from the hybridoma is sequenced to determine the heavy and light chain variable regions. The chimeric top mAb is cloned and expressed using Chinese hamster ovary (CHO) cells. The fed-batch cell culture with nutrients feeding is performed in a 7-L stirred tank bioreactor with precise process controls. Constant process controls as described in our previous publications (Xu N, et al. Biochem Eng J. 2017; 124:122-9), i.e. Temp 37° C. with a shift to 36° C. on day 3, pH 6.8, DO 50%, agitation 75 rpm, and gas sparging 0.01 VVM, are applied to the mAb production.

ADC construction: The ADC is generated by conjugating antibody with a highly potent antimitotic monomethyl auristatin E (MMAE; model drug for ADC) via rebridging dipeptide Mc-Val-Cit-PABC-PNP linker (Xu N, et al. Frontiers of Chemical Science & Engineering. 2017 9(3):376-80; Willuda J, et al. Mol Cancer Ther. 2017 16(5):893-904; McCombs J R, et al. AAPS J. 2015 17(2):339-51). First, the rebridging linker is synthesized by mixing 3.91 mmol 6-aminohexanoic acid with 3.91 mmol 3,4-dibromofuran-2,5-dione in 20 mL of acetic acid at 100° C. for 18 hr, and purified by silica gel with 0-40% eluent solution of dichloromethane/ethyl acetate. Second, the rebridging linker-MMAE is synthesized by mixing 13.55 µmol N,N'-diisopropylcarbodiimide, 13.55 µmol N,N-diisopropylethylamine, and 33.85 µmol rebridging linker in 0.25 mL dichloromethane, followed by adding 13.55 µmol MMAE. After mixing 16 hr, the linker-MMAE is purified with a Waters HPLC equipped with a reversed-phase C18 column and characterized with an Agilent 6500 Q-TOF LC/MS. Third, ADC is produced using in situ conjugation: the 5 mg/mL mAb is reduced by 7 equivalent of tris (2-carboxyethyl) phosphine (TCEP); the linker-MMAE is simultaneously reacted with TCEP at 7 equivalent; and the synthesized ADC is purified by G-25 gel filtration.

Example 3: Evaluate the Anti-NET Toxicity and Mechanism of ADC In Vitro

Figures 3A, 3B:
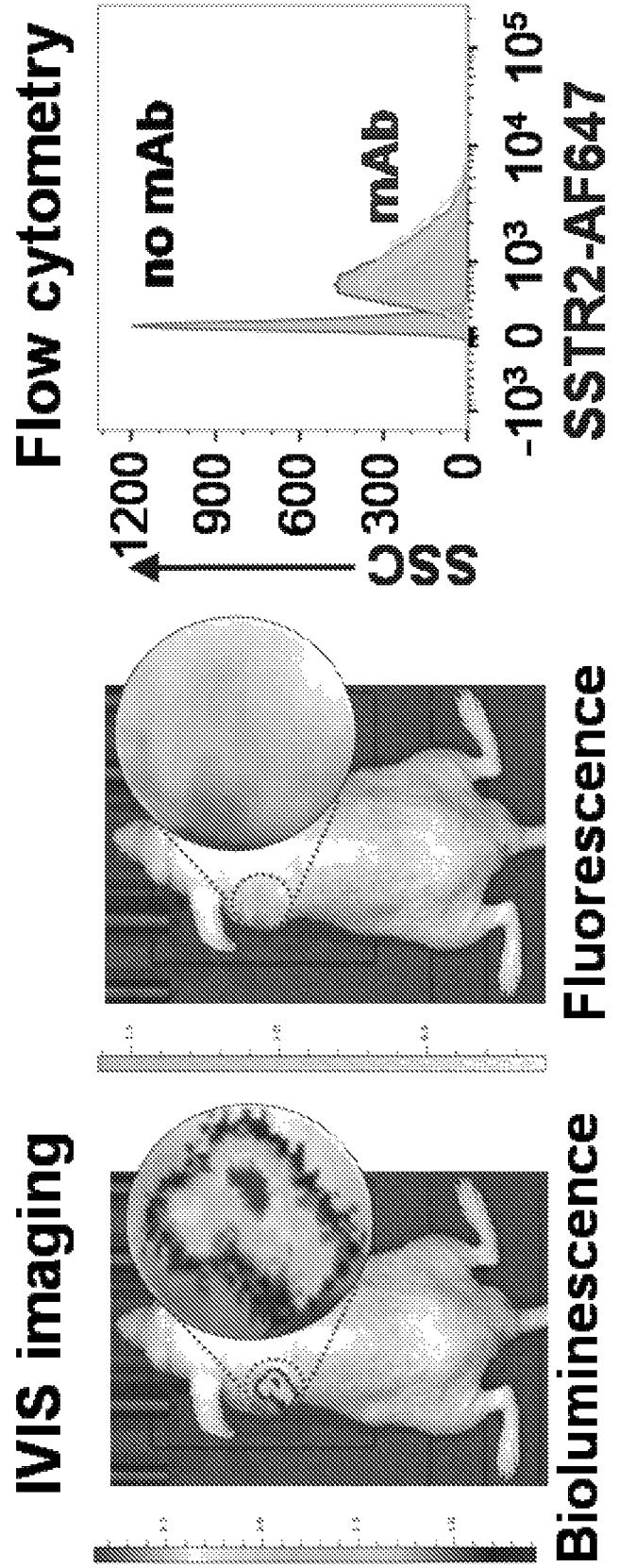
FIGS. 3A and 3B show the specific targeting of the anti-SSTR2 mAb. (A) Live-animal IVIS imaging showed mAb-AF488 accumulation in the s.c. NET xenograft. (Left): Bioluminescent signal from stably transfected NET-Luc cells. (Right): Fluorescence signal from the highly proliferative regions of NET xenograft indicating specific SSTR2-mAb. (B) Flow cytometry demonstrated high surface binding of mAb.
Figures 4A, 4B:
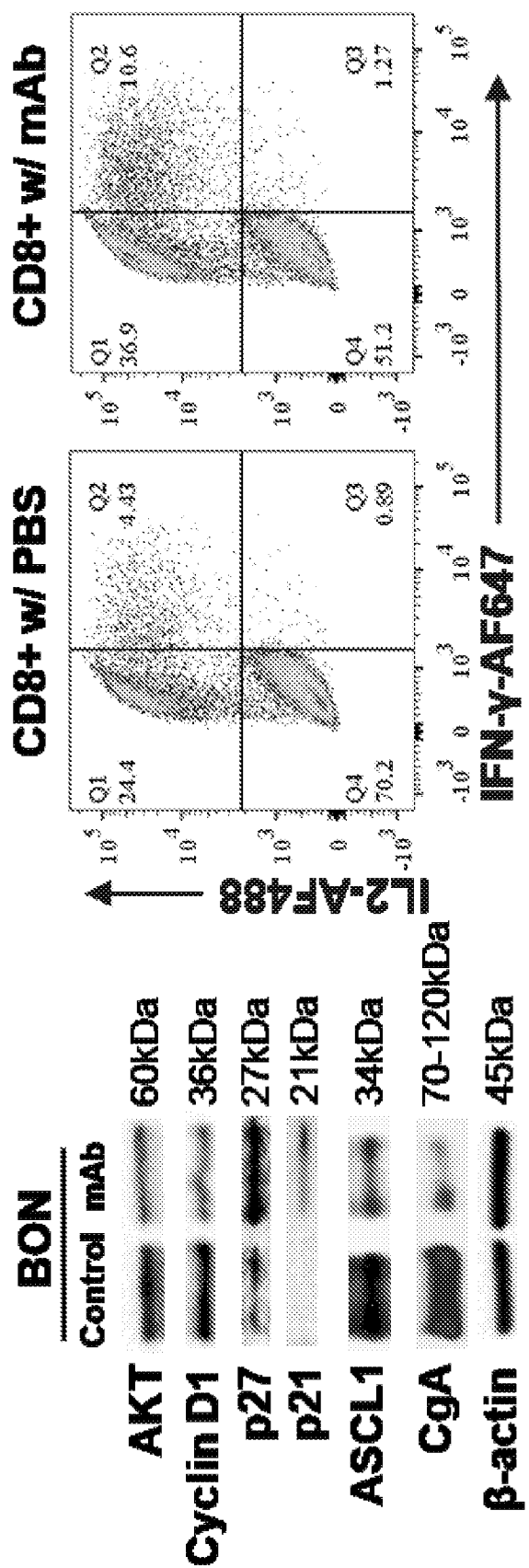
FIGS. 4A and 4B show the anti-SSTR2 mAb mediated anti-NET. (A) Western blot demonstrated that mAb downregulated the expression of PI3K/AKT (cell proliferation), changed the level of cyclin D1 and p21 (cell cycle), and reduced ASCL/CgA (hormone); (B) Flow cytometry analysis revealed that both IL2 and IFNγ (cytokine) of human T cells were increased by mAb.

Evaluate NET specific targeting and anti-NET properties of mAb: The In Vivo Imaging System (IVIS) confirms that the AF488 labeled anti-SSTR2 mAb specifically targets NET subcutaneous xenografts derived from BON-Luc cells (FIG. 3A). The flow cytometry analysis shows that the mAb has very strong surface binding to BON cells (99.7%) (FIG. 3B). Therefore, our novel anti-SSTR2 mAb has great potential as a drug delivery vehicle in the form of ADC. Western blot showed that the mAb downregulates PI3K/AKT (proliferation), Cycline D1 (oncogene) and p21 (cell cycle arrest), and significantly reduces the expression of CgA and ASCL1 (NET markers) (FIG. 4A). Using flow cytometry, we analyze the effect of our SSTR2 mAb on the expression of cytokines in the CD3/CD28 stimulated human CD8+ T cells after incubating with mAb for 2 days. As shown in FIG. 4B, the SSTR2 mAb increased IL2 expression by 1.6 folds and IFNγ by 2.2 folds.

Figure 5A:
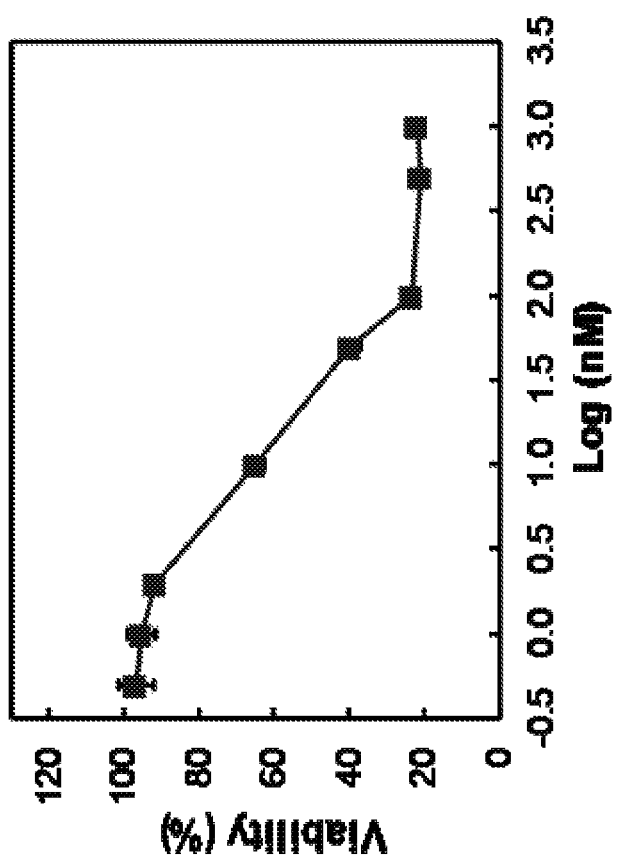
FIGS. 5A to 5B show ADC toxicity. ADC had higher toxicity $IC_{50}$<10 nM for BON cells.
Figure 5B:
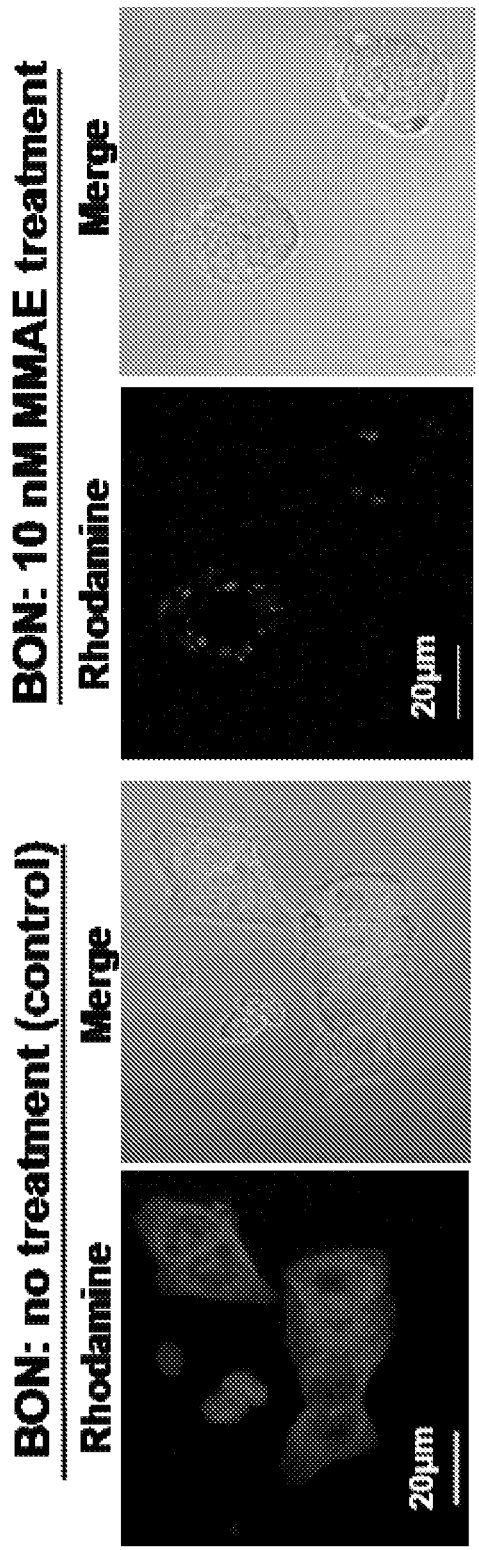

Evaluate anti-NET toxicity of ADC: A 3-day MTT proliferation assay shows that the ADC constructed with in situ rebridging not only retains the structure integrity and biological function of mAb but also has high cytoxicity to NET cells, with $IC_{50}$ of <10 nM for BON (FIG. 5A). We confirm that MMAE inhibited NET cell proliferation by microtubule de-polymerization (FIG. 5B), which in consequence resulted in cell cycle arrest and growth disruption specifically at G2/M transition

Example 4: Characterize the Anticancer Efficacy of ADC In Vivo

Figure 6:
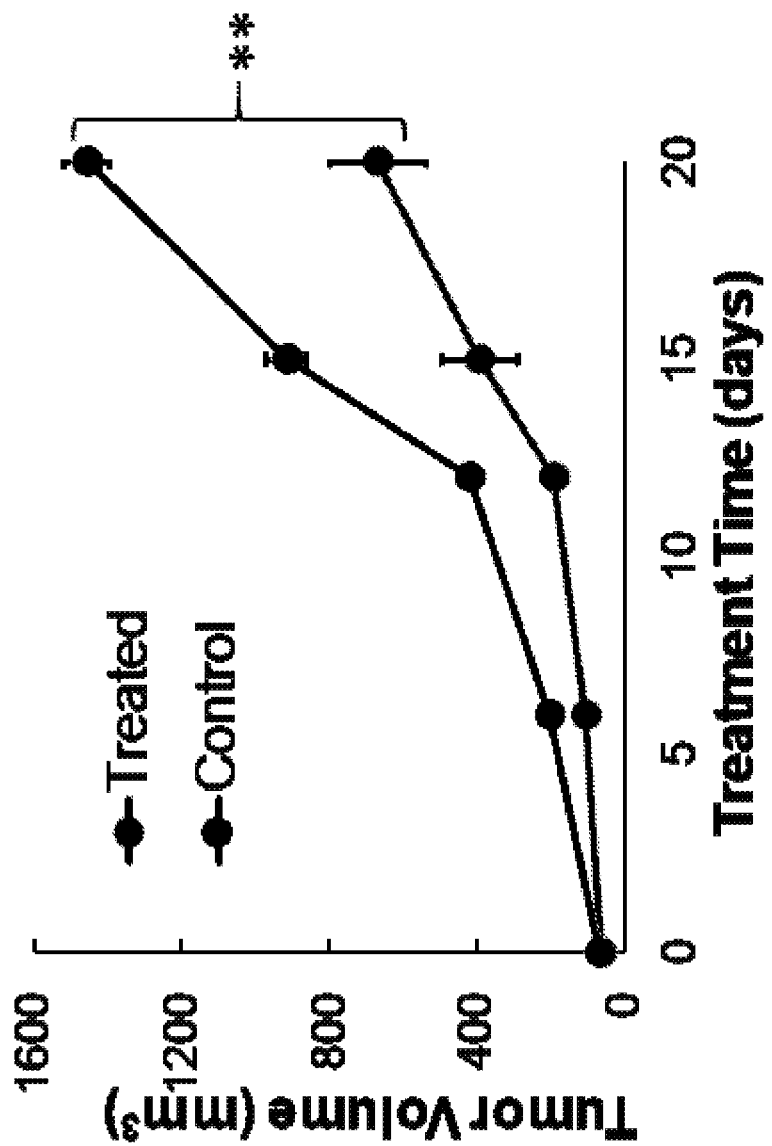
FIG. 6 shows the in vivo anti-cancer efficacy in s.c. xenograft mouse model. Average tumor volume measured by caliper for mice treated with 8 mg/kgBW ADC or vehicle. The error bars represent standard deviation at n=6; p≤0.01; *p≤0.001.

To create a comparable animal model, NET cells are injected subcutaneously into nude mice (i.e., subcutaneous xenografts) and this model is used to investigate the anti-cancer efficacy of ADC. The MTD study showed that the mAb-MMAE treatment with a dose of ≥20 mg/kgBW did not cause any significant changes in body weight or survival. The anti-cancer study with dose of 8 mg/kgBW shows ~60% reduction in tumor volume compared to saline treated controls (FIG. 6). Moreover, pathological assessment of H&E-stained sections of different organs (liver, brain, heart and leg) of treated mice does not indicate any signs of acute or chronic inflammation, or apoptotic and necrotic regions, suggesting that this therapy is safe for organs other than NET nodules and potential off-target uptake of ADC by normal tissues does not cause detectable damage.

Example 5: Antibody-Drug Conjugate for Neuroendocrine Cancer Therapy

Neuroendocrine (NE) cancers include a diverse spectrum of hormone-secreting neoplasms that arise from the endocrine and nervous systems. Current chemo- and radio-therapies have marginal curative benefits. This study aimed to develop an innovative antibody-drug conjugate (ADC) to effectively treat NE tumors (NETs).

Methods

NET patient tissue microarray (TMA) to analyze receptor expression. A tissue microarray was prepared by the university Research Pathology Core. Patient tissues were obtained from the university Surgical Oncology Tumor Bank through an Institutional Review Board (IRB) approved protocol. The TMA consisted of thirty-eight pancreatic neuroendocrine patient tissue cores and five negative control cores including tissues from the liver, spleen, placenta, prostate, and tonsil. All tissues were paraffin-embedded.

Multiple human organ normal tissue array to analyze SSTR2 distribution. The 33 organs tissue microarray slides (Catalog#: FDA662a) were purchased from US Biomax (Rockville, MD). IHC straining (procedure was described in details in the following section) was performed to analyze the cell surface SSTR2 expression in these organs. The 33 organs are cerebrum, cerebellum, peripheral nerve, adrenal gland, thyroid gland, spleen, thymus, bone marrow, lymph node, tonsil, pancreas, liver, esophagus, stomach, small intestine, colon, lung, salivary, pharynx, kidney, bladder, testis, prostate, penis, ovary, uterine tube, breast, endometrium, cervix, cardiac muscle, skeletal muscle, mesothelium, and skin. As positive control, NET patient tissues were also stained at the same conditions using our developed anti-SSTR2 mAb.

NET cell lines and seed cultures. Multiple human NET cell lines, including BON-1 (pancreatic NET), QGP-1 (pancreatic NET), BON-1 cell line carrying a firefly luciferase reporter gene (BON-Luc), MZ-CRC-1 (thyroid NET), and TT (thyroid NET), were used for in vitro and in vivo studies. The BON-1 and MZ-CRC-1 cell lines were maintained in DMEM/F12 basal medium supplemented with 10% fetal bovine serum (FBS) and 4 mM L-glutamine; the TT cell line was maintained in RPMI-1640 supplemented with 20% FBS and 4 mM L-glutamine. The non-cancerous negative control cell lines, including WI-38 (pulmonary fibroblast) and 917 (foreskin fibroblast), were maintained in MEM-E medium supplemented with 10% FBS, 1% non-essential amino acids, and 1% sodium pyruvate. All cell lines were incubated in either T25 or T75 flasks at 37° C. and 5% $CO_2$ in a humidified incubator (Caron, Marietta, OH). The cell growth, i.e. viable cell density (VCD) and viability, were measured using Countess II automated cell counter ortrypan blue (Thermo Fisher Scientific, Waltham, MA). All basal media, supplements, and reagents used in this study were purchased from Thermo Fisher Scientific or Life Technologies (Part of Fisher) unless otherwise specified.

Hybridoma cell lines and seed cultures. The adherent culture of anti-SSTR2 mAb producing hybridoma clones were maintained in DMEM supplemented with 10% FBS in T flasks, which was used for clone evaluation in flow cytometry and confocal microscopy imaging. To produce large-scale mAb in stirred-tank bioreactor, top four hybridoma clones were adapted from adherent culture to serum-free suspension culture, and cells were cultivated in Hybridoma-SFM medium supplemented with 4 mM L-glutamine and 1% anti-clumping agent (v/v) in shaker flasks at 37° C., 5% $CO_2$ and 130 rpm.

Anti-SSTR2 mAb development. Both human SSTR2 (isoform A, UniProtKB P30874) and mouse SSTR2 (isoform A, UniProtKB P30875) are an integral membrane glycoprotein with the same topology, including four extracellular topological domains, seven helical transmembrane, and four cytoplasmic topological domains. Protein blast analysis showed that the four extracellular domains have similarity of 81%, 100%, 100%, and 90%, respectively. To develop a monoclonal antibody that can target both human and mice SSTR2, we developed an anti-human SSTR2 mAb to target the $1^{st}$ extracellular domain (cQTEPYYDLTSNA, aa 33-44, SEQ ID NO:14) and the $2^{nd}$ extracellular domain (cALVHWPFGKAICRVV, aa 104-118, SEQ ID NO:15) using hybridoma technology. The synthesized antigen peptides were intravenously (i.v.) injected into five balb/c mice for immunization and boosts every two weeks for ten weeks (five injections), which was performed by ProMab following standard protocol. The anti-SSTR2 mAb in the sera collected from the immunized mice, both pre-immune serum and anti-SSTR2 serum, was titrated using antigen peptides-based sandwich enzyme-linked immunosorbent assay (ELISA) and Western blotting. The immune splenocytes from the mouse with the best anti-SSTR2 antibody titer was fused with myeloma cells (Sp2/0) to obtain hybridoma clones.

mAb producing hybridoma clones screening. Total of 100 subclones were generated, cultivated in 96-well plates during the first two stages of screenings. The primary clone screening was performed based on SSTR2 mAb volumetric productivity (i.e. final titer) using mixed double domains of antigen, which generated the top 40 clones. In the secondary screening, the top 4 clones were screened using peptide ($1^{st}$ or $2^{nd}$ extracellular domain)-based ELISA. In the tertiary screening, we adapted the top four clones in serum-free suspensive cultures and performed batch culture in shaker flask. The mAb was purified using Protein A kit and labeled with AF647 following the manufacturing protocol to evaluate cancer surface binding in flow cytometry and confocal microscopy imaging. The lead clone with strong surface binding to NET (BON-1) cells and low binding to non-cancerous H727 control cells was defined for further evaluation and ADC construction.

ELISA. ELISA was used in the early stage immunization and hybridoma clone screening. Briefly, 96-well plates were coated with antigen diluted in 50 mM carbonate at pH 9.6 and incubated overnight at 4° C. The spent medium containing mAb or the purified mAb diluted in blocking buffer was added at 100 μL each well and incubated for 1 hr at room temperature (RT). The anti-SSTR2 mAb was captured and detected by adding 50 μL each well of HRP-labeled anti-mouse IgG (Sigma, St. Louis, MO, Catalog#: RABHRP2-10UL) diluted to 1:10,000 in blocking buffer. The buffer A containing 0.1 M $Na_3C_6H_5O_7 \cdot 2H_2O$ and 1.5% $CH_4N_2O \cdot H_2O_2$ and buffer B containing 3,3',5,5'-tetramethylbenzidine and 0.1 M $C_6H_8O_7 \cdot H_2O$ were used for color development. The plates were read at 450 nm on microplate reader after adding stop solution.

Isotype evaluation. The commercial mouse antibody isotyping kit was used to determine the isotype of the developed mAb. Specifically, the goat anti-mouse IgG, IgA and IgM were used to coat plate. After adding mAb samples, the subclass specific rabbit anti-mouse IgG1, IgG2a, IgG2b, IgG3, IgA, IgM, κ and λ were added. The HRP labeled anti-rabbit IgG and substrate solution were used to develop color.

Anti-SSTR2 mAb production. The lead SSTR2 mAb producing hybridoma clone was maintained in 125-mL shaker flask. The seed train was scaled up to 3-L spinner flask with working volume of 1 L and agitation 80 rpm. The mAb production was performed in a 5-L stirred-tank bioreactor cell culture that was controlled at Temp 37° C., pH 7.0, DO 50% and agitation 70 rpm. Specifically, the batch production culture in bioreactor was seeded with VCD of $0.3$-$0.5 \times 10^6$ cells/mL in Hybridoma-SFM supplemented with 6 g/L glucose, 6 mM L-glutamine, 3.5 g/L Cell Boost #6, and 1% anti-clumping agent. The production cultures were sampled daily to monitor the cell growth (i.e., VCD, viability, double time, and growth rate) using cell counter, glucose using glucose analyser, and mAb production using NGC system (Bio-Rad, Hercules, CA). When viability dropped to around 80%, the spent medium was harvested and clarified using centrifuge and 0.22 µm ultrafiltration for further purification of mAb.

mAb purification. A previously developed protocol of two-step antibody purification (Ou J, et al. PLoS One. 2018 Oct. 23 13(10):e0206246; Xu N, et al. Biochemical Engineering Journal. 2018 145:177-85) using NGC system was used to purify the anti-SSTR2 mAb. Specifically, the primary Protein A affinity purification was performed to capture mAb in a UNOsphere SUPrA column which was equilibrated with a buffer comprised of 0.02 M sodium phosphate and 0.02 M sodium citrate at pH 7.5. After column washing, mAb was eluted with buffer containing 0.02 M sodium citrate and 0.1 M sodium chloride at pH 3.0 and neutralized to 7.0 with 1 M Tris solution. The polishing purification was performed using a cation exchange column Foresight Nuvia S and the mAb was eluted using 20 mM to 200 mM sodium chloride solution. The purified mAb was titrated using NGC and characterized using SDS-PAGE, Western blotting, flow cytometry, and confocal microscope as described in the following sections.

ADC construction. A published platform of cysteine-based conjugation procedure (Ou J, et al. PLoS One. 2018 Oct 23 13(10):e0206246) was used to construct ADC. First, re-bridging linker was synthesized by mixing 6-amino-hexanoic acid with 3,4-dibromofuran-2,5-dione at a 1:1 molar ratio at 60° C. for 30 mins, heated at 100° C. for 18 hrs, and purified by silica gel with 0-40% dichloromethane/ethyl acetate as eluent solution. Second, N,N'-diisopropyl-carbodiimide, N,N-diisopropylethylamine, and rebridging linker were mixed in dichloromethane with a molar ratio of 1:1:2.5 for 1 hr at 25° C. Then identical molarity of MMAE was added and frequently mixed for 16 hrs to synthesize linker-payload which was purified through HPLC system (Waters, Milford, MA) equipped with a reversed-phase C18 column with 5 µm C18(2) 100 Å and 250×10 mm (Phenomenex, Torrance, CA). Third, anti-SSTR2 mAb exchanged to 50 mM borate buffer (pH 8.0) and MMAE were conjugated with molar ratio of 1:7 and purified through PD SpinTrap™ G25 columns (GE Healthcare). Finally, the average drug-antibody ratio (DAR) was calculated as Ratio= $(\varepsilon_{Ab}^{248} - R\varepsilon_{Ab}^{280})/(R\varepsilon_D^{280} - \varepsilon_D^{248})$ where $R = A_{248}/A_{280}$ = Absorbance ratio (Ou J, et al. PLoS One. 2018 Oct 23 13(10):e0206246), and confirmed using liquid chromatography-electrospray ionization-tandem mass spectrometry (LC-ESI-MS).

In vitro anti-cancer toxicity ($IC_{50}$). BON cell line was utilized to compare the toxicity of ADC. 75 uL of culture media containing cells (viability >95%) with a density of $5 \times 10^4$ cells/mL was added in each well of 96-well plate. ADC or MMAE solution was sterilized by 0.2 µm filter and diluted to different concentrations with complete medium. After 4-hr incubation in regular cell culture incubator, 75 µL of ADC or MMAE with gradient concentrations were mixed with cells in the 96-well plate. The well plate was covered by another 96-well plate filled with PBS to prevent medium evaporation during treatment period. After 3-day incubation, the toxicity result was generated through Luminescent Cell Viability Assay (Promega, Madison, MI).

SDS-PAGE and Western blotting. The Mem-PER plus membrane protein extraction kit was used to extract membrane proteins for surface receptor evaluation. The protein concentration was determined by the Pierce BCA assay following manufacturing protocol. Non-reducing SDS-PAGE was run using electrophoresis system with NuPAGE™ 4-12% Bis-Tris protein gels. The gel proteins were electro-transferred to a PVDF membrane and blocked with TBS washing buffer containing 5% fat-free milk powder and 0.1% Tween 20 for 1 hr at RT. The primary rabbit anti-mouse antibody (Abcam, Cambridge, MA, Catalog#: ab190475) with 1:5,000 dilution from 1 mg/mL stock was incubated with the blocked membrane overnight at 4° C., rinsed three times with TBS buffer, and then incubated with HRP-conjugated secondary anti-rabbit antibody (Abcam, catalog#: ab205718)) with dilution of 1:3,000 for 1 hr at RT. Finally the blotted membrane was treated with Luminata Forte Western HRP substrate (Millipore, Boston, MA), imaged with MyECL imager, and quantified with ImageJ software.

Flow cytometry to quantitate surface receptor density and mAb binding. The purified anti-SSTR2 mAb was labelled with an Alexa Fluor™ 647 Antibody Labelling Kit and used to quantitatively evaluate the surface receptor binding capacity to NET cell lines (BON, TT and MZ) and negative control fibroblast cell line (917) using a BD LSRII flow cytometer (BD Biosciences, San Jose, CA). $1 \times 10^6$ cells were harvested from T-flasks when confluence reached 70%, washed with flow cytometry buffer, and incubated with 1 µg AF647 labeled mAb on ice or RT in darkness for 30 mins. After washing three times, the cells were re-suspended in 1 mL of flow cytometer buffer, and analyzed with BD Biosciences' BD LSRII flow cytometer. Gating was set where negative sample has <0.5% fluorescent population. As control, the commercial anti-SSTR2 mAb (RD Systems, Minneapolis, MN, Catalog#: MAB4224) was used in flow cytometry.

Confocal imaging to evaluate ADC binding and internalization. The laminin was coated on glass coverslips (Warner Instruments, Hamden, CT) at a concentration of 10 µg/mL to enhance adhesion efficiency and incubated for 24 hrs at 4° C. The NET cells or negative cells were seeded onto glass cover slips with a density of $5 \times 10^4$ cells/mL in a 24-well plate, and incubated for 4 hrs at 37° C. When cells reached 50% confluence, BacMam GFP Transduction Control was added to transduce cells and incubated overnight, which stain the cytoplasma and nucleus. Next the AF647 labelled mAb was diluted with PBS to a concentration of 2 µg/mL. The coverslips containing transduced cells were then rinsed twice with PBS, transferred to an appropriate micro-incubation stage adapter, and stained with 500 µL of 2 µg/mL AF647-mAb in a PBS buffer containing 10% inactivated goat serum and 1% bovine serum albumin at 37° C. in darkness for 30 mins. The cells were observed using Olympus 1X-81 confocal microscope with Olympus FV-1000 laser scan head using a confocal microscope (Olympus IX81, Center Valley, PA). The MitoSox images were recorded using an Olympus FV1000 confocal microscope to monitor surface binding and internalization of AF647-mAb. A 488 nm laser with 0.2% transmissivity and a PMT voltage of 519 V was used to visualize BacMam infected cells while a 635 nm laser with 31% transmissivity and a PMT voltage of 686 V was used to visualize the fluorescent labeled mAbs. The images were analyzed offline with the ImageJ software.

Xenograft mouse model generation and anti-NET efficacy study. BON-Luc seed culture was tested as mycoplasma-free before scaling up. Cells were concentrated and injected onto the back of each Nude (nu/nu) mice (4-6 weeks of age, male and female) (Jackson Labs) with a density of $1 \times 10^6$ cells/mouse, viability >95%. Tumors were allowed to grow 5 days post-xenograft. Mice with 50~60 mm³ tumor volume were selected for ADC efficacy study. Mice were randomized to 3 groups (n=6): saline, anti-sstr2 mAb, mAb-MMAE conjugate. Treatment started on day 6 post injection: mAb/ADC was administered through tail vein following a dose of 12 mg/kg-BW, 2 injections/week; the same volume of saline was injected in the saline group. The volume of solid tumor and mouse body weight were measured every two days. Four injections were conducted with average injection interval of 4.5 days during the entire treatment period. Mice were sacrificed on Day 28 post-xenograft. Solid tumors and other organs (brain and liver) were collected for imaging and further analysis.

Biodistribution by In Vivo Imaging System (IVIS). Xenograft mouse model was generated using the method above. At the 7$^{th}$ day post-xenograft, mice with 100-150 mm$^3$ solid tumor were selected for mAb bio-distribution study. The anti-SSTR2 mAb was labeled with fluorescent dye using Sulfo-Cyanine5.5 antibody labeling kit (Lumiprobe). After sterilization, 25 μg of Cy5.5-mAb was injected into each mouse through tail vein. Mice were imaged 24 hrs post-injection under in vivo imaging system. Parameter was set up as 660 nm/710 nm (excitation/emission) wavelength.

Pharmacokinetics study. To investigate the metabolic rate of ADC, 5 different concentrations (4, 8, 12, 16, 20 mg/kg-BW) of ADC were injected to 5 groups of randomized mice (n=4). Blood samples were collected from tails at 2, 5, 24, 48, 72, 120 hrs post-injection (6 time points in total). Blood was centrifuged at 2,000 g for 5 mins to precipitate cells and the supernatant was collected for ELISA analysis. Standard sandwich ELISA was used to quantify the ADC remained in mouse plasma. SSTR2 peptide was utilized to coat 96-well plates. Horseradish peroxidase conjugated goat-anti mouse IgG antibody and 3,3',5,5'-Tetramethylbenzidine (TMB) were used for color development. The ADC in plasma was diluted and titrated using ELISA with detection range of 0-300 ng/mL. The recommended dose (D) and dosing interval (τ) were calculated using previously developed PK model (Ref): $D=C_{max(desired)} \cdot k_e \cdot V_d \cdot T \cdot (1-e^{-k e \tau})/(1-e^{-k e T})$ and $\tau=\ln(C_{max(desired)}/C_{min(desired)})/k_e+T$, which were used in the anti-cancer efficacy animal study.

Hematoxylin and eosin (H&E) staining. The section was deparaffinized before staining. 200 μL of hematoxylin solution was added to stain the section, followed by 5-min incubation at 25° C. The dye was washed away by running tap water from reverse side. The section was rinsed in PBS for 5 mins. Then, the section was stained in 400 μL of eosin Y solution for 30 seconds and washed using running tap water. The section was dehydrated in absolute alcohols by two 2-min reactions and cleared in xylene.

Immunohistochemistry (IHC) staining. Formalin-fixed and paraffin-embedded NET tissue were prepared and sectioned by the Tissue-Based Translational Research Lab in the Department of Pathology at UAB. The normal organs TMA was purchased from US, Biomax, Inc. Slides were cleared and rehydrated using xylene and ethanol. Slides were then immersed in citrate buffer (BioGenex, Fermont, CA) for a ten-minute pressure cooker cycle to achieve antigen retrieval. Endogenous peroxidase activity was quenched by incubating slides in 3% hydrogen peroxide for ten minutes. Blocking was performed for 1 hr at RT using 3% goat serum and 0.3% Triton-X100 in PBS. SSTR2 was detected with an overnight 4° C. incubation using 1.8 mg/mL of anti-SSTR2 mAb. An anti-mouse biotin-labeled secondary antibody was used, followed by a 30-min incubation with HRP streptavidin. Slides were stained with DAB Chromogen (Dako Liquid DAB+ substrate K3468) and counter stained with hematoxylin. Before being cover slipped and imaged, slides were dehydrated and cleared using ethanol and xylene.

Statistics. All the data were presented as mean±standard error of the mean (SEM). Two-tailed Student's t tests were used to determine the significance between two groups. Comparison among multiple groups was performed using a one-way ANOVA followed by post-hoc (Dunnett's) analysis. The sample size of animal study was determined by prior study and published ADC therapy study (68). The statistical significance with ***P value of <0.001 was considered for all tests.

Study approval. The tumor tissue samples from NET patients were obtained from the UAB Surgical Oncology Tumor Bank through an Institutional Review Board (IRB) approved protocol. Information identifying patient was replaced with sequentially assigned numbers. The normal human organs tissue away was purchased from US Biomax, Inc. Animal studies were conducted in compliance with the Guidelines for the Care and Use of Research Animals established by the UAB IACUC (IACUC-20422).

Results

Figure 7A:
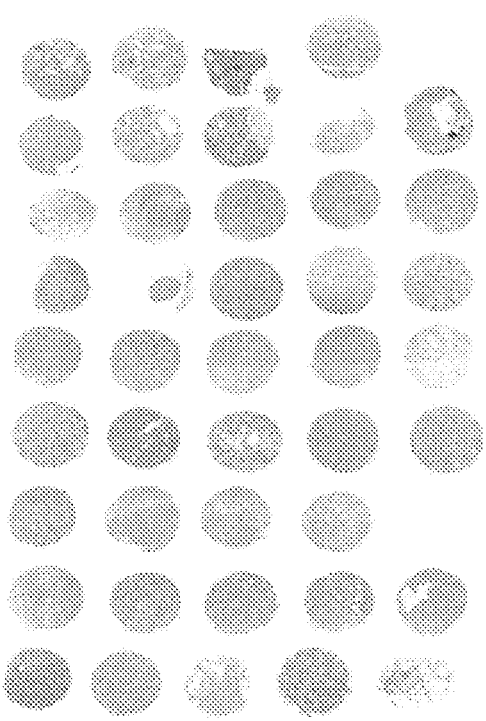
FIGS. 7A and 7B are tissue microarray (TMA) showing strong SSTR2 expression in patients.
Figure 7A:
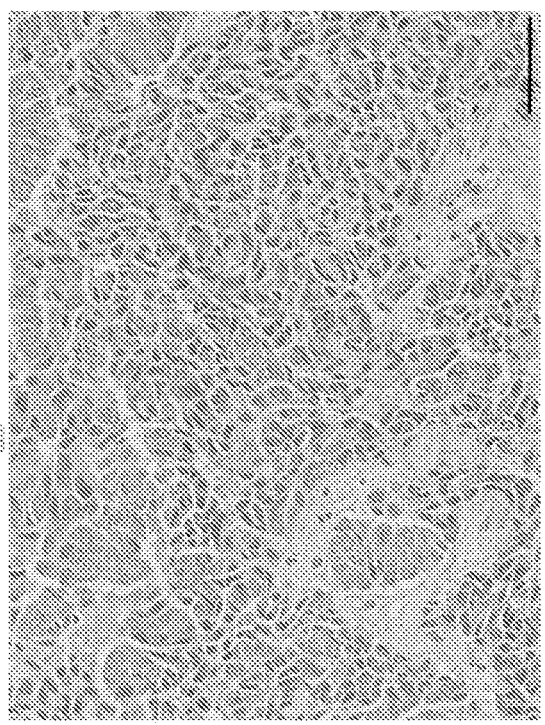
Figure 7B:
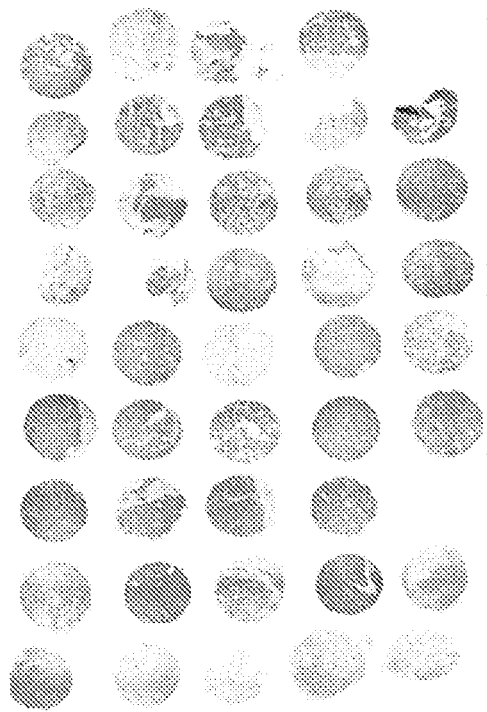
Figure 7B:
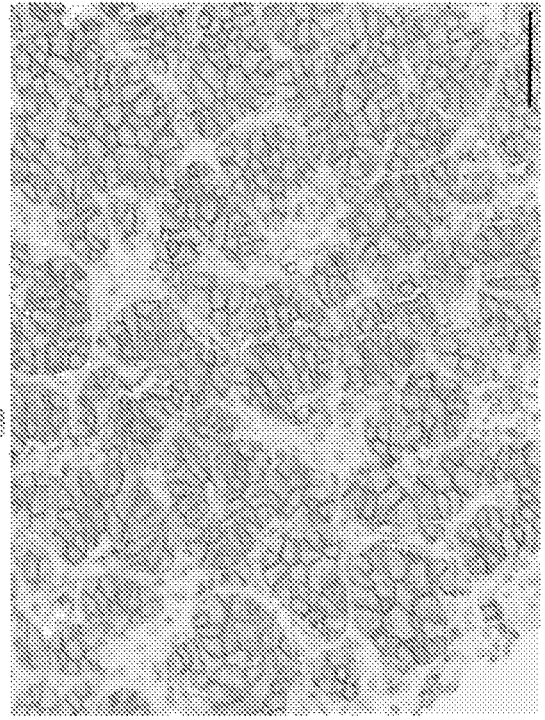

SSTR2 is overexpressed in NET patient tumor tissues, but not in normal organs. To evaluate the expression level of SSTR2 on the cell surface of NET tissues of patients, an immunohistochemical (IHC) staining analysis was performed on a tissue microarray (TMA). The TMA consisted of 38 formalin-fixed, paraffin-embedded cores of pancreatic NETs from different patients (columns 2-9 in FIG. 7), and 5 cores of normal, non-cancerous tissues, including spleen, liver, prostate, placenta and tonsil, as negative controls (column 1 in FIG. 7). The TMA was first stained using hematoxylin and eosin (H&E) which indicated the presence and location of the NET cells in each core (FIG. 7A). The IHC staining demonstrated that approximately 71% of the patient cores were positive for SSTR2 with strong cell membrane localization (FIG. 7B). Furthermore, the expression of SSTR2 was seen exclusively in the NET tissues, but not detectable in the 5 normal tissues.

Figure 8B:
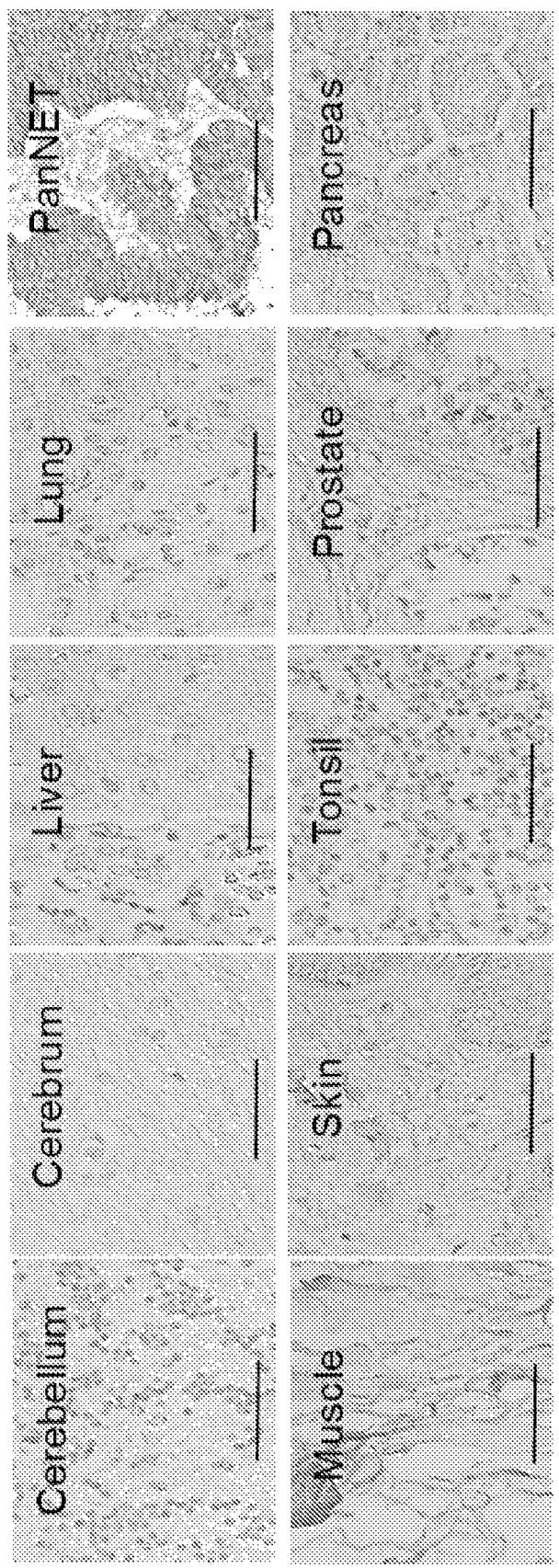

The Human Atlas Project database reported a high level of SSTR2 mRNA in the brain, lung, liver, muscles, skin, placenta, prostate, tonsil, and pancreas. A high-level mRNA does not always correlate to a high expression of protein while the surface expression of SSTR2 is more important to develop targeted therapy. Therefore, the protein expression of SSTR2 in these normal tissues and other normal tissues was investigated with IHC staining using an anti-SSTR2 mAb. A commercial multiple-organ TMA (US Biomax, FDA662a, frozen samples) was used in IHC staining, which contains 33 types of normal human tissues, including cerebrum, cerebellum, peripheral nerve, adrenal gland, thyroid gland, spleen, thymus, bone marrow, lymph node, tonsil, pancreas, liver, esophagus, stomach, small intestine, colon, lung, salivary, pharynx, kidney, bladder, testis, prostate, penis, ovary, uterine tube, breast, endometrium, cervix, cardiac muscle, skeletal muscle, mesothelium, and skin. As illustrated in FIGS. 8A, there is no detectable SSTR2 expression in most normal human tissues except pancreas and skin showing weak positive signal (FIG. 8A and Table 1). The high-resolution images of brain, liver, lung, muscle, skin, tonsil, prostate, and pancreas in FIG. 8B clearly show the minimal or undetectable surface SSTR2 receptor. As a positive control, the NET patient tissues showed positive and strong signal using our mAb compared to the normal tissues.

TABLE 1

Summary of the surface binding of anti-SSTR2 mAb to 33 normal human organ tissues.

| Position | No. | Age | Sex | Organ | Pathology diagnosis | Type | SSTR2 Staining |
|---|---|---|---|---|---|---|---|
| A1 | 1 | 35 | M | Cerebrum | Cerebrum tissue | Normal | − |
| A2 | 2 | 24 | F | Cerebellum | Cerebellum tissue | Normal | − |
| A3 | 3 | 31 | M | Nerve | Peripheral nerve tissue | Normal | − |
| A4 | 4 | 43 | M | Adrenal gland | Adrenal gland tissue | Normal | − |
| A5 | 5 | 44 | F | Thyroid | Adjacent normal thyroid gland tissue | NAT | − |
| A6 | 6 | 21 | F | Spleen | Spleen tissue | Normal | − |
| A7 | 7 | 42 | M | Thymus gland | Thymus gland tissue | Normal | − |
| A8 | 8 | 21 | F | Bone marrow | Bone marrow tissue | Normal | − |
| A9 | 9 | 25 | M | Lymph node | lymph node tissue and fibrovascular tissue | Normal | − |
| A10 | 10 | 28 | M | Tonsil | Tonsil tissue | Normal | − |
| A11 | 11 | 35 | F | Pancreas | Pancreas tissue | Normal | ± |
| B1 | 12 | 24 | F | Cerebrum | Cerebrum tissue | Normal | − |
| B2 | 13 | 35 | M | Cerebellum | Cerebellum tissue | Normal | − |
| B3 | 14 | 18 | F | Nerve | Peripheral nerve tissue | Normal | − |
| B4 | 15 | 18 | F | Adrenal gland | Adrenal gland tissue | Normal | − |
| B5 | 16 | 50 | M | Thyroid | Thyroid gland tissue | Normal | − |
| B6 | 17 | 35 | M | Spleen | Spleen tissue | Normal | − |
| B7 | 18 | 16 | M | Thymus gland | Thymus gland tissue | Normal | − |
| B8 | 19 | 33 | M | Bone marrow | Bone marrow tissue | Normal | − |
| B9 | 20 | 40 | M | Lymph node | lymph node tissue | Normal | − |
| B10 | 21 | 21 | F | Tonsil | Tonsil tissue | Normal | − |
| B11 | 22 | 50 | M | Pancreas | Pancreas tissue | Normal | ± |
| C1 | 23 | 56 | F | Liver | Adjacent normal liver tissue | NAT | − |
| C2 | 24 | 15 | F | Esophagus | Esophagus tissue | Normal | − |
| C3 | 25 | 38 | M | Stomach | Stomach tissue | Normal | − |
| C4 | 26 | 35 | M | Small intestine | Small intestine tissue | Normal | − |
| C5 | 27 | 35 | M | Colon | Colon tissue | Normal | − |
| C6 | 28 | 35 | M | Lung | Lung tissue | Normal | − |
| C7 | 29 | 45 | M | Salivary gland | Salivary gland tissue | Normal | − |
| C8 | 30 | 62 | M | Larynx | Larynx tissue | AT | − |
| C9 | 31 | 47 | M | Kidney | Kidney tissue | Normal | − |
| C10 | 32 | 22 | M | Bladder | Bladder tissue | Normal | − |
| C11 | 33 | 28 | M | Testis | Testis tissue | Normal | − |
| D1 | 34 | 38 | M | Liver | Liver tissue | Normal | − |
| D2 | 35 | 45 | M | Esophagus | Esophagus tissue | Normal | − |
| D3 | 36 | 50 | M | Stomach | Stomach tissue | Normal | − |
| D4 | 37 | 25 | M | Small intestine | Small intestine tissue | Normal | − |
| D5 | 38 | 35 | M | Colon | Colon tissue | Normal | − |
| D6 | 39 | 48 | M | Lung | Lung tissue | Normal | − |
| D7 | 40 | 54 | F | Salivary gland | Adjacent normal salivary gland tissue | NAT | − |
| D8 | 41 | 43 | M | Larynx | Pharynx tissue | Normal | − |
| D9 | 42 | 38 | M | Kidney | Kidney tissue | Normal | − |
| D10 | 43 | 50 | M | Bladder | Bladder tissue | Normal | − |
| D11 | 44 | 30 | M | Testis | Testis tissue | Normal | − |
| E1 | 45 | 31 | M | Prostate | Prostate tissue | Normal | − |
| E2 | 46 | 35 | M | Penis | Penis tissue | Normal | − |
| E3 | 47 | 53 | F | Ovary | Adjacent normal ovary tissue | NAT | − |
| E4 | 48 | 41 | F | Uterine tube | Uterine tube tissue | Normal | − |
| E5 | 49 | 38 | F | Breast | Cancer adjacent breast tissue | AT | − |
| E6 | 50 | 21 | F | Uterus | Endometrial tissue | Normal | − |
| E7 | 51 | 47 | F | Cervix | Cervical tissue | AT | − |
| E8 | 52 | 45 | M | Heart | Cardiac muscle tissue | Normal | − |
| E9 | 53 | 76 | F | Eye | Adjacent normal choroidal tissue | NAT | − |
| E10 | 54 | 42 | F | Striated muscle | Mesothelium and skeletal muscle tissue | Normal | − |
| E11 | 55 | 0.21 | M | Skin | Skin tissue of scalp | Normal | ± |
| F1 | 56 | 43 | M | Prostate | Prostate tissue | Normal | − |
| F2 | 57 | 71 | M | Penis | Cancer adjacent penis tissue | AT | − |
| F3 | 58 | 36 | F | Ovary | Ovary tissue | Normal | − |
| F4 | 59 | 15 | F | Uterine tube | Uterine tube tissue | Normal | − |
| F5 | 60 | 30 | F | Breast | Breast tissue | AT | − |
| F6 | 61 | 40 | F | Uterus | Endometrial tissue | Normal | − |
| F7 | 62 | 47 | F | Cervix | Cervical tissue | Normal | − |
| F8 | 63 | 35 | M | Heart | Cardiac muscle tissue | Normal | − |
| F9 | 64 | 63 | M | Eye | Skeletal muscle tissue | NAT | − |
| F10 | 65 | 33 | M | Lung | Mesothelium and lung tissue | Normal | − |
| F11 | 66 | 18 | F | Skin | Skin tissue of scalp | Normal | ± |

Figure 15A:
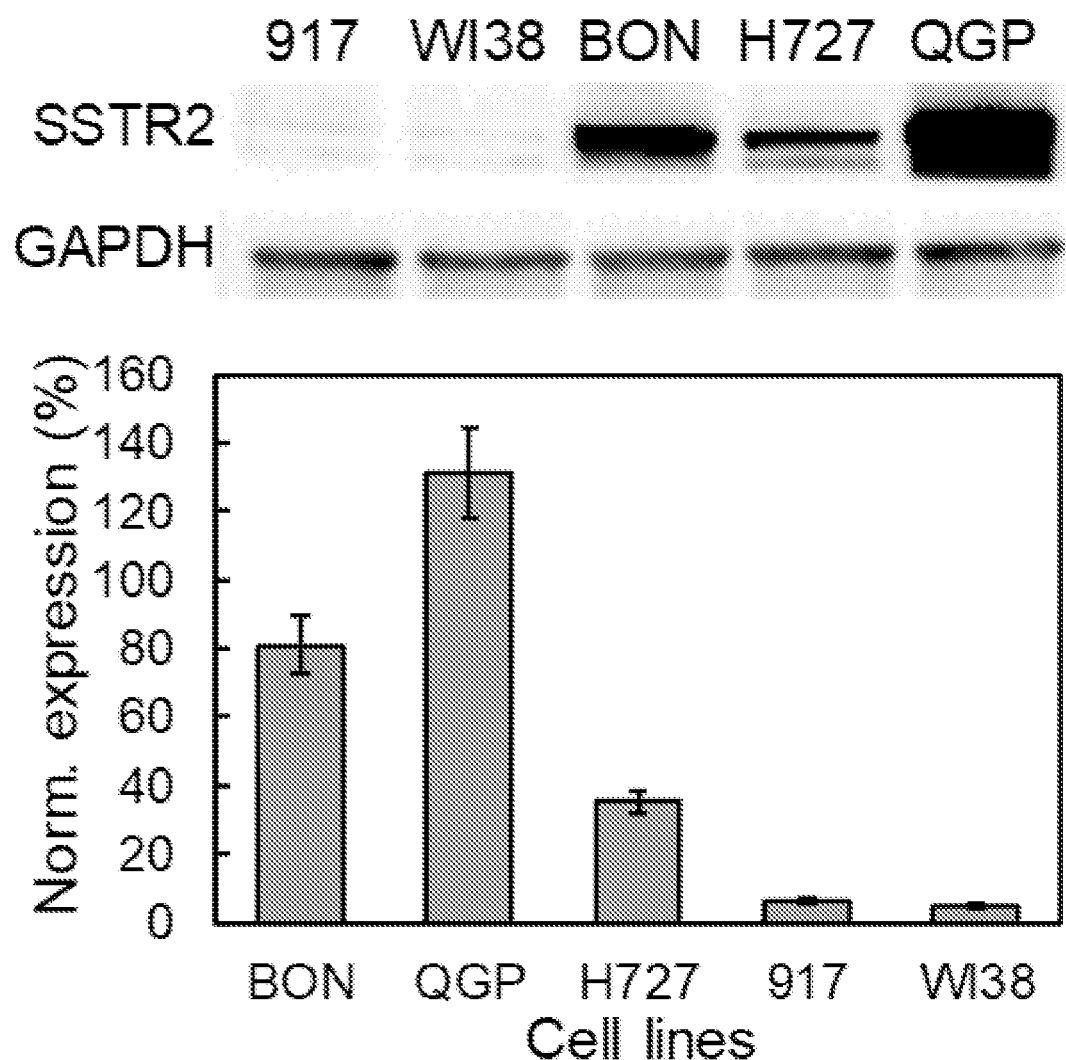
FIGS. 15A and 15B show evaluation of SSTR2 expression in (FIG. 15A) NET cell lines (BON, H727 and QGP) and normal cell lines (917 and WI38) using Western blotting and (FIG. 15B) PanNET xenograft tumor tissues and patient tumor tissue using confocal microscope imaging. Scale bar equals to 20 or 40 μm.
Figure 15B:
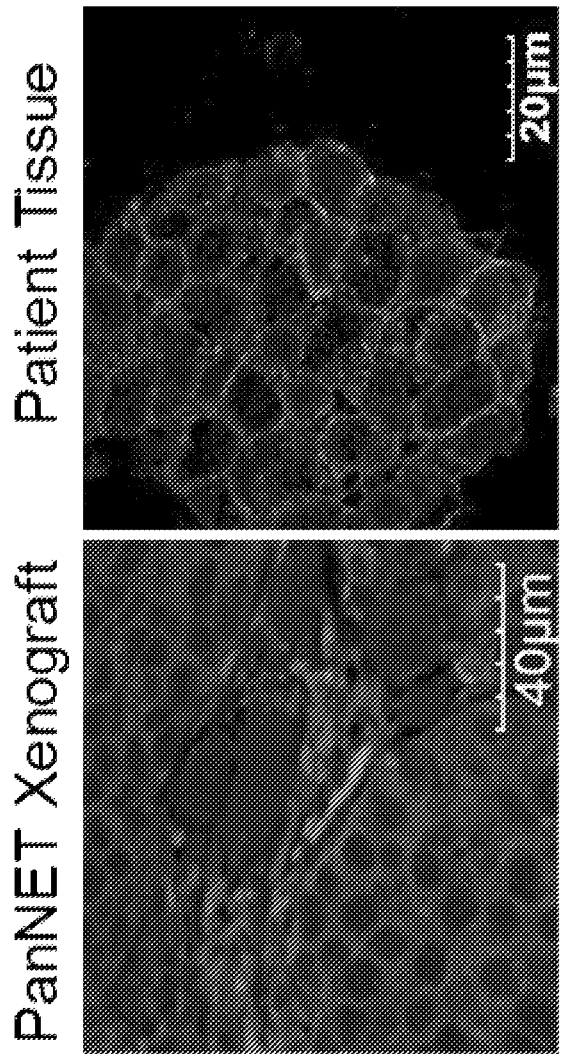

Furthermore, the high level of SSTR2 expression was also confirmed in NET cell lines. The quantitative Western blotting analysis showed a high-level expression of SSTR2 in two pancreatic NET cell lines (BON-1 and QGP-1) and a pulmonary NET cell line (H727), but there was minimal expression in non-cancerous, fibroblast cell lines (917 and WI-38) (FIG. 15A). Moreover, confocal laser scanning microscopy (CLSM) also revealed strong membrane positivity of SSTR2 in both BON-1 xenografts and NET patient tissues (FIG. 15B). All the data collected from patient tumor tissues, normal organs, and cell lines suggest that SSTR2 is an ideal target for NET therapy.

Figure 9A:
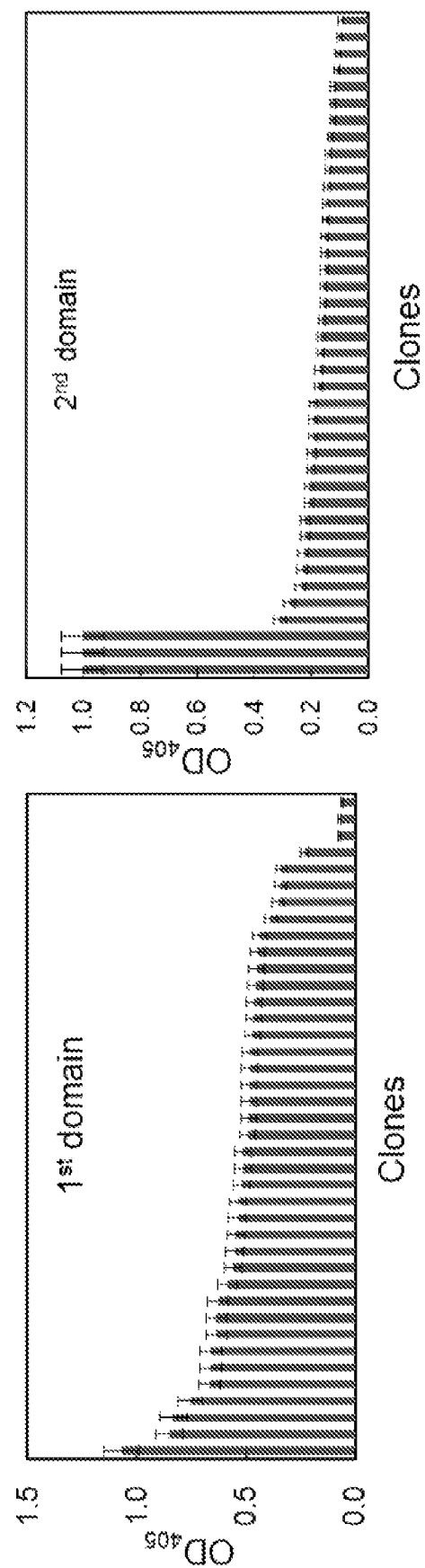

Anti-SSTR2 mAb to target NETs. To effectively target the surface receptor SSTR2 in NETs, a mouse anti-human SSTR2 mAb targeting the $1^{st}$ extracellular domain (cQTEPYYDLTSNA, aa 33-44, SEQ ID NO:14) and $2^{nd}$ extracellular domain (cALVHWPFGKAICRVV, aa 104-118, SEQ ID NO:15) was developed using hybridoma technology. The anti-SSTR2 mAb-producing hybridoma subclones were first screened based on antibody titer using enzyme-linked immunosorbent assays (ELISA). The top 40 clones were ranked based on mAb's binding efficiency to the $1^{st}$ domain and $2^{nd}$ domain of SSTR2 (FIG. 9A). Four clones were selected for further evaluation, including Clone 1 that had the strongest binding to the $2^{nd}$ domain, but had low binding to the $1^{st}$ domain; Clone 2 which had the highest binding to the $1^{st}$ domain but low binding to the $2^{nd}$ domain; and Clones 3 and 4 that had high binding to both the $1^{st}$ and $2^{nd}$ extracellular domains.

The anti-SSTR2 mAbs produced by these 4 clones were further evaluated by testing their surface binding to NET cell lines. An isotype analysis showed that Clones 1-4 are IgG1 kappa, IgG2a kappa, IgG1 kappa, and IgG1 kappa, respectively. To define the lead clone, the capacity of each mAb's binding capacity to the SSTR2 in BON-1 cells was compared and ranked using flow cytometry. As shown in FIG.

9B, the surface binding percentage of Clones 1-4 was 50%, 80%, 90% and 98%, respectively. A sodium dodecyl sulfate polyacrylamide gel electrophoresis (SDS-PAGE) analysis confirmed that the corresponding anti-SSTR2 mAbs produced from these four clones have a molecular weight around 150 kDa (FIG. 9C). Based on the results of mAb expression and SSTR2-specific binding capability, Clone 4 was selected as the best clone and therefore defined as "lead clone". As presented in FIG. 9D, further evaluation showed that the lead anti-SSTR2 mAb had high surface binding to NET cell lines BON-1 and QGP-1 (>90%) and low binding to fibroblast cell lines 917 and WI-38 (<7.5%). Therefore, this lead hybridoma clone was used throughout the remainder of this study for a large-scale mAb production and ADC construction.

Figures 9E, 9F:
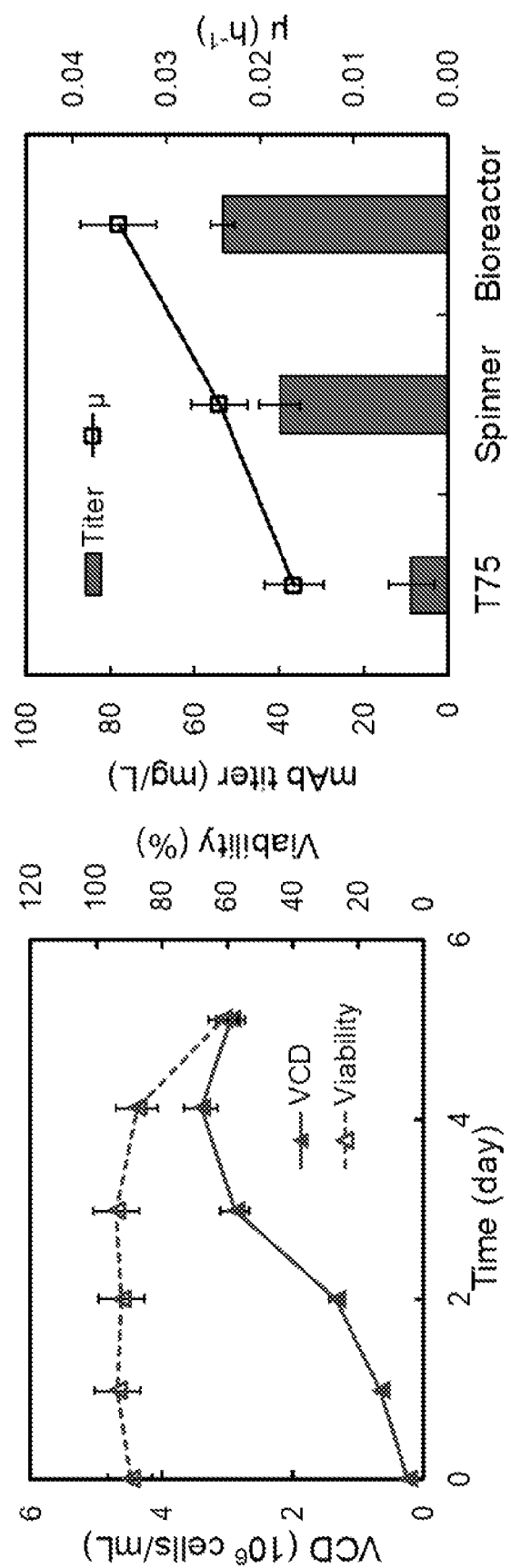

To optimally scale up and produce a high-quality anti-SSTR2 mAb, we adapted the hybridoma cells from adherent culture in T-flask to suspension culture in spinner flask and stirred-tank bioreactor. The mAb production was performed in Gibco Hybridoma-SFM medium supplemented with 6 g/L glucose, 6 mM L-glutamine, 3.5 g/L Cell Boost #6, and 1% anti-clumping agent (v/v) (FIG. 9E). The cultures in T-flask, spinner flask, and stirred-tank bioreactor generated 8.6, 39.8, and 53.3 mg/L of anti-SSTR2 mAb with a specific growth rate of 0.016, 0.024 and 0.035 $h^{-1}$, respectively (FIG. 9F). The anti-SSTR2 mAb was purified following our previously reported procedure (Ou J, et al. PLoS One. 2018 Oct. 23 13(10):e0206246; Xu N, et al. Biochemical Engineering Journal. 2018 145:177-85).

Figure 10A:
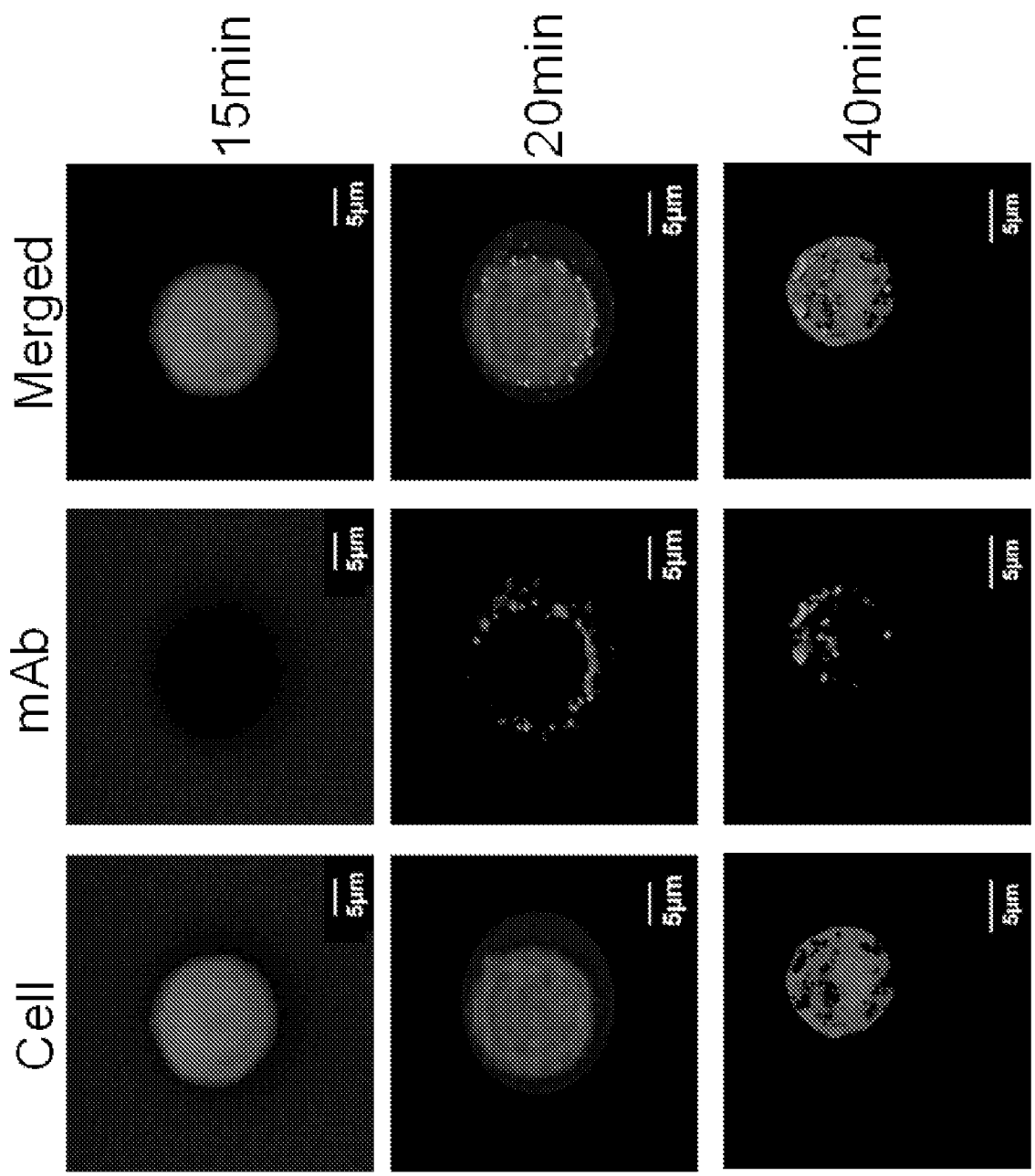
FIGS. 10A to 10C show in vitro evaluation of surface binding by our anti-SSTR2 mAb.
Figure 10B:
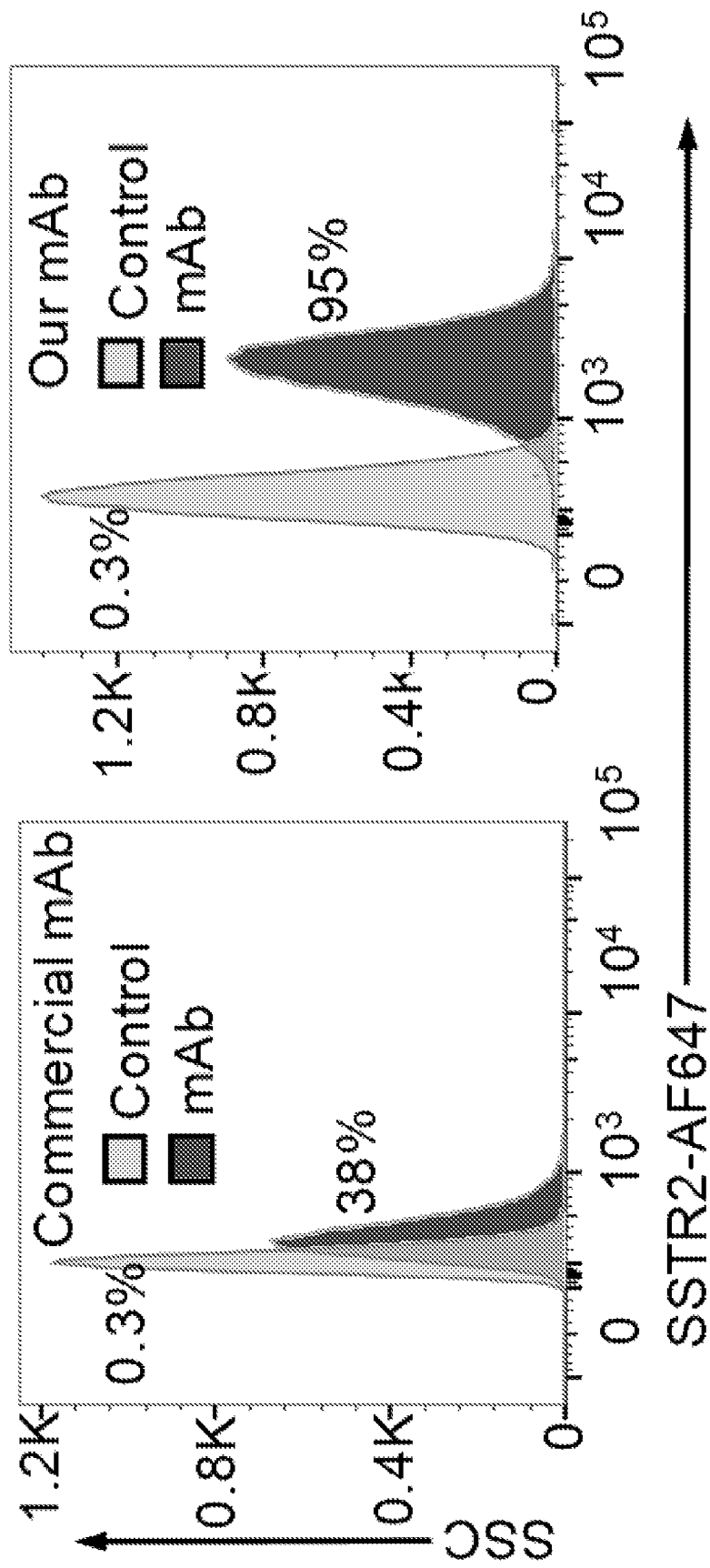
Figure 10C:
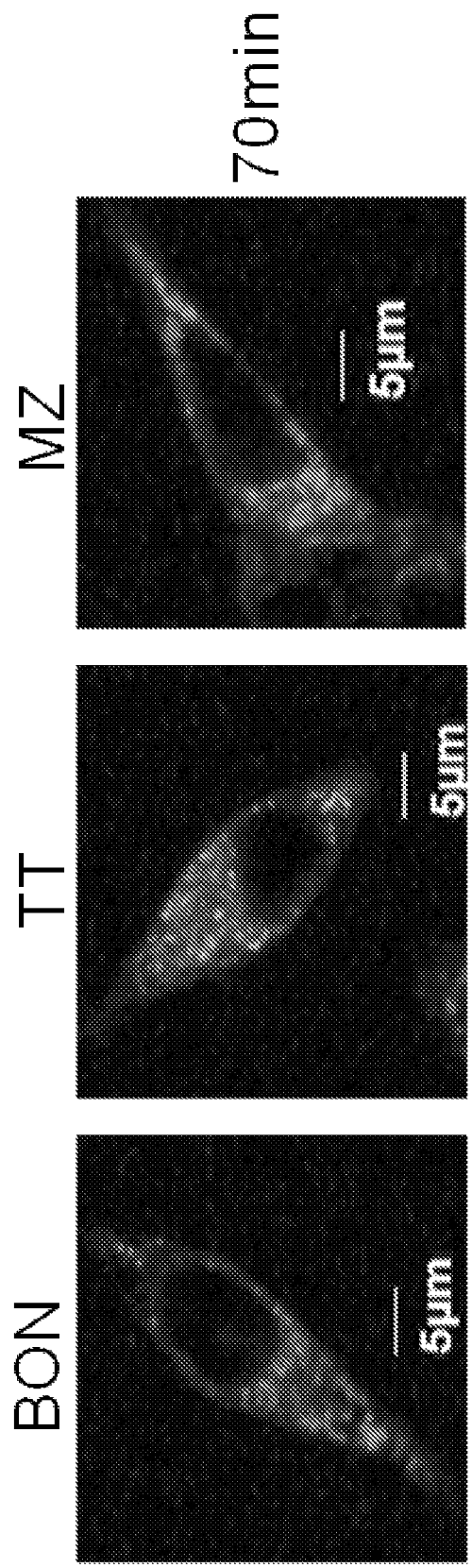

Anti-SSTR2 mAb showed high surface binding to NETs both in vitro and in vivo. To assess the in vitro NET-specific targeting of the anti-SSTR2 mAb to SSTR2, dynamic live-cell CLSM imaging and flow cytometry was performed using NET cell lines. To visualize and track the surface binding process, BON-1 cells were transfected with Bac-Mam GFP control and an Alexa Fluor 647 dye (AF647, labeled as red color, ex./em. 650/665 nm) was conjugated to the anti-SSTR2 mAb. As shown in FIG. 10A, the anti-SSTR2 mAb accumulated on the BON-1 cell surface due to the immunoaffinity, displayed as a "circle", at 20 mins after incubating mAb with cells. The mAb was then internalized by endocytosis and localized in cytoplasm within 40 mins. The surface binding capability of the developed mAb versus a commercially available mAb (R&D Systems) was also compared using flow cytometry. As described in FIG. 10B, the mAb developed in this study had much stronger surface binding to BON-1 cells as compared to the commercial mAb, 95% vs. 38%, under the same staining conditions. In addition, the confocal imaging showed that the anti-SSTR2 mAb bound to and was completely internalized by PanNET cell line (BON-1) and MTC cell lines (TT and MZ-CRC-1) within 70 mins post-incubation (FIG. 10C).

Figures 11A, 11B:
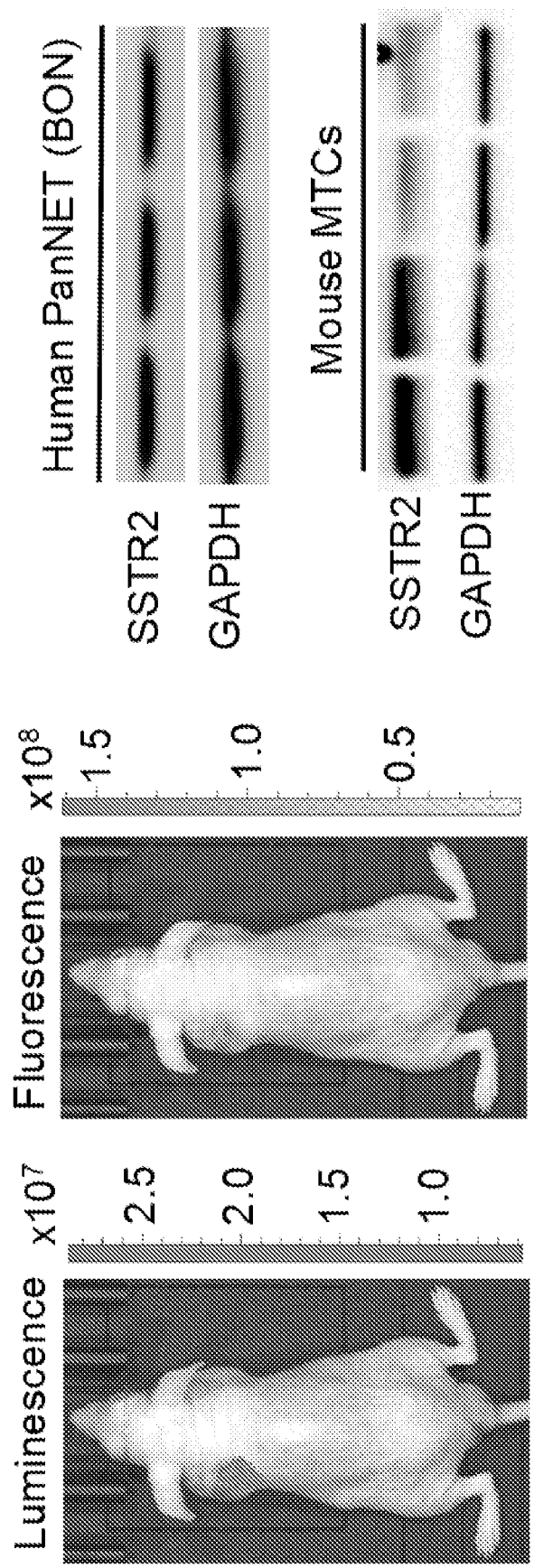
FIGS. 11A and 11B shows in vivo evaluation of NET targeting by our anti-SSTR2 mAb.

Furthermore, the in vivo targeting capability of the anti-SSTR2 mAb was evaluated using NET xenografted mouse model. The mouse model bearing BON-1-Luc cells transfected with firefly luciferase, a bioluminescent reporter. IVIS imaging at 4-8 hrs post-mAb injection indicated a strong accumulation of Cy7-mAb in the BON-Luc xenografts, but there was also a marginal amount of mAb remaining in the murine circulation system. Imaging at 24 hrs demonstrated complete co-localization of the bioluminescent signal from the BON-Luc xenografts and the fluorescent signal from the Cy7-mAb (FIG. 11A). The BON-Luc xenograft, liver, and brain were collected and sectioned to test the mAb binding using CLSM. It is found that there was no detectable non-specific binding of Cy7-mAb to liver or brain, but there was a strong fluorescent signal detected on a section of the BON-Luc xenograft. Altogether, both in vitro and in vivo studies conducted herein have confirmed that the developed anti-SSTR2 mAb can target the SSTR2-overexpressing NET cell lines, xenografts, and patient tissues. Therefore, it is evident that the new mAb has the potential to target and deliver highly potent small molecules in the form of an ADC.

Anti-SSTR2 mAb detects both human and mouse SSTR2. In humans, SSTR2 is endogenously expressed on the cell membrane as a glycoprotein with four extracellular domains, seven helical transmembrane domains, and four cytoplasmic domains (Yamada Y, et al. Proc Natl Acad Sci U S A. 1992 89(1):251-5; Petersenn S, et al. Mol Cell Endocrinol. 1999 157(1-2):75-85; Ota T, et al. Nat Genet. 2004 36(1):40-5). As summarized in Table 2, the UniProtKB database showed that isoform A of human SSTR2 (UniProt P30874) and mouse SSTR2 (UniProt P30875) have the same topology. The disclosed mouse anti-human SSTR2 mAb was generated using the $1^{st}$ and $2^{nd}$ extracellular domains from the human SSTR2, that both have 100% similarity with mouse SSTR2. With this design, it was expected that the disclosed anti-SSTR2 mAb can detect both human and mouse SSTR2. To test this hypothesis, Western blotting was performed, showing that the disclosed anti-SSTR2 mAb can detect SSTR2 present in BON-1 xenografts and in isolated medullary thyroid carcinoma (MTC) cells from a spontaneous MTC mouse model (FIG. 11C). This MTC model was previously developed as the first reliable and clinically accurate conditional MTC mouse model (Pozo K, et al. Cancer Cell. 2013 24(4):499-511; Pozo K, et al. Oncotarget. 2015 6(14):12080-93). The bi-transgenic mouse line was engineered to allow doxycycline dependent repression of p25 (p25OE) under the control of neural specific enolase (NSE) promoter. This study showed that the anti-SSTR2 mAb can detect both human and mouse SSTR2 receptor.

TABLE 2

Anti-SSTR2 mAb targeted 1st and 2nd domains of human SSTR2 and mouse SSTR2.

| SSTR2 surface receptor | Human sequence | Mouse sequence | Similarity (c/o) |
|---|---|---|---|
| $1^{st}$ Extra. domain (33-44) | QTEPYYDLTSNA (SEQ ID NO: 16) | QTEPYYDLTSNA (SEQ ID NO: 16) | 100 |
| $2^{nd}$ Extra. domain (104-118) | ALVHWPFGKAICRVV (SEQ ID NO: 17) | ALVHWPFGKAICRVV (SEQ ID NO: 17) | 100 |

Figure 12A:
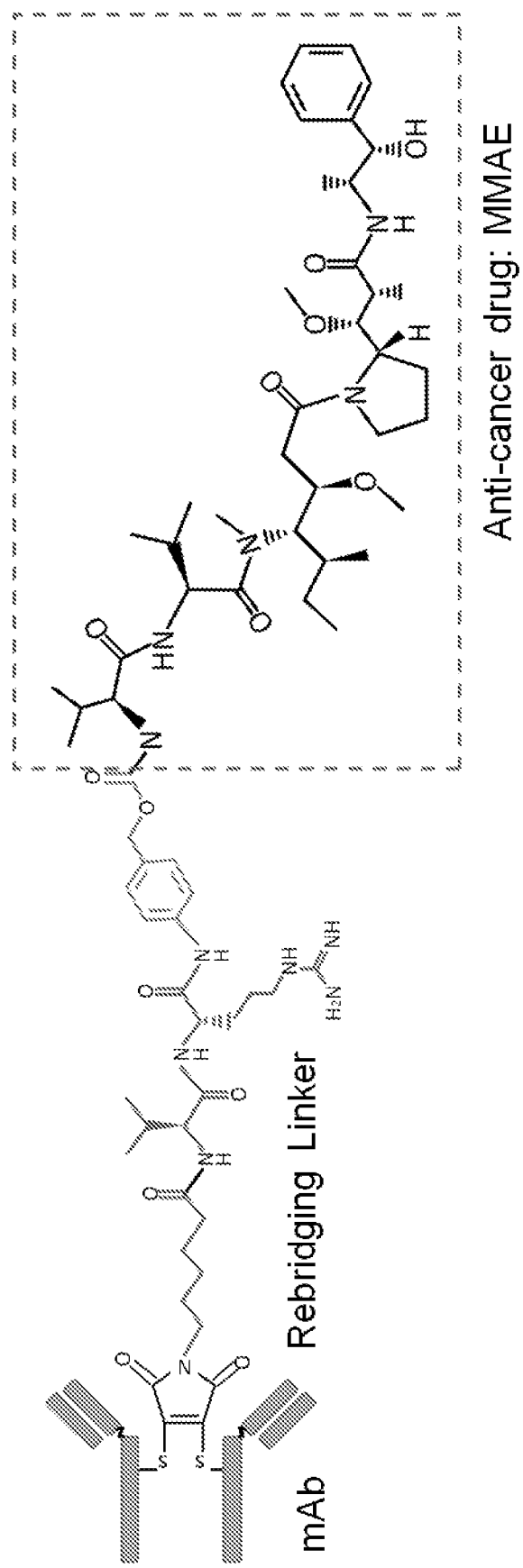
FIGS. 12A to 12F show ADC construction and in vitro characterization.
Figure 12B:
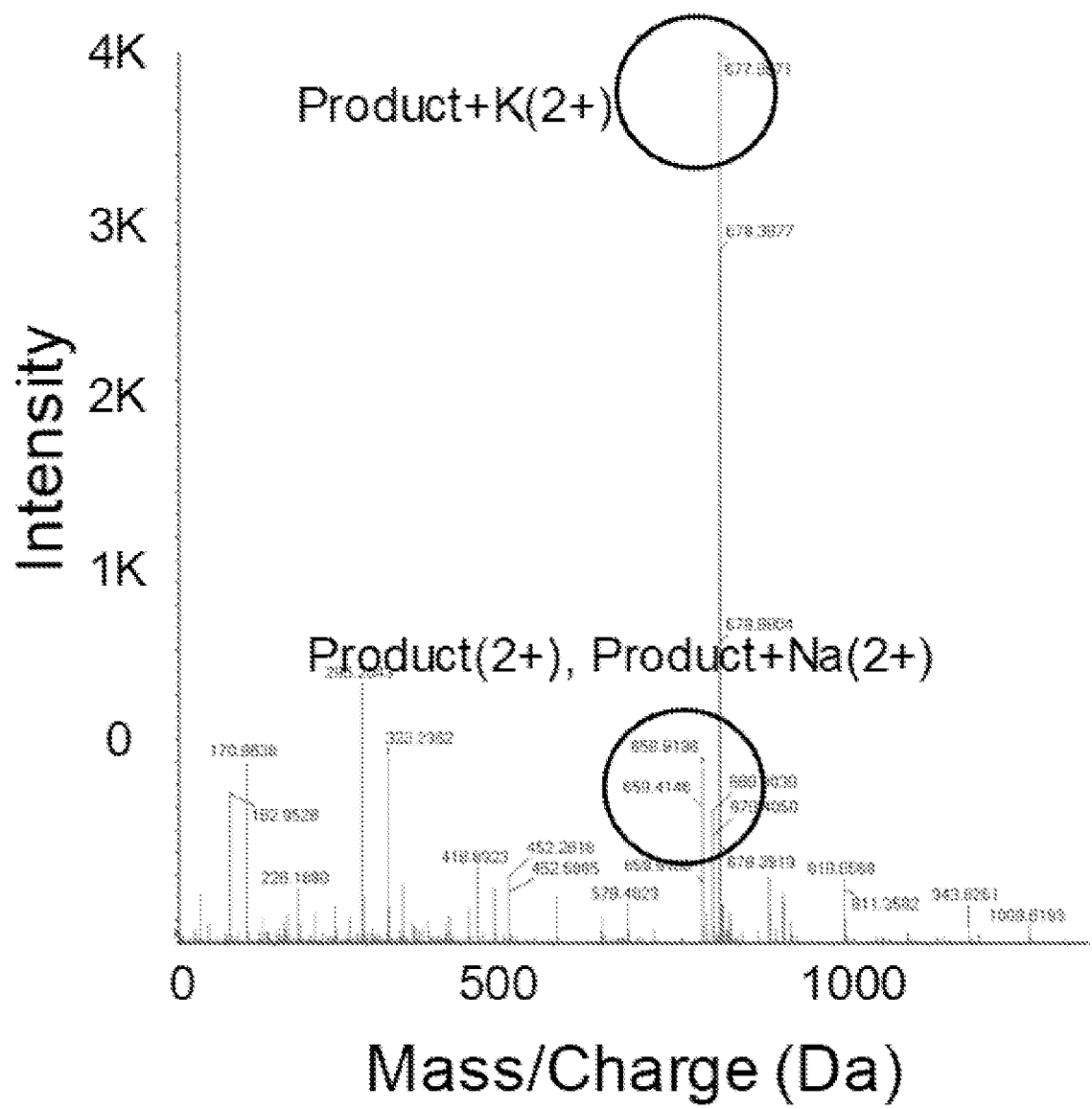
Figure 12C:
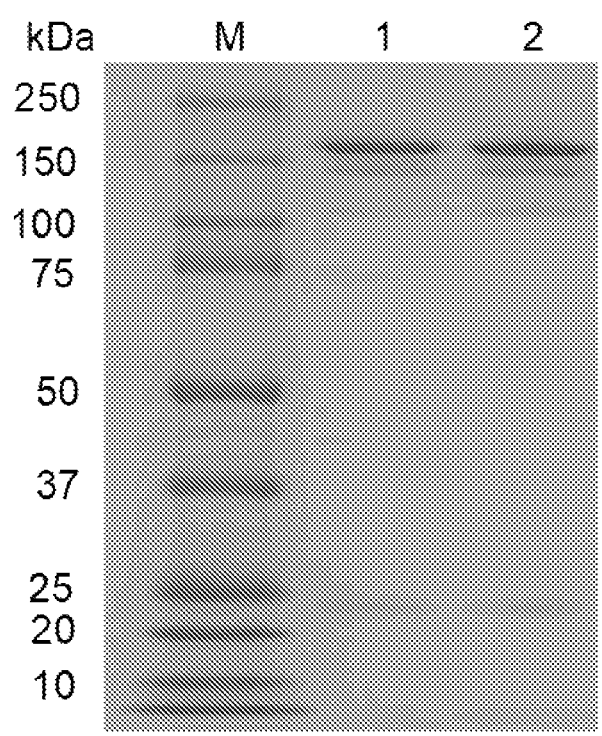

ADC construction and characterization. An established platform of a cysteine-based conjugation procedure (Ou J, et al. PLoS One. 2018 Oct 23 13(10):e0206246) was used to construct ADC. Herein, the rebridging peptide-based linker was synthesized to maintain high integrity of the mAb (FIG. 12A), conjugated with antimitotic monomethyl auristatin E (MMAE), and purified using Waters high-performance liquid chromatography (HPLC). The structure of linker was characterized using Agilent 6500 Q-TOF LC/MS (FIG. 12B), and the integrity of ADC structure was confirmed using SDS-PAGE (FIG. 12C). The average drug-antibody ratio (DAR) of the constructed ADC was approximately 4.0.

Figure 12D:
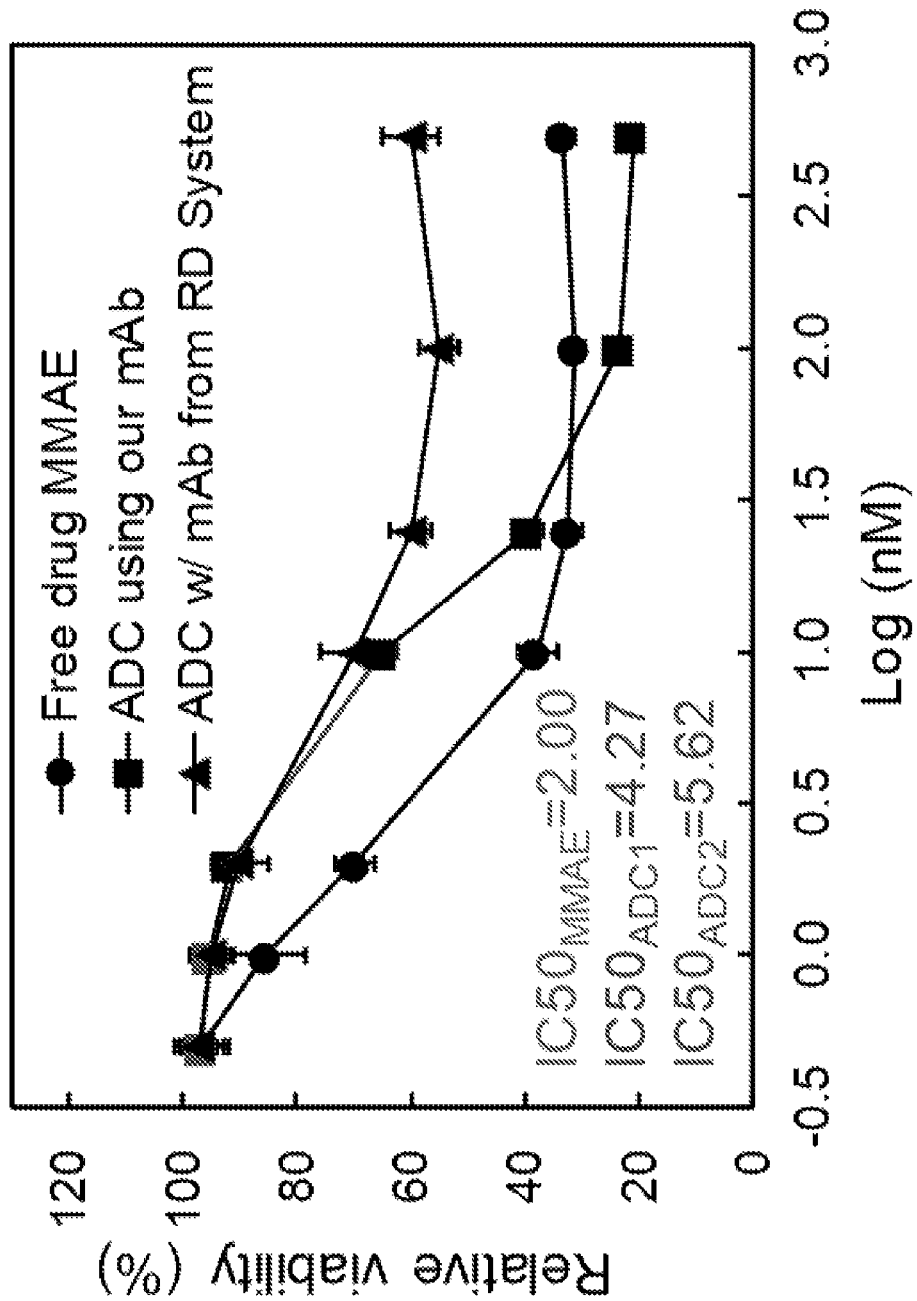

In vitro anti-cancer toxicity of anti-SSTR2 ADC showed a low $IC_{50}$. The in vitro anti-cancer toxicity of the anti-SSTR2 ADC in BON-1 cells was evaluated by comparing free drug (MMAE) and two different ADCs that included either the mAb developed in this study or the mAb from R&D Systems. MMAE was selected as the drug for the ADC due to the fact it is a potent cytotoxin that has already been clinically validated (Francisco J A, et al. Blood. 2003 102(4):1458-65; Yao H, et al. Int J Mol Sci. 2016 17(2)) as a microtubulin polymerization blocking agent (Cunningham D, et al. Prostate. 2016 76(15):1420-30; Li H, et al. Cancer Biol Ther. 2016 17(4):346-54). However, MMAE has never been tested in NETs. In this study, the $IC_{50}$ values of MMAE, ADC from the disclosed anti-SSTR2 mAb, and ADC from the commercial mAb were 2.00 nM, 4.27 nM, and 5.62 nM, respectively (FIG. 12D). It is clear that mAb-MMAE ADC has similar nanomolar cytotoxicity to NET cells as the highly potent free drug MMAE. With strong NET-targeting capability, the disclosed mAb-based ADC is expected to achieve better treatment efficacy in vivo than free drug.

Figure 12E:
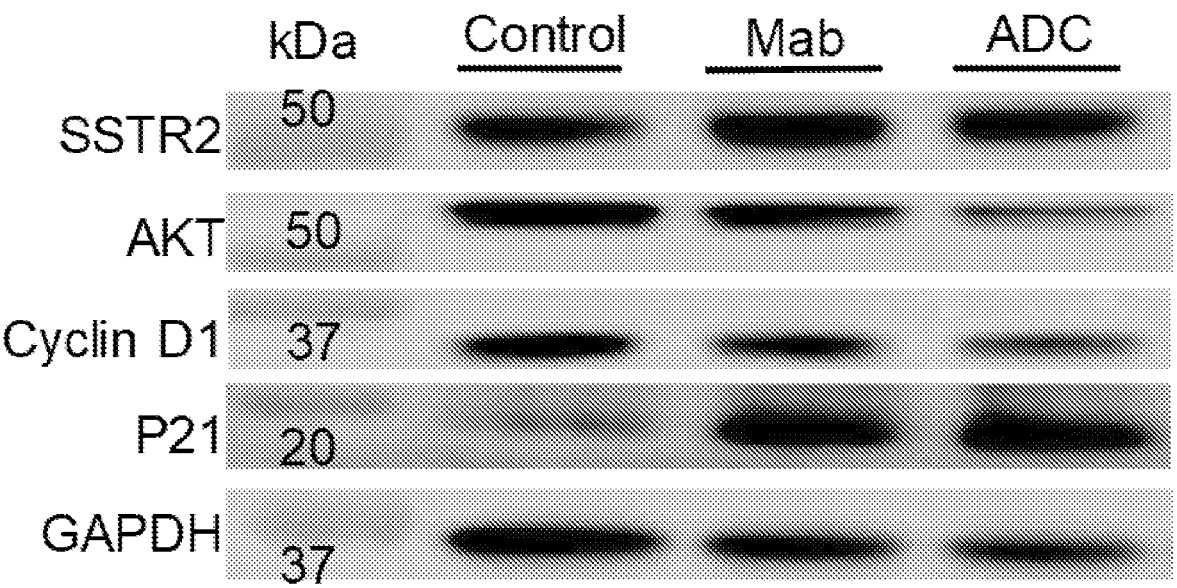
Figure 12F:
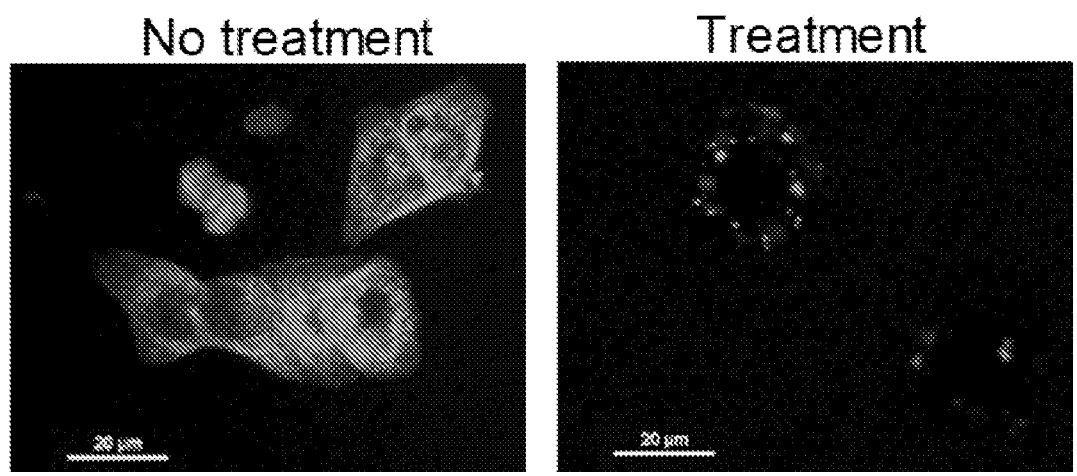

Anti-SSTR2 ADC has multiple potential anti-cancer mechanisms. To understand other potential anti-cancer mechanisms of the anti-SSTR2 ADC in addition to the cytotoxicity caused by the delivery of MMAE, several markers associated with cell proliferation signaling pathways were analyzed in BON-1 cells treated with the ADC for three days. Western blot showed that both anti-SSTR2 mAb alone and ADC can block cell proliferation signaling via the PI3K-AKT pathway, downregulate the oncogene Cyclin D1, and induce cell cycle arrest as seen by the detection of the marker p21 (FIG. 12E). These studies found that the ADC released MMAE inhibited NET cell proliferation by microtubule de-polymerization (FIG. 12F).

Figure 16:
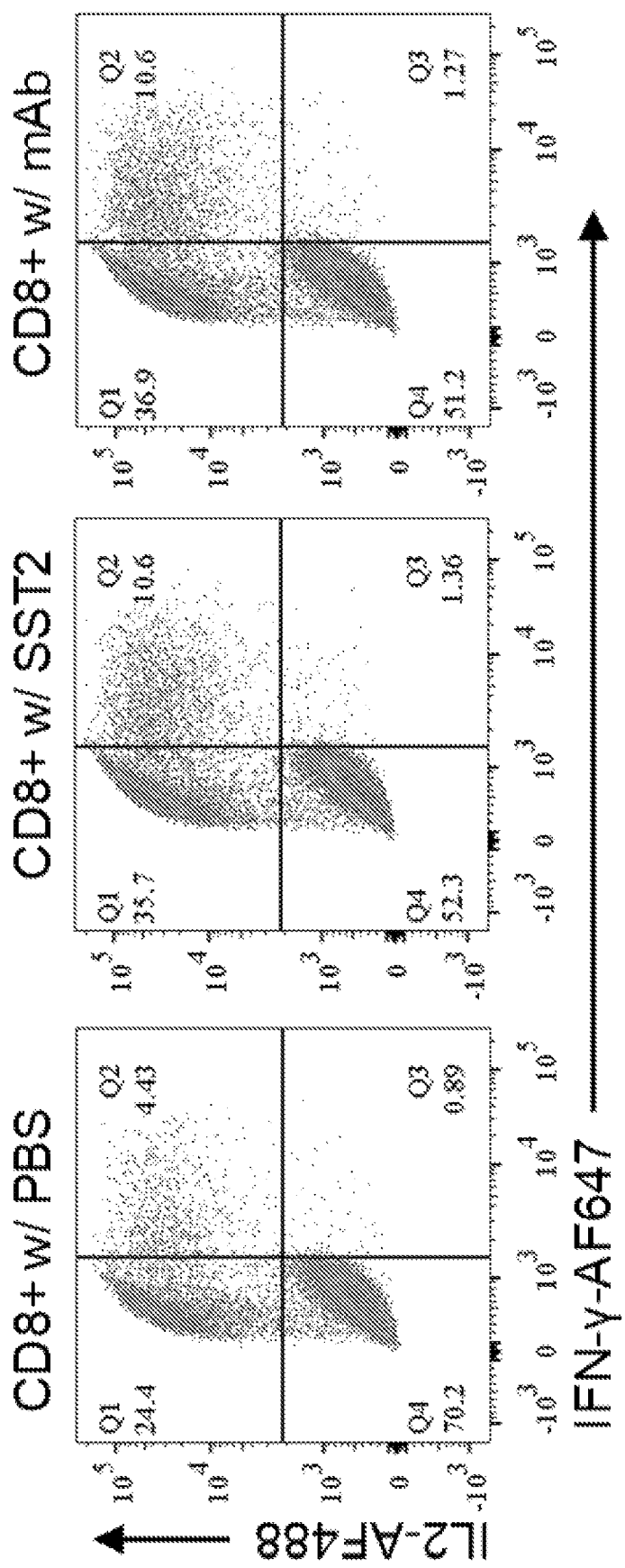
FIG. 16 shows flow cytometry analysis revealed that both IL2 and IFN-γ (cytokine) of human T cells were increased by our anti-SSTR2 mAb and SST analog (Octreotide).

Moreover, the possible effect of the disclosed anti-SSTR2 mAb on cytokine production in $CD8^+$ T cells was also tested. Post CD3/CD28 stimulation, human $CD8^+$ T cells were incubated with either 100 nM of SST analog (Octreotide) or 100 nM of the anti-SSTR2 mAb for 2 days. After incubation, flow cytometry was performed to analyze the expression of IL-2 and IFN-γ. As shown in FIG. 16, both the anti-SSTR2 mAb and Octreotide increased IL-2 expression by 1.6 folds and IFN-γ expression by 2.2 folds.

Figure 17:
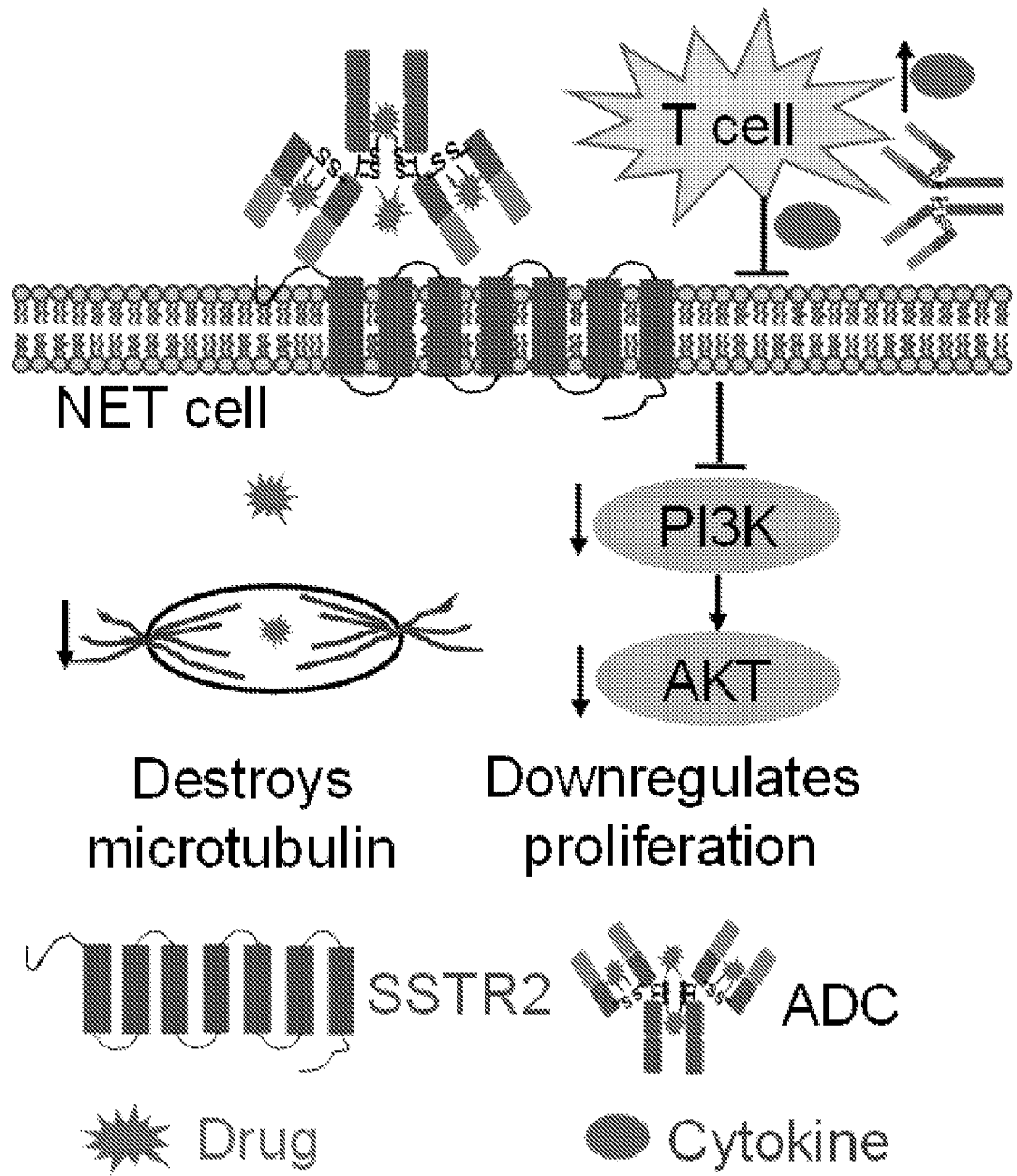
FIG. 17 shows hypothesized mechanism of anti-SSTR2 mAb-based ADC for NET treatment. (1) depolymerizing microtubulin by the mAb delivered drug; (2) downregulating proliferation signaling pathway through blocking SSTR2 by mAb; and (3) activating T cell's cytokine production.

In summary, several possible mechanisms of action for anti-SSTR2 ADC treatment of NETs are proposed (FIG. 17). The first mechanism is that the anti-SSTR2 mAb functions as a targeting delivery vehicle of drug to NET cells and the drug payload inhibits cancer cells proliferation via depolymerizing microtubulin. The second potential mechanism is that the PI3K-AKT proliferative signaling pathway is downregulated by the mAb binding and consequent blockage of SSTR2. The third potential mechanism is that the cytokine production of T cells is enhanced by the anti-SSTR2 mAb.

Figure 13A:
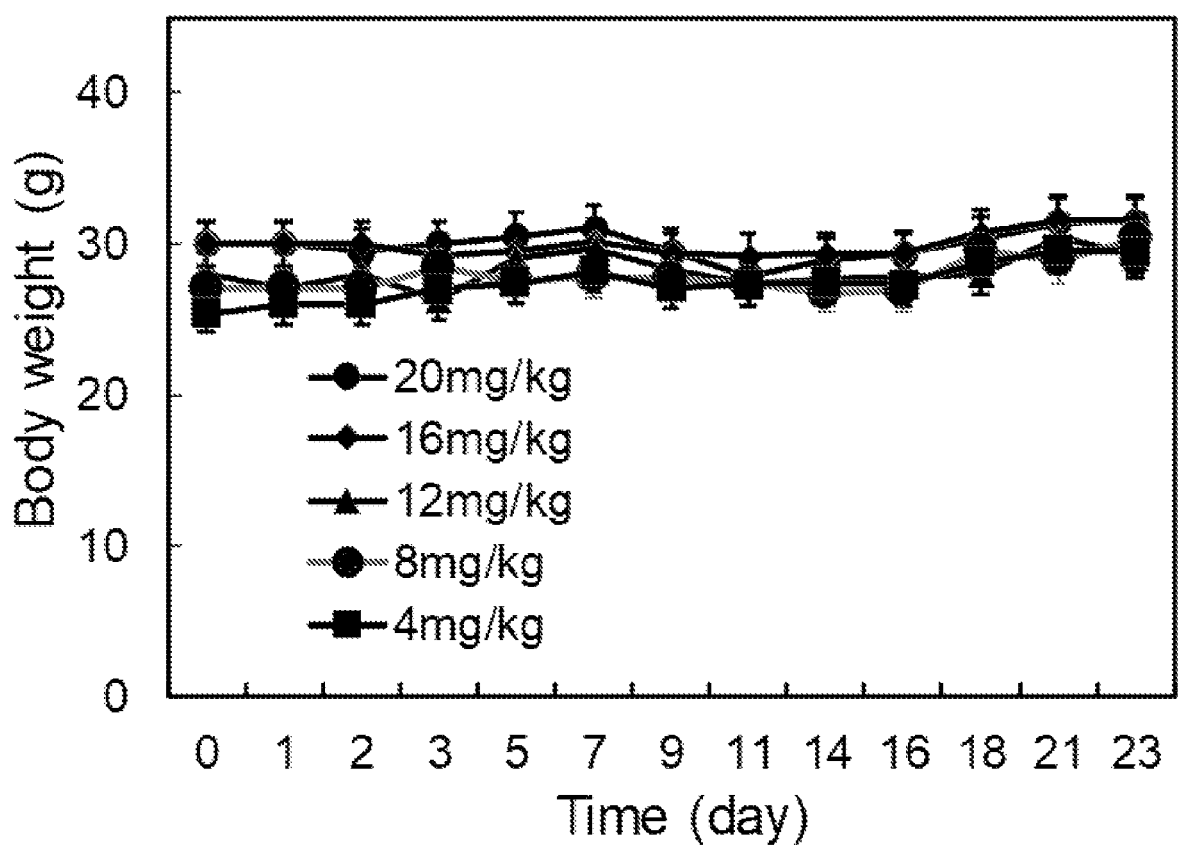
FIGS. 13A and 13B show MTD and PK study and effect on brain of ADC in s.c. PanNET xenografted mouse models.
Figure 13B:
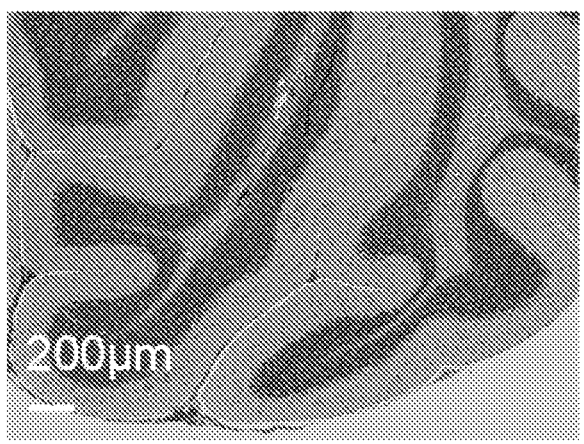
Figure 13B:
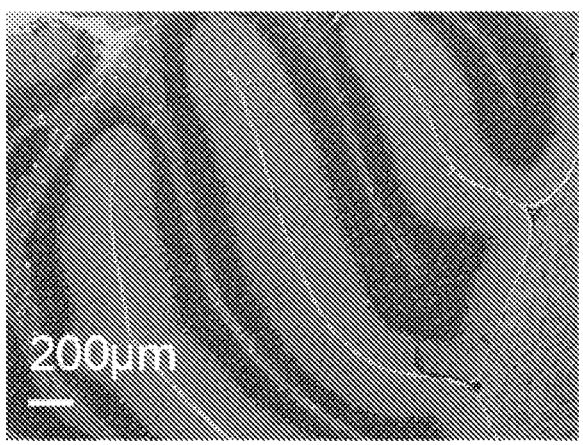
Figure 13B:
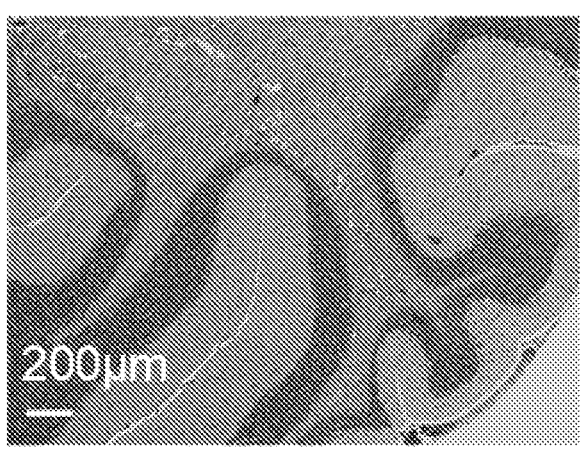
Figure 13B:
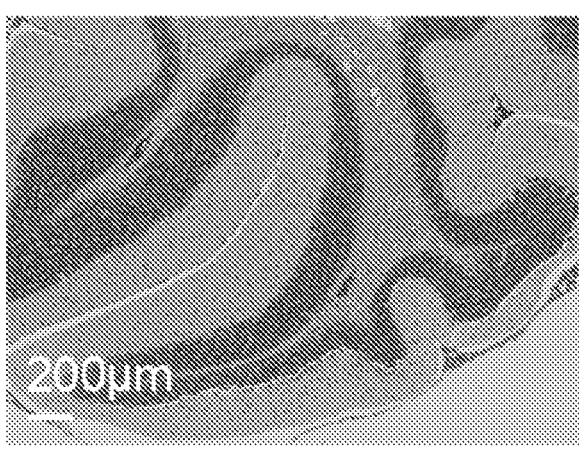

MTD of the anti-SSTR2 ADC showed no side effects. To investigate the maximum tolerated dose (MTD) of the anti-SSTR2 ADC, 5 different concentrations were injected into the tail vein of 5 wild-type (non-tumor bearing) mice: 4, 8, 12, 16, and 20 mg/kg of body weight (BW). Mice were monitored at six hours post-injection and twice daily for a total of 21 days and showed no signs of behavior changes such as water intake, labored breathing, rapid weight loss, impaired ambulation, and/or mentation. As shown in FIG. 13A, ADC at a concentration range of 4-20 mg/kg BW had no obvious side effects on mice body weight or overall survival. After monitoring for a total of three weeks, mice were sacrificed and brain tissue was collected for further studies. As shown in H&E staining (FIG. 13B), the brain tissue was not morphologically altered after the administration of the anti-SSTR2 ADC. There is no obvious drug delivery and no any signs of acute or chronic inflammation or any apoptotic or necrotic regions was observed. These results suggest that the anti-SSTR2 ADC treatment had no evident off-target effects and did not cause detectable damage to the brain in vivo.

Figure 13C:
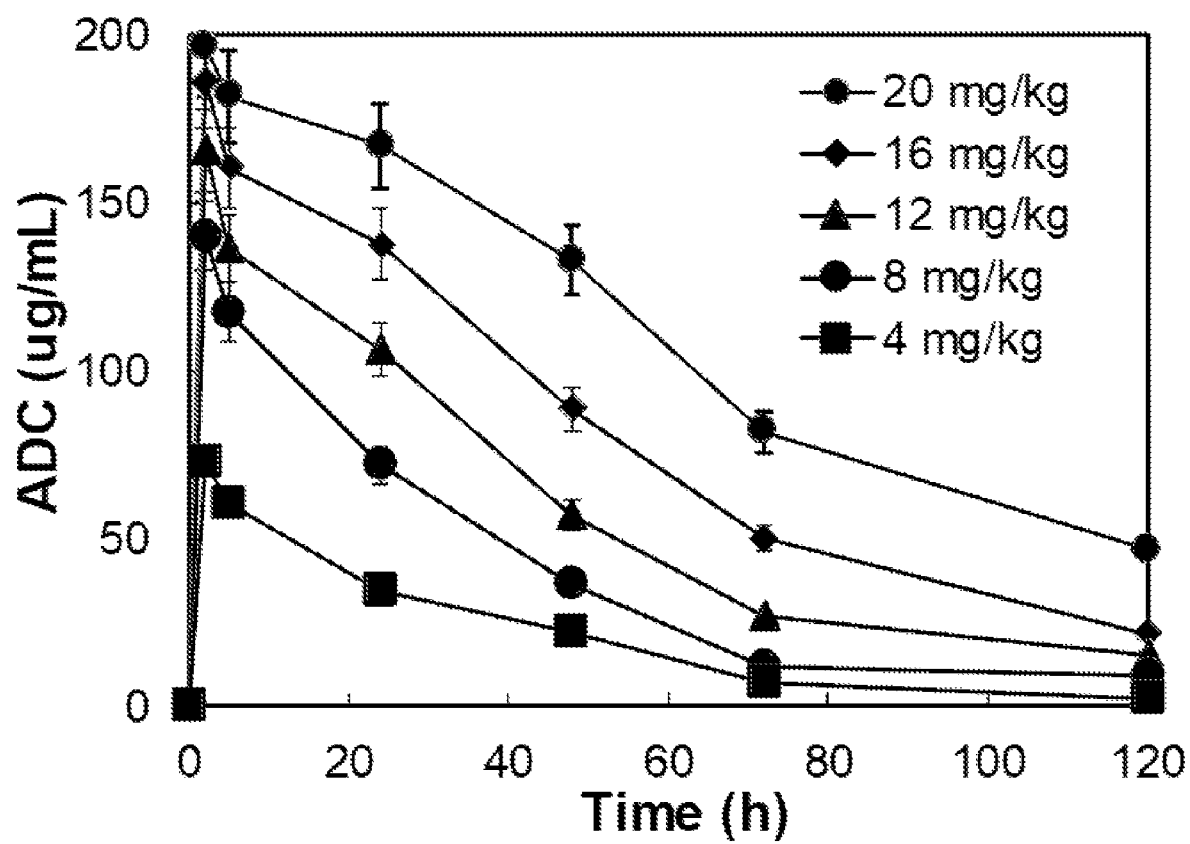
FIG. 13C shows PK studies show the stability and kinetics parameters of ADC (data represent mean±SEM, n=4).

PK indicated high stability of the anti-SSTR2 ADC. Preliminary pharmacokinetic (PK) studies were done by intravenously injecting the ADC into mice bearing subcutaneous NET xenograft at five different concentrations: 4, 8, 12, 16, and 20 mg/kg BW (n=4). Plasma samples were collected for PK analysis (10-50 μL each) from the tail vein at time points of: 0 hr, 2 hrs, 8 hrs, 16 hrs, 1 day, 2 days, 3 days, 5 days, and 7 days post-ADC injection and then titrated using an ELISA assay (FIG. 13C). As presented in Table 3 the PK modeling demonstrated the calculated half-life $(t_{1/2})$=1.38-2.33 days, volume of distribution $V_d$=63.05-94.42 mL/kg, the clearance rate $(C_L)$=28.01-37.45 mL/days/kg, bioavailability (F)=568.58-1293.26%, recommended dose (D)=3.78-14.30 mg/kg BW, and recommended dosing interval (τ)=4.40-9.10 days. Based on these results, a concentration of 8 mg/kg BW and a dosing interval of 4-5 days was selected for the remaining anti-cancer in vivo studies.

TABLE 3

PK modeling parameters.

| PK Parameters | Calculated Values |
| --- | --- |
| Half life $t_{1/2}$ (day) | 1.38-2.33 |
| Volume of distribution $V_d$ (mL/kg) | 63.05-94.42 |
| Clearance $C_L$ (mL/day/kg) | 28.01-37.45 |
| Bioavailability F (%) | 568.58-1293.26 |
| Calculated recommended dose D (mg/kg BW) | 3.78-14.30 |
| Calculated recommended dosing interval $_\tau$ (days) | 4.40-9.10 |

Figure 14A:
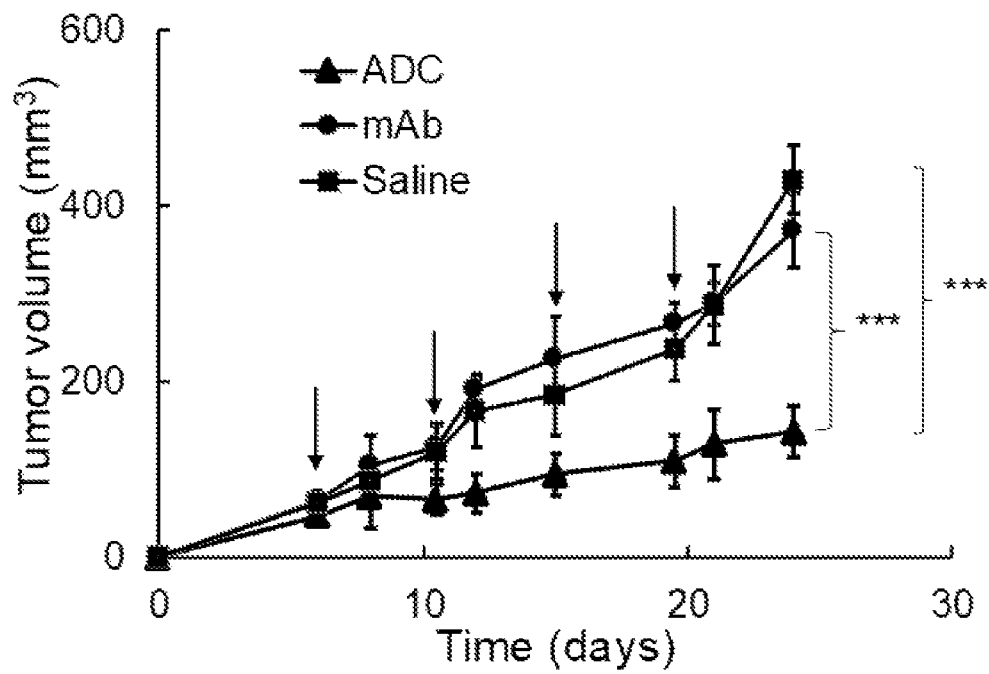
Figure 14B:
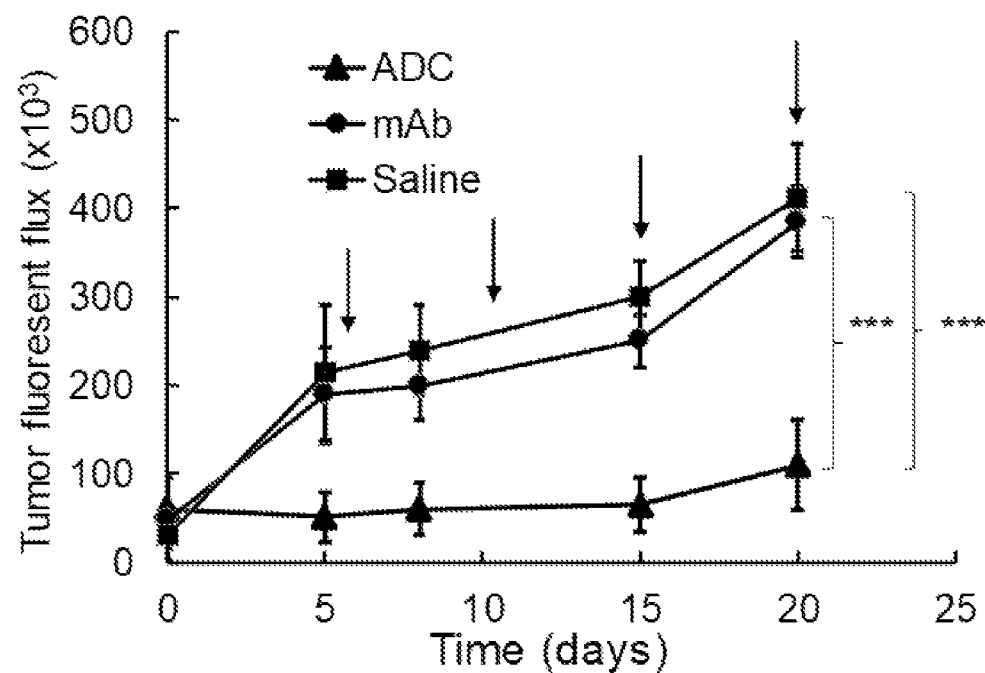
Figures 14C, 14D:
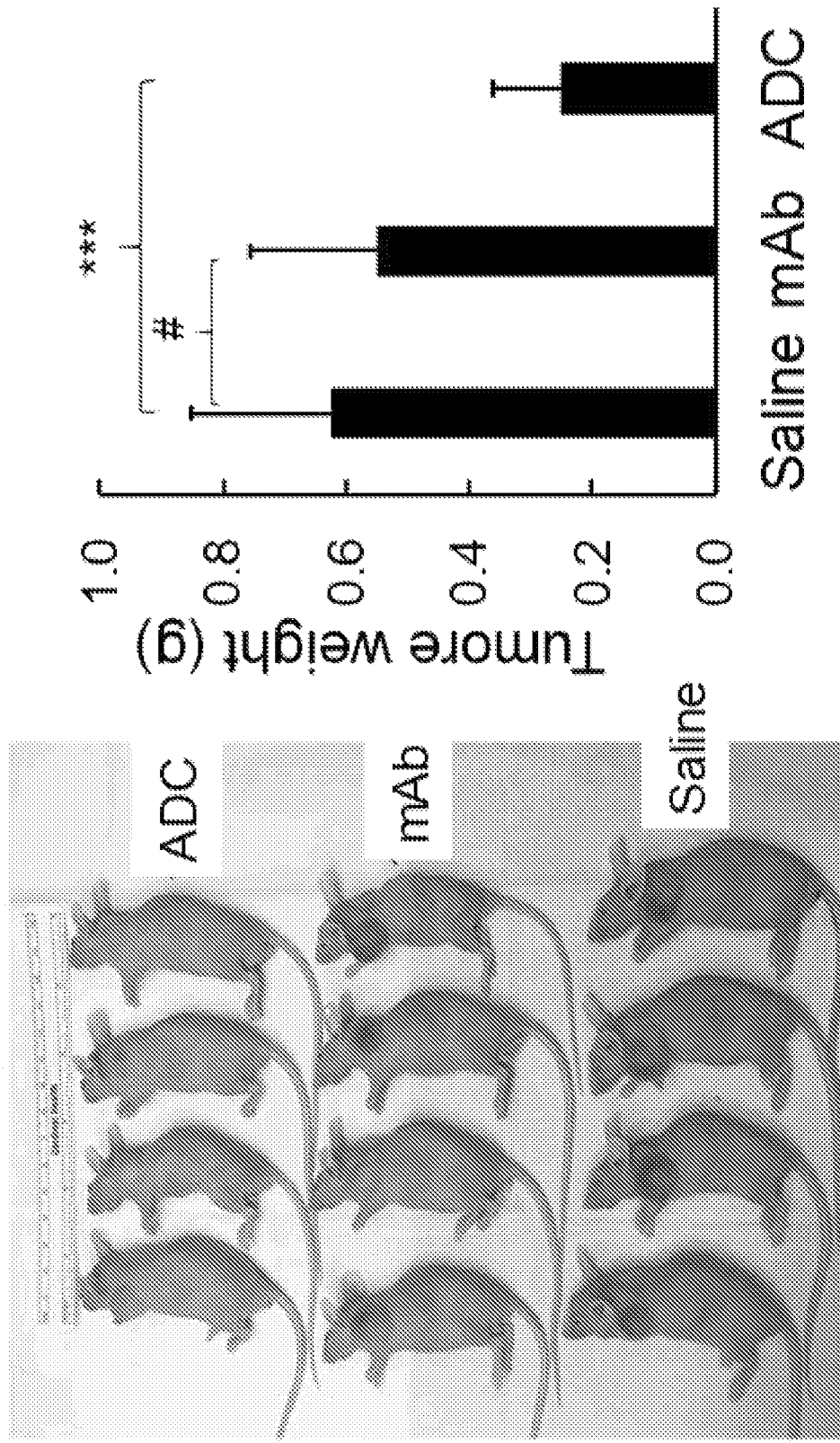
Figure 14E:
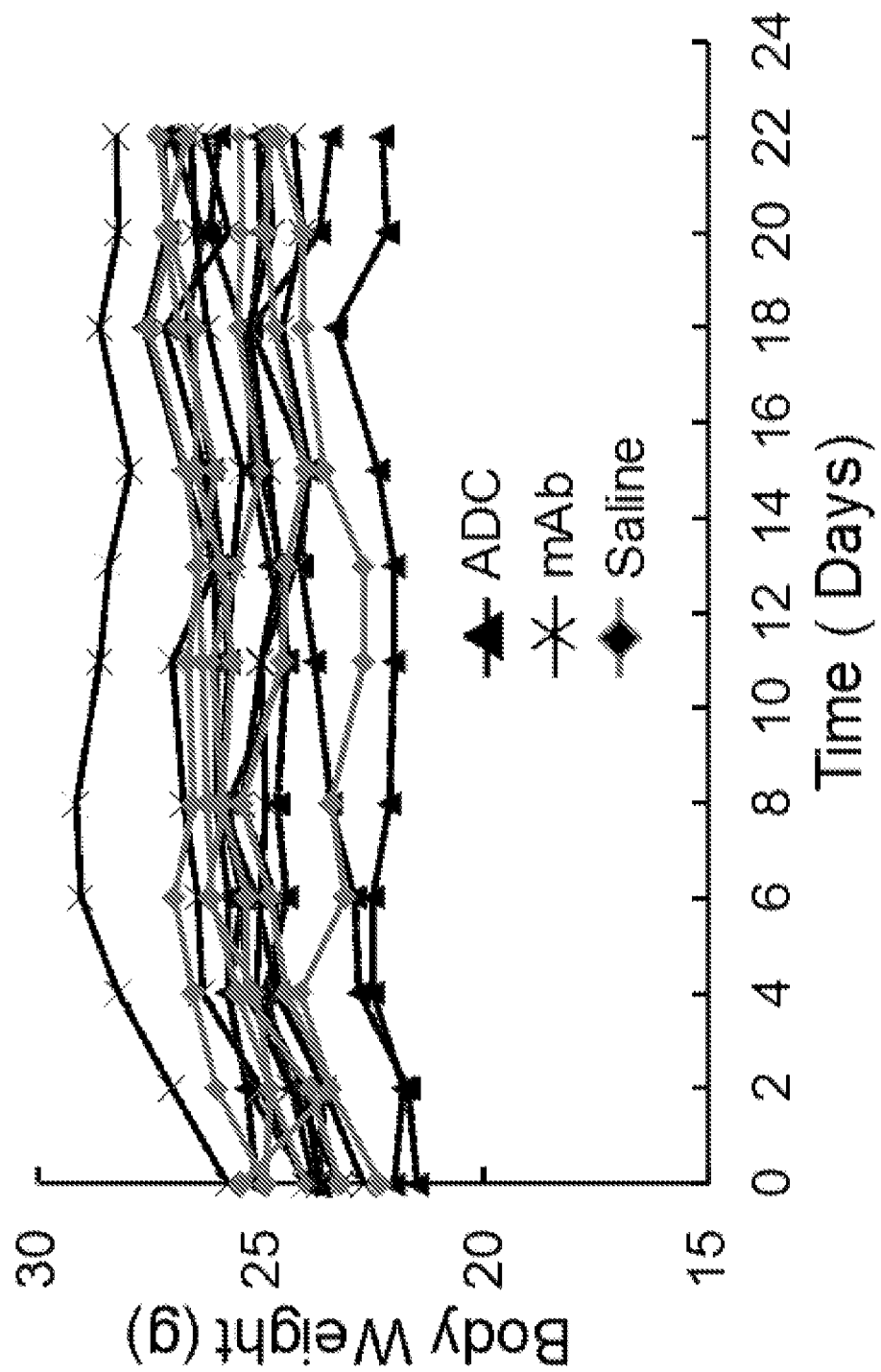

In vivo anti-cancer efficacy of anti-SSTR2 ADC. The mice bearing BON-Luc xenografts were treated in a dosing interval of 4.5 days with either: the anti-SSTR2 ADC at a concentration of 8 mg/kg, saline as a vehicle control, and anti-SSTR2 mAb (control, 8 mg/kg) in three groups (n=6). FIG. 14A shows that tumor growth was significantly inhibited with a tumor size reduction of 62-67% in the mice treated with the anti-SSTR2 ADC as compared with the controls. The tumor fluorescence flux was also measured with the IVIS imaging system and showed a reduction of 71-73% of tumor growth in the ADC treated group compared to control groups (FIG. 14B). The NET tumors were collected in the end of the study (FIG. 14C), and the wet weight also confirmed the significant inhibition of tumor growth (FIG. 14D). There was no obvious difference among the three groups in overall body weight (FIG. 14E). A Western blotting analysis showed that SSTR2 expression was present in NET tumors during treatment (FIG. 14F). The surface staining of SSTR2 in tumors from ADC treatment group appeared to be lower than the staining seen in the control group (FIG. 14G), likely due to the NET cell death caused by ADC which was confirmed through H&E staining (FIG. 14H). This in vivo anti-cancer efficacy study demonstrated that the anti-SSTR2 mAb is a good drug delivery vehicle and the antibody-drug conjugate can effectively inhibit NET growth.

DISCUSSION

SSTR2 receptor is an ideal NET target. To develop effective and safe targeted cancer therapies, a unique biomarker that specifically defines the cancer cells from the non-cancerous cells must be identified and thoroughly characterized. As reported in this study, SSTR2 is overexpressed in approximately 70% of 38 patients with NETs. Other studies also have reported that 70-100% of NETs abundantly express SSTR2 on the cell surface (Pinchot S N, et al. Oncologist. 2008 13(12):1255-69; Zatelli M C, et al. J Clin Endocrinol Metab. 2001 86(5):2161-9; Sun L C and Coy D H. Curr Drug Deliv. 2011 8(1):2-10). Although it has been reported that SSTR2 can be normally expressed in the central nervous system (CNS), gastrointestinal (GI) tract, and pancreas (Cakir M, et al. J Cell Mol Med. 2010 14(11):2570-84), the expression of SSTR2 in NET tissues was observed to be >20-fold higher than normal tissues in a tissue microarray using IHC analysis as described in this study and literature (Pinchot S N, et al. Oncologist. 2008 13(12):1255-69; Zatelli M C, et al. J Clin Endocrinol Metab. 2001 86(5):2161-9; Sun L C and Coy D H. Curr Drug Deliv. 2011 8(1):2-10). Considering that the mAb-based ADC is a dose-dependent targeted therapy, the drastic difference in SSTR2 expression between NETs and other tissues assures that it can be safe to exploit SSTR2.

However, not all patients with NETs overexpress SSTR2 (Righi L, et al. Ann Oncol. 2010 21(3):548-55; Sherman S K, et al. J Surg Res. 2014 190(2):587-93). It has been reported that 45-66% of patients with pulmonary NETs (Righi L, et al. Ann Oncol. 2010 21(3):548-55) and 80-95% patients with gastroenteropancreatic NETs express SSTR2. The tissue microarray analysis performed in this study showed that out of the 38 patient tissues stained, only about 71% showed detectable SSTR2 expression. In order to benefit the patients that lack a high expression of SSTR2, there are efforts to identify other potential surface markers in NETs, such as carcinoembryonic antigen-related cell adhesion molecule 1 (CEACAM1), using comparative membrane proteomics and Western blotting. We have found that CEACAM1 has high expression in two pancreatic NET cell lines (BON-1 and QGP-1) and no expression in neither pancreatic adenocarcinoma cell lines (PANC-1 and MiAPaCa-1) nor a fibroblast cell line (WI-38). Other studies also have reported CEACAM1 expression in various other cancers, including medullary thyroid cancer cell lines which represent a type of NET (Thies A, et al. J Clin Oncol. 2002 20(10):2530-6; Tilki D, et al. Oncogene. 2006 25(36):4965-74). This finding indicated that CEACAM1 could be used as an alternative of SSTR2 for the NET patients with minimal SSTR2 density.

The disclosed anti-SSTR2 mAb is an effective drug delivery vehicle. This study demonstrated that SSTR2 is an appropriate target for NET therapy. Differently from the commercial anti-SSTR2 mAb developed using the whole SSTR2 membrane protein as an immunogen, the new anti-SSTR2 mAb developed in this study was created using two extracellular domains of SSTR2 as immunogens. Therefore, it showed a binding capability to NET cells over 5 times greater than that of the commercially available anti-SSTR2 mAb.

The Human Atlas Project reported high mRNA level of SSTR2 in multiple normal human tissues, but the surface protein expression level of SSTR2 is the main consideration for targeted cancer therapy, rather than transcription level. This study analyzed multiple normal human organ tissue arrays (total of 33 organs), including most of the reported tissues with high mRNA, confirming the low or undetectable SSTR2 protein expression on the cell surface of these tissues. The live-animal IVIS imaging demonstrated that our anti-SSTR2 mAb exclusively accumulated in the NET xenograft. Since the disclosed mAb can target both human and mouse SSTR2, the in vivo specific targeting to NET in mouse models can indicate the specific targeting in patients. Additionally, the possible toxicity of anti-SSTR2 ADC on mice and specifically brain tissue was evaluated. The MTD data showed that a dose of up to 20 mg ADC/kg BW did not cause any body weight or behavior changes of the mice. Importantly, H&E staining on murine brain tissue did not show any evidence of damage or changes in cellular morphology. Therefore, the disclosed anti-SSTR2 mAb is a potentially safe drug delivery vehicle.

Innovative targeted therapy to effectively treat NETs. The mTOR inhibitor (Everolimus), multikinase inhibitor (Sunitinib), and SST analogs (e.g., Octreotide and Lanreotide) have been developed to treat NETs (Brown K T, et al. J Vasc Intery Radiol. 1999 10(4):397-403; Isozaki T, et al. Intern Med. 1999 38(1):17-21; Eriksson B, et al. Neuroendocrinology. 2008 87(1):8-19; Lal A and Chen H. Curr Opin Oncol. 2006 18(1):9-15; Lehnert T. Transplantation. 1998 66(10):1307-12; Zhang R, et al. Endocrinology. 1999 140 (5):2152-8; Boudreaux J P, et al. Ann Surg. 2005 241(6): 839-45; Nguyen C, et al. J Nucl Med. 2004 45(10):1660-8; Fiorentini G, et al. J Chemother. 2004 16(3):293-7; Zuetenhorst J M, et al. Endocr Relat Cancer. 2004 11(3):553-61; Oberg K, et al. Ann Oncol. 2004 15(6):966-73), but these drugs have limited therapeutic efficacy. In this study, for the first time, a SSTR2-targeted therapy in the form of a monoclonal antibody-drug conjugate was developed to target NETs. The ADC has advantages that include: enhanced cellular uptake via strong surface binding, high cytotoxicity of the small molecule payload that is delivered to cancer cells, and minimal side effects. This in vivo anti-cancer efficacy study demonstrated that tumor growth was significantly reduced upon treatment with the anti-SSTR2 ADC, which suggests that the disclosed mAb can effectively target NET cells and deliver the conjugated toxic drug. Moreover, the dislcosed anti-SSTR2 mAb can be used to tag the surface of liposomes and exosomes to facilitate the targeted delivery of other drugs. The single-chain variable fragment (scFv) can also be cloned to construct CAR-T cells for immunotherapy of NETs.

Synergistic therapy of anti-SSTR2 mAb and anti-SSTR2 ADC. Other studies have reported multiple direct and indirect mechanisms that could drive anti-tumor effects mediated by SSTR2. For example, the direct anti-proliferation mechanisms include apoptosis (uillermet J, et al. Proc Natl Acad Sci USA. 2003 100(1):155-60), regulation of cyclin-dependent kinase inhibitors, and the inhibition of proliferation signaling (Lahlou H, et al. Ann N Y Acad Sci. 2004 1014:121-31). The potential indirect anti-tumor effects include the inhibition of growth factor and hormone release, anti-angiogenic effects (Woltering E A. Cancer Biother Radiopharm. 2003 18(4):601-9), and immune response regulation (Elliott D E, et al. Eur J Immunol. 1999 29(8): 2454-63). The in vitro evaluation done in this study showed that the disclosed anti-SSTR2 mAb downregulates PI3K/AKT signaling which is associated with cell proliferation, downregulates the expression of the oncogene cyclin D1, upregulates p21 expression which is associated with cell cycle arrest, and activates $CD8^+$ T cells by increasing cytokine production. These findings indicate that this anti-SSTR2 mAb-based ADC could serve as a multi-purpose biologic with clinical potentials such as: directly causing cell death by releasing a cytotoxic payload into the cellular cytoplasm, inhibiting tumor cell growth cia the SSTR2-mediated modulation of signaling cascades, and re-activating T cell function by increasing cytokine production. Further investigation is necessary to better understand the possible synergy of anti-SSTR2 mAb and ADC for NET treatment in vivo using a sporadic MTC mouse model, humanized mouse model, and liver metastasis mouse model.

Impact of the disclosed targeted therapy. The disclosed anti-SSTR2 ADC has advantages over traditional chemotherapy, radiotherapy, and surgery to treat metastatic NE cancers. Compared to surgical procedures, anti-SSTR2 ADC can target and treat the metastatic nodules. Compared to chemotherapy, this therapy can reduce undesirable side effects and improve the anti-cancer therapeutic efficacy. Similar to other receptors that are FDA-approved for targeted therapies, SSTR2 is not an absolute NET-specific receptor, so it is imperative to further evaluate the potential side effects. The combination of the facts that SSTR2 expression in NETs is greater than normal tissues, SSTR2 has little or undetectable surface expression in most normal organs, and that the ADC is a dosage-dependent treatment strategy could minimize possible off-target side effects. Combined with other therapies, the targeted therapy developed in this study has great potential to improve the quality of life and survival rate of patients with NE cancers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody that selectively binds somatostatin receptor 2 (SSTR2) extracellular epitope on tumor cells, comprising a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence SEQ ID NO:1 or SEQ ID NO:26; the CDR2 sequence of the $V_H$ domain comprises the amino acid sequence SEQ ID NO:2 or SEQ ID NO:27; the CDR3 sequence of the $V_H$ domain comprises the amino acid sequence SEQ ID NO:3; the CDR1 sequence of the $V_L$ comprises the amino acid sequence SEQ ID NO:4; the CDR2 sequence of the $V_L$ domain comprises the amino acid sequence SEQ ID NO:5; and the CDR3 sequence of the $V_L$ domain comprises the amino acid sequence SEQ ID NO:6 or SEQ ID NO:28.

2. The antibody of claim 1, wherein the anti-SSTR2 $V_H$ domain comprises the amino acid sequence SEQ ID NO:7 or SEQ ID NO:18.

3. The antibody of claim 1, wherein the anti-SSTR2 $V_L$ domain comprises the amino acid sequence SEQ ID NO:8 or SEQ ID NO:19.

4. The antibody of claim 1, comprising the amino acid sequence SEQ ID NO:12, SEQ ID NO: 13, SEQ ID NO:20, SEQ ID NO:21, SEQ ID NO:22, SEQ ID NO:23, SEQ ID NO:24, or SEQ ID NO:25.

5. The antibody of claim 1, wherein the antibody is a recombinant antibody.

6. The antibody of claim 5, wherein the antibody is a single chain (scFv) antibody.

7. An isolated nucleic acid sequence encoding the recombinant antibody of claim 1.

8. A vector comprising the isolated nucleic acid sequence of claim 7.

9. A cell comprising the vector of claim 8.

10. A composition, comprising the antibody of claim 1 conjugated to an anti-cancer agent.

11. The composition of claim 10, wherein the anti-cancer agent is monomethyl auristatin E, gemcitabine, or resveratrol.

12. A method of treating an SSTR2 expressing neuroendocrine (NE) cancer in a subject, the method comprising administering to the subject an effective amount of the composition of claim 10.

* * * * *

SEQUENCE LISTING

```
<160> NUMBER OF SEQ ID NOS: 30

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp Tyr His Leu Asn
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

Ile Arg Asn Lys Arg Tyr Gly Tyr Arg Thr Glu Tyr Ser Ala Ser Val
1               5                   10                  15

Lys Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Asp Phe Tyr Asp Pro Phe Ala Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Arg Ser Ser Gln Ser Leu Val His Ser Asn Gly Asn Thr Tyr Leu His
1               5                   10                  15

<210> SEQ ID NO 5
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ser Gln Ser Thr His Val Pro Phe Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

His Leu Asn Trp Val Arg Gln Pro Pro Gly Lys Ala Leu Glu Trp Leu
        35                  40                  45

Ala Leu Ile Arg Asn Lys Arg Tyr Gly Tyr Arg Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Phe Tyr Asp Pro Phe Ala Tyr Trp Gly Gln Gly
            100                 105                 110

Thr Leu Val Thr Val Ser Ala
        115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Ser Ser Gly Gly Gly Gly Ser Gly Gly Gly Ser Gly Gly Gly Ser
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: Synthetic Construct

<400> SEQUENCE: 11

Gly Ser Thr Ser Gly Ser Gly Lys Pro Gly Ser Gly Glu Gly Ser Thr
1               5                   10                  15

Lys Gly

<210> SEQ ID NO 12
<211> LENGTH: 284
<212> TYPE: PRT
<213> ORGANISM: Artificial Sequence
<220> FEATURE:
<223> OTHER INFORMATION: Synthetic Construct

<400> SEQUENCE: 12

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr His Leu Asn Trp Val Arg Gln Pro Pro Gly Lys Ala Leu
    50                  55                  60

Glu Trp Leu Ala Leu Ile Arg Asn Lys Arg Tyr Gly Tyr Arg Thr Glu
65                  70                  75                  80

Tyr Ser Ala Ser Val Lys Gly Arg Phe Thr Ile Ser Arg Asp Asn Ser
                85                  90                  95

```
Gln Ser Ile Leu Tyr Leu Gln Met Asn Thr Leu Arg Ala Glu Asp Ser
                100                 105                 110

Ala Thr Tyr Tyr Cys Ala Arg Asp Phe Tyr Pro Phe Ala Tyr Trp
        115                 120                 125

Gly Gln Gly Thr Leu Val Thr Val Ser Ala Gly Gly Gly Ser Gly
    130                 135                 140

Gly Gly Gly Ser Gly Gly Gly Ser Met Lys Leu Pro Val Arg Leu
145                 150                 155                 160

Leu Val Leu Met Phe Trp Ile Pro Ala Ser Ser Asp Val Val Met
                165                 170                 175

Thr Gln Thr Pro Leu Ser Leu Pro Val Ser Leu Gly Asp Gln Ala Ser
                180                 185                 190

Ile Ser Cys Arg Ser Ser Gln Ser Leu Val His Ser Asn Gly Asn Thr
        195                 200                 205

Tyr Leu His Trp Tyr Leu Gln Arg Pro Gly Gln Ser Pro Lys Leu Leu
    210                 215                 220

Ile Tyr Lys Val Ser Asn Arg Phe Ser Gly Val Pro Asp Arg Phe Ser
225                 230                 235                 240

Gly Ser Gly Ser Gly Thr Asp Phe Thr Leu Lys Ile Ser Arg Val Glu
                245                 250                 255

Ala Glu Asp Leu Gly Val Tyr Phe Cys Ser Gln Ser Thr His Val Pro
                260                 265                 270

Phe Thr Phe Gly Ser Gly Thr Lys Leu Glu Ile Lys
                275                 280

<210> SEQ ID NO 13
<211> LENGTH: 284
<212> TYPE: PRT
<213> ORGANISM: Artificial Sequence
<220> FEATURE:
<223> OTHER INFORMATION: Synthetic Construct

<400> SEQUENCE: 13

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Arg Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
                100                 105                 110

Ser Gln Ser Thr His Val Pro Phe Thr Phe Gly Ser Gly Thr Lys Leu
        115                 120                 125

Glu Ile Lys Gly Gly Gly Gly Ser Gly Gly Gly Gly Ser Gly Gly Gly
    130                 135                 140

Gly Ser Met Lys Leu Trp Leu Asn Trp Ile Phe Leu Val Thr Leu Leu
145                 150                 155                 160

Asn Gly Ile Gln Cys Glu Val Lys Leu Val Glu Ser Gly Gly Gly Leu
                165                 170                 175
```

```
Val Gln Pro Gly Gly Ser Leu Arg Leu Ser Cys Ala Thr Ser Gly Phe
            180                 185                 190

Thr Phe Thr Asp Tyr His Leu Asn Trp Val Arg Gln Pro Pro Gly Lys
        195                 200                 205

Ala Leu Glu Trp Leu Ala Leu Ile Arg Asn Lys Arg Tyr Gly Tyr Arg
    210                 215                 220

Thr Glu Tyr Ser Ala Ser Val Lys Gly Arg Phe Thr Ile Ser Arg Asp
225                 230                 235                 240

Asn Ser Gln Ser Ile Leu Tyr Leu Gln Met Asn Thr Leu Arg Ala Glu
                245                 250                 255

Asp Ser Ala Thr Tyr Tyr Cys Ala Arg Asp Phe Tyr Asp Pro Phe Ala
            260                 265                 270

Tyr Trp Gly Gln Gly Thr Leu Val Thr Val Ser Ala
        275                 280
```

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

```
Cys Gln Thr Glu Pro Tyr Tyr Asp Leu Thr Ser Asn Ala
1               5                   10
```

<210> SEQ ID NO 15
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

```
Cys Ala Leu Val His Trp Pro Phe Gly Lys Ala Ile Cys Arg Val Val
1               5                   10                  15
```

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

```
Gln Thr Glu Pro Tyr Tyr Asp Leu Thr Ser Asn Ala
1               5                   10
```

<210> SEQ ID NO 17
<211> LENGTH: 15
<212> TYPE: PRT
<213> ORGANISM: Artificial Sequence
<220> FEATURE:
<223> OTHER INFORMATION: Synthetic Construct

<400> SEQUENCE: 17

```
Ala Leu Val His Trp Pro Phe Gly Lys Ala Ile Cys Arg Val Val
1               5                   10                  15
```

<210> SEQ ID NO 18
<211> LENGTH: 119
<212> TYPE: PRT
<213> ORGANISM: Artificial Sequence
<220> FEATURE:

<223> OTHER INFORMATION: Synthetic Construct

<400> SEQUENCE: 18

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

His Met Asn Trp Val Arg Gln Pro Pro Gly Lys Ala Leu Glu Trp Leu
        35                  40                  45

Ala Leu Ile Arg Asn Lys Ala Asn Gly Tyr Arg Thr Glu Tyr Ser Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Phe Tyr Asp Pro Phe Ala Tyr Trp Gly Gln Gly
            100                 105                 110

Thr Leu Val Thr Val Ser Ala
        115

<210> SEQ ID NO 19
<211> LENGTH: 112
<212> TYPE: PRT
<213> ORGANISM: Artificial Sequence
<220> FEATURE:
<223> OTHER INFORMATION: Synthetic Construct

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr Arg Val Pro Phe Thr Phe Gly Ser Gly Thr Lys Leu Glu Ile Lys
            100                 105                 110

<210> SEQ ID NO 20
<211> LENGTH: 284
<212> TYPE: PRT
<213> ORGANISM: Artificial Sequence
<220> FEATURE:
<223> OTHER INFORMATION: Synthetic Construct

<400> SEQUENCE: 20

Met Lys Leu Trp Leu Asn Trp Ile Phe Pro Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr His Met Asn Trp Val Arg Gln Pro Pro Gly Lys Ala Leu

```
            50                  55                  60
Glu Trp Leu Ala Leu Ile Arg Asn Lys Ala Asn Gly Tyr Arg Thr Glu
65                  70                  75                  80

Tyr Ser Ala Ser Val Lys Gly Arg Phe Thr Ile Ser Arg Asp Asn Ser
                85                  90                  95

Gln Asn Ile Leu Tyr Leu Gln Met Asn Thr Leu Arg Ala Glu Asp Ser
            100                 105                 110

Ala Thr Tyr Tyr Cys Ala Arg Asp Phe Tyr Asp Pro Phe Ala Tyr Trp
            115                 120                 125

Gly Gln Gly Thr Leu Val Thr Val Ser Ala Gly Gly Gly Ser Gly
        130                 135                 140

Gly Gly Gly Ser Gly Gly Gly Ser Met Lys Leu Pro Val Gly Leu
145                 150                 155                 160

Leu Val Leu Met Phe Trp Ile Pro Ala Ser Ser Asp Val Val Met
                165                 170                 175

Thr Gln Thr Pro Leu Ser Leu Pro Val Ser Leu Gly Asp Gln Ala Ser
            180                 185                 190

Ile Ser Cys Arg Ser Ser Gln Ser Leu Val His Ser Asn Gly Asn Thr
            195                 200                 205

Tyr Leu His Trp Tyr Leu Gln Arg Pro Gly Gln Ser Pro Asn Leu Leu
        210                 215                 220

Ile Tyr Lys Val Ser Asn Arg Phe Ser Gly Val Pro Asp Arg Phe Ser
225                 230                 235                 240

Gly Ser Gly Ser Gly Thr Asp Phe Thr Leu Lys Ile Ser Arg Val Glu
                245                 250                 255

Ala Glu Asp Leu Gly Leu Tyr Phe Cys Ser Gln Ser Thr Arg Val Pro
            260                 265                 270

Phe Thr Phe Gly Ser Gly Thr Lys Leu Glu Ile Lys
            275                 280

<210> SEQ ID NO 21
<211> LENGTH: 284
<212> TYPE: PRT
<213> ORGANISM: Artificial Sequence
<220> FEATURE:
<223> OTHER INFORMATION: Synthetic Construct

<400> SEQUENCE: 21

Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Arg Pro
        50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Ser Gln Ser Thr Arg Val Pro Phe Thr Phe Gly Ser Gly Thr Lys Leu
            115                 120                 125

Glu Ile Lys Gly Gly Gly Gly Ser Gly Gly Gly Gly Ser Gly Gly Gly
```

```
            130                 135                 140
Gly Ser Met Lys Leu Trp Leu Asn Trp Ile Phe Pro Val Thr Leu Leu
145                 150                 155                 160

Asn Gly Ile Gln Cys Glu Val Lys Leu Val Glu Ser Gly Gly Gly Leu
                165                 170                 175

Val Gln Pro Gly Gly Ser Leu Arg Leu Ser Cys Ala Thr Ser Gly Phe
            180                 185                 190

Thr Phe Thr Asp Tyr His Met Asn Trp Val Arg Gln Pro Pro Gly Lys
        195                 200                 205

Ala Leu Glu Trp Leu Ala Leu Ile Arg Asn Lys Ala Asn Gly Tyr Arg
    210                 215                 220

Thr Glu Tyr Ser Ala Ser Val Lys Gly Arg Phe Thr Ile Ser Arg Asp
225                 230                 235                 240

Asn Ser Gln Asn Ile Leu Tyr Leu Gln Met Asn Thr Leu Arg Ala Glu
                245                 250                 255

Asp Ser Ala Thr Tyr Tyr Cys Ala Arg Asp Phe Tyr Asp Pro Phe Ala
            260                 265                 270

Tyr Trp Gly Gln Gly Thr Leu Val Thr Val Ser Ala
        275                 280

<210> SEQ ID NO 22
<211> LENGTH: 284
<212> TYPE: PRT
<213> ORGANISM: Artificial Sequence
<220> FEATURE:
<223> OTHER INFORMATION: Synthetic Construct

<400> SEQUENCE: 22

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
                20                  25                  30

Pro Gly Gly Ser Leu Arg Leu Ser Cys Ala Thr Ser Gly Phe Thr Phe
            35                  40                  45

Thr Asp Tyr His Leu Asn Trp Val Arg Gln Pro Pro Gly Lys Ala Leu
        50                  55                  60

Glu Trp Leu Ala Leu Ile Arg Asn Lys Arg Tyr Gly Tyr Arg Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Phe Tyr Asp Pro Phe Ala Tyr Trp
        115                 120                 125

Gly Gln Gly Thr Leu Val Thr Val Ser Ala Gly Gly Gly Ser Gly
    130                 135                 140

Gly Gly Gly Ser Gly Gly Gly Ser Met Lys Leu Pro Val Gly Leu
145                 150                 155                 160

Leu Val Leu Met Phe Trp Ile Pro Ala Ser Ser Asp Val Val Met
                165                 170                 175

Thr Gln Thr Pro Leu Ser Leu Pro Val Ser Leu Gly Asp Gln Ala Ser
            180                 185                 190

Ile Ser Cys Arg Ser Ser Gln Ser Leu Val His Ser Asn Gly Asn Thr
        195                 200                 205

Tyr Leu His Trp Tyr Leu Gln Arg Pro Gly Gln Ser Pro Asn Leu Leu
```

```
            210                 215                 220
Ile Tyr Lys Val Ser Asn Arg Phe Ser Gly Val Pro Asp Arg Phe Ser
225                 230                 235                 240

Gly Ser Gly Ser Gly Thr Asp Phe Thr Leu Lys Ile Ser Arg Val Glu
                245                 250                 255

Ala Glu Asp Leu Gly Leu Tyr Phe Cys Ser Gln Ser Thr Arg Val Pro
                260                 265                 270

Phe Thr Phe Gly Ser Gly Thr Lys Leu Glu Ile Lys
                275                 280
```

<210> SEQ ID NO 23
<211> LENGTH: 284
<212> TYPE: PRT
<213> ORGANISM: Artificial Sequence
<220> FEATURE:
<223> OTHER INFORMATION: Synthetic Construct

<400> SEQUENCE: 23

```
Met Lys Leu Pro Val Gly Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Arg Pro
        50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
                100                 105                 110

Ser Gln Ser Thr Arg Val Pro Phe Thr Phe Gly Ser Gly Thr Lys Leu
                115                 120                 125

Glu Ile Lys Gly Gly Gly Gly Ser Gly Gly Gly Gly Ser Gly Gly Gly
130                 135                 140

Gly Ser Met Lys Leu Trp Leu Asn Trp Ile Phe Leu Val Thr Leu Leu
145                 150                 155                 160

Asn Gly Ile Gln Cys Glu Val Lys Leu Val Glu Ser Gly Gly Gly Leu
                165                 170                 175

Val Gln Pro Gly Gly Ser Leu Arg Leu Ser Cys Ala Thr Ser Gly Phe
                180                 185                 190

Thr Phe Thr Asp Tyr His Leu Asn Trp Val Arg Gln Pro Pro Gly Lys
                195                 200                 205

Ala Leu Glu Trp Leu Ala Leu Ile Arg Asn Lys Arg Tyr Gly Tyr Arg
                210                 215                 220

Thr Glu Tyr Ser Ala Ser Val Lys Gly Arg Phe Thr Ile Ser Arg Asp
225                 230                 235                 240

Asn Ser Gln Ser Ile Leu Tyr Leu Gln Met Asn Thr Leu Arg Ala Glu
                245                 250                 255

Asp Ser Ala Thr Tyr Tyr Cys Ala Arg Asp Phe Tyr Asp Pro Phe Ala
                260                 265                 270

Tyr Trp Gly Gln Gly Thr Leu Val Thr Val Ser Ala
                275                 280
```

-continued

```
<210> SEQ ID NO 24
<211> LENGTH: 284
<212> TYPE: PRT
<213> ORGANISM: Artificial Sequence
<220> FEATURE:
<223> OTHER INFORMATION: Synthetic Construct

<400> SEQUENCE: 24

Met Lys Leu Trp Leu Asn Trp Ile Phe Pro Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr His Met Asn Trp Val Arg Gln Pro Pro Gly Lys Ala Leu
    50                  55                  60

Glu Trp Leu Ala Leu Ile Arg Asn Lys Ala Asn Gly Tyr Arg Thr Glu
65                  70                  75                  80

Tyr Ser Ala Ser Val Lys Gly Arg Phe Thr Ile Ser Arg Asp Asn Ser
                85                  90                  95

Gln Asn Ile Leu Tyr Leu Gln Met Asn Thr Leu Arg Ala Glu Asp Ser
            100                 105                 110

Ala Thr Tyr Tyr Cys Ala Arg Asp Phe Tyr Asp Pro Phe Ala Tyr Trp
        115                 120                 125

Gly Gln Gly Thr Leu Val Thr Val Ser Ala Gly Gly Gly Gly Ser Gly
    130                 135                 140

Gly Gly Gly Ser Gly Gly Gly Gly Ser Met Lys Leu Pro Val Arg Leu
145                 150                 155                 160

Leu Val Leu Met Phe Trp Ile Pro Ala Ser Ser Ser Asp Val Val Met
                165                 170                 175

Thr Gln Thr Pro Leu Ser Leu Pro Val Ser Leu Gly Asp Gln Ala Ser
            180                 185                 190

Ile Ser Cys Arg Ser Ser Gln Ser Leu Val His Ser Asn Gly Asn Thr
        195                 200                 205

Tyr Leu His Trp Tyr Leu Gln Arg Pro Gly Gln Ser Pro Lys Leu Leu
    210                 215                 220

Ile Tyr Lys Val Ser Asn Arg Phe Ser Gly Val Pro Asp Arg Phe Ser
225                 230                 235                 240

Gly Ser Gly Ser Gly Thr Asp Phe Thr Leu Lys Ile Ser Arg Val Glu
                245                 250                 255

Ala Glu Asp Leu Gly Val Tyr Phe Cys Ser Gln Ser Thr His Val Pro
            260                 265                 270

Phe Thr Phe Gly Ser Gly Thr Lys Leu Glu Ile Lys
        275                 280

<210> SEQ ID NO 25
<211> LENGTH: 284
<212> TYPE: PRT
<213> ORGANISM: Artificial Sequence
<220> FEATURE:
<223> OTHER INFORMATION: Synthetic Construct

<400> SEQUENCE: 25

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30
```

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Arg Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Ser Thr His Val Pro Phe Thr Phe Gly Ser Gly Thr Lys Leu
            115                 120                 125

Glu Ile Lys Gly Gly Gly Gly Ser Gly Gly Gly Gly Ser Gly Gly Gly
130                 135                 140

Gly Ser Met Lys Leu Trp Leu Asn Trp Ile Phe Pro Val Thr Leu Leu
145                 150                 155                 160

Asn Gly Ile Gln Cys Glu Val Lys Leu Val Glu Ser Gly Gly Gly Leu
                165                 170                 175

Val Gln Pro Gly Gly Ser Leu Arg Leu Ser Cys Ala Thr Ser Gly Phe
            180                 185                 190

Thr Phe Thr Asp Tyr His Met Asn Trp Val Arg Gln Pro Pro Gly Lys
        195                 200                 205

Ala Leu Glu Trp Leu Ala Leu Ile Arg Asn Lys Ala Asn Gly Tyr Arg
    210                 215                 220

Thr Glu Tyr Ser Ala Ser Val Lys Gly Arg Phe Thr Ile Ser Arg Asp
225                 230                 235                 240

Asn Ser Gln Asn Ile Leu Tyr Leu Gln Met Asn Thr Leu Arg Ala Glu
                245                 250                 255

Asp Ser Ala Thr Tyr Tyr Cys Ala Arg Asp Phe Tyr Asp Pro Phe Ala
            260                 265                 270

Tyr Trp Gly Gln Gly Thr Leu Val Thr Val Ser Ala
        275                 280

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Asp Tyr His Met Asn
1               5

<210> SEQ ID NO 27
<211> LENGTH: 19
<212> TYPE: PRT
<213> ORGANISM: Artificial Sequence
<220> FEATURE:
<223> OTHER INFORMATION: Synthetic Construct

<400> SEQUENCE: 27

Leu Ile Arg Asn Lys Ala Asn Gly Tyr Arg Thr Glu Tyr Ser Ala Ser
1               5                   10                  15

Val Lys Gly

<210> SEQ ID NO 28
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 28

Ser Gln Ser Thr Arg Val Pro Phe Thr
1               5

<210> SEQ ID NO 29
<211> LENGTH: 19
<212> TYPE: PRT
<213> ORGANISM: Artificial Sequence
<220> FEATURE:
<223> OTHER INFORMATION: Synthetic Construct

<400> SEQUENCE: 29

Met Lys Leu Trp Leu Asn Trp Ile Phe Leu Val Thr Leu Leu Asn Gly
1               5                   10                  15

Ile Gln Cys

<210> SEQ ID NO 30
<211> LENGTH: 19
<212> TYPE: PRT
<213> ORGANISM: Artificial Sequence
<220> FEATURE:
<223> OTHER INFORMATION: Synthetic Construct

<400> SEQUENCE: 30

Met Lys Leu Pro Val Gly Leu Leu Val Leu Met Phe Trp Ile Pro Ala
1               5                   10                  15

Ser Ser Ser
```